United States Patent
Hoff et al.

(10) Patent No.: US 11,732,221 B2
(45) Date of Patent: Aug. 22, 2023

(54) POLYPEPTIDES HAVING MANNANASE ACTIVITY AND POLYNUCLEOTIDES ENCODING SAME

(71) Applicant: Novozymes A/S, Bagsvaerd (DK)

(72) Inventors: Tine Hoff, Holte (DK); Markus Klinger, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/649,350

(22) PCT Filed: Oct. 2, 2018

(86) PCT No.: PCT/EP2018/076801
§ 371 (c)(1),
(2) Date: Mar. 20, 2020

(87) PCT Pub. No.: WO2019/068715
PCT Pub. Date: Apr. 11, 2019

(65) Prior Publication Data
US 2020/0299619 A1 Sep. 24, 2020

(30) Foreign Application Priority Data

Oct. 2, 2017 (EP) .................... 17194318

(51) Int. Cl.
| | | |
|---|---|---|
| C11D 3/386 | (2006.01) | |
| C12N 9/24 | (2006.01) | |
| C12N 1/14 | (2006.01) | |
| C12N 1/16 | (2006.01) | |
| C12N 1/20 | (2006.01) | |
| C12P 19/14 | (2006.01) | |
| C11D 17/00 | (2006.01) | |

(52) U.S. Cl.
CPC .......... *C11D 3/38636* (2013.01); *C11D 3/386* (2013.01); *C11D 17/0004* (2013.01); *C11D 17/0039* (2013.01); *C12N 1/14* (2013.01); *C12N 1/16* (2013.01); *C12N 1/20* (2013.01); *C12N 9/2488* (2013.01); *C12N 9/2491* (2013.01); *C12P 19/14* (2013.01); *C12Y 302/01025* (2013.01)

(58) Field of Classification Search
CPC . C11D 3/38636; C11D 3/386; C11D 17/0004; C11D 17/0039; C12N 1/14; C12N 1/16; C12N 1/20; C12N 9/2488; C12N 9/2491; C12P 19/14; C12Y 302/01025
See application file for complete search history.

(56) References Cited

U.S. PATENT DOCUMENTS

| | | | |
|---|---|---|---|
| 8,652,819 B2 | 2/2014 | Peterson | |
| 2015/0299623 A1* | 10/2015 | Gori | C11D 3/38654 8/137 |
| 2017/0183643 A1 | 6/2017 | Krogh et al. | |
| 2018/0320158 A1* | 11/2018 | Bao | C12N 9/2488 |

FOREIGN PATENT DOCUMENTS

| | | |
|---|---|---|
| CN | 105916985 A | 8/2016 |
| WO | 199/64619 A2 | 12/1999 |
| WO | 2001/62903 A1 | 8/2001 |
| WO | 2016/054176 A1 | 4/2016 |
| WO | 2017/079756 A1 | 5/2017 |

OTHER PUBLICATIONS

NCBI Reference Sequence WP_095357935.1, published Aug. 30, 2017 (Year: 2017).*
UniProt Accession No. A0A1R1FLI8_9BACL, published Apr. 12, 2017 (Year: 2017).*
Anonymous, 2017, NCBI Accession No. WP_095357935.
Beno, 2017, EBI Accession No. A0A1R1FLI8.
Cai et al, 2011, J Biosci Bioeng, vol. 112, No. 6, pp. 551-557.
Fu et al, 2010, J Microbiol Biotechnol, vol. 20, No. 3, pp. 518-524.
Jorgensen et al, 2010, Appl Biochem Biotechnol, vol. 161, No. 1-8, pp. 318-332.
Lee et al, 2010, Journal of the korean society for applied biological chemistry , vol. 53, No. 1, pp. 1-7.
Nunes et al, 2006, J Agric Food Chem, vol. 54, No. 9, pp. 3428-3439.
Songsiriritthigul et al, 2010, Micro Cell Fac, vol. 9, No. 1, p. 20.
Varnai et al, 2011, Bioresource Technology, vol. 102, No. 19, pp. 9096-9104.
Ward et al, 2009, EBI Access No. C6IWB6.
Guo et al., Chinese Agricultural Science Bulletin, 2017, 61-65, 33—Incl. Abstract.
Srivastava et al., Biotechnol Adv, 2017, 1-19, 35.

* cited by examiner

*Primary Examiner* — Ganapathirama Raghu
(74) *Attorney, Agent, or Firm* — Kelly Reynolds

(57) ABSTRACT

The present invention relates to polypeptides having mannanase activity, catalytic domains, and carbohydrate binding modules, and polynucleotides encoding the polypeptides, catalytic domains, and carbohydrate binding modules. The invention also relates to nucleic acid constructs, vectors, and host cells comprising the polynucleotides as well as methods of producing and using the polypeptides, catalytic domains, and carbohydrate binding modules.

18 Claims, No Drawings
Specification includes a Sequence Listing.

POLYPEPTIDES HAVING MANNANASE ACTIVITY AND POLYNUCLEOTIDES ENCODING SAME

CROSS-REFERENCE TO RELATED APPLICATIONS

This application is a 35 U.S.C. 371 national application of international application no. PCT/EP2018/076801 filed Oct. 2, 2018, which claims priority or the benefit under 35 U.S.C. 119 of European application no. 17194318.6 filed Oct. 2, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having mannanase activity, and polynucleotides encoding the polypeptides. The invention also relates to nucleic acid constructs, vectors, and host cells comprising the polynucleotides as well as methods of producing and using the polypeptides.

Description of the Related Art

Mannans are polysaccharides with a backbone of β-1,4-linked D-mannopyranosyl residues, which can contain galactose or acetyl substitutions and may have glucose residues in the backbone. The main enzyme type participating in the degradation of mannans are endo-1,4-β-mannanases (EC 3.2.1.78), which hydrolyze the internal glycoside bonds in the mannan backbone.

Mannans are a type of hemicellulose representing up to 25% of wood dry weight in softwoods, but are also found in other plant material, especially in a variety of seeds. The mannan containing guar gum is used as a stabilizer in many food products.

Thus it could be advantageous to use endomannanases in applications where mannan needs to be degraded. Examples of where mannanases could be used are in detergents to remove mannan containing stains, in the production of bioethanol from softwood (Várnai et al, (2011) "Synergistic action of xylanase and mannanase improves the total hydrolysis of softwood", *Bioresource tech.*, 102(19), pp. 9096-104) and palm kernel press cake (Jørgensen et al, (2010) "Production of ethanol and feed by high dry matter hydrolysis and fermentation of palm kernel press cake", *Applied Biochem. Biotech.*, 161(1-8), pp. 318-32), for the improvement of animal feed (Cai, et al, (2011), "Acidic β-mannanase from *Penicillium pinophilum* C1: Cloning, characterization and assessment of its potential for animal feed application", *J. Biosci. Bioeng.*, 112(6), pp. 551-557) and in the hydrolysis of coffee extract (Nunes et al, (2006), "Characterization of Galactomannan Derivatives in Roasted Coffee Beverages", *J. Agricultural Food Chem.*, 54(9), pp. 3428-3439).

According to CAZy (www.cazy.org), endo-1,4-β-mannanases have been found in glycoside hydrolase families 5, 26 and 113. The present invention provides polypeptides of glycoside hydrolase family 26 having mannanase activity and polynucleotides encoding the polypeptides that are highly active in degrading different types of mannan, and therefore could be used in the aforementioned applications.

SUMMARY OF THE INVENTION

The present invention relates to polypeptides having mannanase activity selected from the group consisting of:
(a) a polypeptide having at least 91% sequence identity to SEQ ID NO: 4;
(b) a variant of SEQ ID NO: 4, wherein the variant has mannanase activity and comprises one or more substitutions, and/or one or more deletions, and/or one or more insertions or any combination thereof in 1 to 29 positions;
(c) a polypeptide comprising the polypeptide of (a) or (b) and a N-terminal and/or C-terminal His-tag and/or HQ-tag;
(d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide.

The present invention further relates to detergent compositions comprising a surfactant and a polypeptide having mannanase activity, wherein the polypeptide is selected from the group consisting of:
(a) a polypeptide having at least 81% sequence identity to SEQ ID NO: 3;
(b) a variant of SEQ ID NO: 4, wherein the variant has mannanase activity and comprises one or more substitutions, and/or one or more deletions, and/or one or more insertions or any combination thereof in 1 to 50 positions;
(c) a polypeptide comprising the polypeptide of (a) or (b) and a N-terminal and/or C-terminal His-tag and/or HQ-tag;
(d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide.

The present invention further relates to granules comprising a core particle and one or more coatings, wherein the granule comprises a polypeptide having mannanase activity as defined above, and liquid compositions comprising a polyol and a polypeptide having mannanase activity, wherein the polypeptide is as defined above. The invention further relates to uses of the peptide in various applications such as degrading mannan, laundering, washing, cleaning, feed, food, extracting coffee, degrading cellulosic material, producing a fermentation product, isolated polynucleotides encoding the polypeptides of the invention, recombinant host cells and method of producing the polypeptide of the invention.

Overview of Sequence Listing

SEQ ID NO: 1 is the DNA sequence of the native GH26 mannanase comprising a CBM35 domain as isolated from a strain of *Paenibacillus illinoisensis*.

SEQ ID NO: 2 is the amino acid sequence as deduced from SEQ ID NO: 1.

SEQ ID NO: 3 is the amino acid sequence of the mature GH26 mannanase from a strain of *Paenibacillus illinoisensis* with CBM35 domain.

SEQ ID NO: 4 is the amino acid sequence of the truncated mature GH26 mannanase from a strain of *Paenibacillus illinoisensis* missing the CBM35 domain.

SEQ ID NO: 5 is a construct DNA sequence of the GH26 mannanase from a strain of *Paenibacillus illinoisensis* comprising a CBM35 wherein the native secretion signal was replaced with a *Bacillus clausii* secretion signal and a 6×His tag was added directly on the C-terminal of the protein.

SEQ ID NO: 6 is the amino acid sequence as deduced from SEQ ID NO: 5.

SEQ ID NO: 7 is a construct DNA sequence of the truncated GH26 mannanase missing the CBM35 domain wherein the native secretion signal was replaced with a *Bacillus licheniformis* secretion signal and a 6×His tag was added directly on the C-terminal of the protein.

SEQ ID NO: 8 is the amino acid sequence as deduced from SEQ ID NO: 7.

SEQ ID NO: 9 is the amino acid sequence of a *Bacillus clausii* secretion signal.

SEQ ID NO: 10 is the amino acid sequence of a *Bacillus licheniformis* secretion signal.

SEQ ID NO: 11 is the DNA sequence of the native GH26 mannanase comprising a CBM35 domain as isolated from a strain of *Paenibacillus* sp.

SEQ ID NO: 12 is the amino acid sequence as deduced from SEQ ID NO: 11.

SEQ ID NO: 13 is the amino acid sequence of the mature GH26 mannanase from a strain of *Paenibacillus illinoisensis* with CBM35 domain.

SEQ ID NO: 14 is a construct DNA sequence of the GH26 mannanase from a strain of *Paenibacillus* sp. comprising a CBM35 domain wherein the native secretion signal was replaced with a *Bacillus licheniformis* secretion signal and a HPHPHPHP tag was added directly on the C-terminal of the protein.

SEQ ID NO: 15 is the amino acid sequence as deduced from SEQ ID NO: 14.

SEQ ID NO: 16 is the HPHPHPHP tag.

SEQ ID NO: 17 is a His tag.

Definitions

In accordance with the detailed description, the following abbreviations and definitions apply. Note that the singular forms "a", "an", and "the" include plural referents unless the context clearly indicates otherwise. Thus, for example, reference to "an enzyme" includes a plurality of such enzymes, and reference to "the dosage" includes reference to one or more dosages and equivalents thereof known to those skilled in the art, and so forth.

Auxiliary Activity 9: The term "Auxiliary Activity 9" or "AA9" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: The term "biofilm" means any group of microorganisms in which cells stick to each other on a surface, such as a textile, dishware or hard surface. These adherent cells are frequently embedded within a self-produced matrix of extracellular polymeric substance (EPS).

Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One effect of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp.

Carbohydrate binding module: The term "carbohydrate binding module" means the region within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose. In one embodiment, the CBM is a family 35 CBM (Pfam PF16990) such as that disclosed in Tunnicliffe R B, Bolam D N, Pell G, Gilbert H J, Williamson M P; J Mol Biol. 2005; 347:287-296.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Chimeric polypeptide: The term "chimeric polypeptide" means a polypeptide having mannanase activity whose composition is generated by replacing a sequence of amino acids from one polypeptide having mannanase activity with those from homologous positions of one or more other polypeptides having mannanase activity.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish wash detergents). In addition to containing a GH9 endoglucanase of the invention and/or xanthan lyase of the invention, the detergent formulation may contain one or more additional enzymes (such as amylases, proteases, proteases, peroxidases, cellulases, beta-glucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, and combinations thereof, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

Dish wash: The term "dish wash" refers to all forms of washing dishes, e.g. by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present invention is not restricted to any particular type of dish wash composition or any particular detergent.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or carbohydrate binding module having one or more (e.g., several) amino acids absent from the amino and/or carboxyl terminus of a mature polypeptide or domain; wherein the fragment has mannanase or carbohydrate binding activity. In one aspect, the fragment comprises at least 90% of the length of the mature polypeptide, such as at least 441 amino acids of SEQ ID NO: 3, or at least 280 amino acids of SEQ ID NO: 4, or at least 441 amino acids of SEQ ID NO: 13. In one aspect, the fragment comprises at least 92% of the length of the mature polypeptide, such as at least 451 amino acids of SEQ ID NO: 3, or at least 287 amino acids of SEQ ID NO: 4, or at least 451 amino acids of SEQ ID NO: 13. In one aspect, the fragment comprises at least 94% of the length of the mature polypeptide, such as at least 461 amino acids of SEQ ID NO: 3, or at least 293 amino acids of SEQ ID NO: 4, or at least 461 amino acids of SEQ ID NO: 13. In one aspect, the fragment comprises at least 96% of the length of the mature polypeptide, such as at least 471 amino acids of SEQ ID NO: 3, or at least 299 amino acids of SEQ ID NO: 4, or at least 471 amino acids of SEQ ID NO: 13. In one aspect, the fragment comprises at least 98% of the length of the mature polypeptide, such as at least 481 amino acids of SEQ ID NO: 3, or at least 305 amino acids of SEQ ID NO: 4, or at least 481 amino acids of SEQ ID NO: 13. In one aspect, the fragment comprises at least 99% of the length of the mature polypeptide, such as at least 486 amino acids of SEQ ID NO: 3, or at least 308 amino acids of SEQ ID NO: 4, or at least 486 amino acids of SEQ ID NO: 13.

Fusion polypeptide: The term "fusion polypeptide" is a polypeptide in which one polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication, as well as a recombinant host cell, an isolated host cell (e.g., an isolated recombinant host cell), a heterologous host cell (e.g., a host cell that is not *Myrothecium roridum* host cell).

Hybrid polypeptide: The term "hybrid polypeptide" means a polypeptide comprising domains from two or more polypeptides, e.g., a binding domain from one polypeptide and a catalytic domain from another polypeptide. The domains may be fused at the N-terminus or the C-terminus.

Isolated: The term "isolated" means a substance in a form that does not occur in nature or in an environment in which the substance does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Mannanase: The term "mannanase" means a polypeptide having mannan endo-1,4-beta-mannosidase activity (EC 3.2.1.78) that catalyzes the hydrolysis of 1,4-β-D-mannosidic linkages in mannans, galactomannans and glucomannans. Alternative names of mannan endo-1,4-beta-mannosidase are 1,4-β-D-mannan mannanohydrolase; endo-1,4-β-mannanase; endo-β-1,4-mannase; β-mannanase B; β-1,4-mannan 4-mannanohydrolase; endo-β-mannanase; and β-D-mannanase. For purposes of the present invention, mannanase activity may be determined using the Reducing End Assay as described in Example 1 herein. In one aspect, the polypeptides of the present invention have at least 50%, e.g., at least 60%, at least 70%, at least 80%, at least 90%, at least 95%, or at least 100% of the mannanase activity of the mature polypeptide of SEQ ID NO: 3. In one aspect, the polypeptides of the present invention have at least 50%, e.g., at least 60%, at least 70%, at least 80%, at least 90%, at least 95%, or at least 100% of the mannanase activity of the mature polypeptide of SEQ ID NO: 13.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 491 of SEQ ID NO: 3. In one aspect, the mature polypeptide is amino acids 1 to 312 of SEQ ID NO: 4. In one aspect, the mature polypeptide is amino acids 1 to 491 of SEQ ID NO: 13.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having mannanase activity. In one aspect, the mature polypeptide coding sequence is nucleotides 127 to 1599 of SEQ ID NO: 1, or of SEQ ID NO: 11. The nucleotides 1 to 126 of SEQ ID NO: 1 or SEQ ID NO: 11 encode a signal peptide.

Malodor: The term "malodor" is meant an odor which is not desired on clean items. The cleaned item should smell fresh and clean without malodors adhered to the item. One example of malodor is compounds with an unpleasant smell, which may be produced by microorganisms. Another example is sweat or body odor adheringed to an item which has been in contact with humans or animals. Another example of malodor can be the smell from spices, for example curry or other exotic spices adheringed to an item such as a piece of textile. One way of measuring the ability of an item to adhere malodor is by using the Malodor Assay.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 6.6.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having mannanase activity.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

Variant: The term "variant" means a polypeptide having mannanase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention have at least 50%, e.g., at least 60%, at least 70%, at least 80%, at least 90%, at least 95%, or at least 100% of the mannanase activity of the polypeptide of SEQ ID NO: 3.

DETAILED DESCRIPTION OF THE INVENTION

Polypeptides Having Mannanase Activity

In a first aspect, the invention relates to polypeptides having mannanase activity having at least 91%, e.g., at least 92%, at least 93%, at least 94%, at least 95%, at least 96%, at least 97%, at least 98%, at least 99%, or 100% sequence identity to SEQ ID NO: 4. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28 or 29 amino acids from SEQ ID NO: 4.

In one embodiment, the polypeptide preferably comprises or consists of the amino acid sequence of SEQ ID NO: 4; comprises the amino acid sequence of SEQ ID NO: 4 and a N-terminal and/or C-terminal His-tag and/or HQ-tag (such as SEQ ID NO: 8); comprises the amino acid sequence of SEQ ID NO: 4 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 4. In an embodiment, the polypeptide comprises or consists of amino acids 1 to 312 of SEQ ID NO: 4. In an embodiment, the polypeptide comprises or consists of amino acids 1 to 318 of SEQ ID NO: 8. In an embodiment, the polypeptide has been isolated.

In a continuation of the first aspect, the invention relates to variants of SEQ ID NO: 4 having mannanase activity comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions. In an embodiment, the number of positions comprising one or more amino acid substitutions, and/or one or more amino acid deletions, and/or one or more amino acid insertions or any combination thereof in SEQ ID NO: 4 is not more than 10, e.g., 1, 2, 3, 4, 5, 6, 7, 8, 9 or 10. In another embodiment, the number of substitutions and/or deletions and/or insertions in SEQ ID NO: 4 is not more than 10, e.g., 1, 2, 3, 4, 5, 6, 7, 8, 9 or 10. In a further embodiment, the number of substitutions, preferably conservative substitutions, in SEQ ID NO: 4 is not more than 10, e.g., 1, 2, 3, 4, 5, 6, 7, 8, 9 or 10.

In one embodiment to any part of the first aspect, the polypeptide or variant has at least 60%, such as at least 70%, at least 80%, at least 90%, at least 95%, or at least 100% of the mannanase activity of SEQ ID NO: 4.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for mannanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide or a fusion polypeptide

In one embodiment of the first aspect, the polypeptide or variant of the first aspect of the invention further comprises a carbohydrate binding module. In an embodiment, the carbohydrate binding module is a family 35 CBM. In a further embodiment, the polypeptide or variant of the first aspect of the invention comprises a catalytic domain and a CBM and has at least 87%, e.g., at least 90%, at least 91%, at least 92%, at least 93%, at least 94%, at least 95%, at least 96%, at least 97%, at least 98%, at least 99%, or 100% sequence identity to SEQ ID NO: 3. In one embodiment, the polypeptide comprises or consists of the mature polypeptide of SEQ ID NO: 2, amino acids 1 to 491 of SEQ ID NO: 2 or amino acids 1 to 491 of SEQ ID NO: 3. In an embodiment, the polypeptide or variant of the first aspect of the invention comprises a catalytic domain and a CBM and has at least 87%, e.g., at least 90%, at least 91%, at least 92%, at least 93%, at least 94%, at least 95%, at least 96%, at least 97%, at least 98%, at least 99%, or 100% sequence identity to SEQ ID NO: 13. In one embodiment, the polypeptide comprises or consists of the mature polypeptide of SEQ ID NO: 12, amino acids 1 to 491 of SEQ ID NO: 12 or amino acids 1 to 491 of SEQ ID NO: 13.

In a second aspect, the invention relates to polypeptides having mannanase activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 3 or from SEQ ID NO: 13.

In one embodiment, the polypeptide preferably comprises or consists of the amino acid sequence of SEQ ID NO: 3; comprises the amino acid sequence of SEQ ID NO: 3 and a N-terminal and/or C-terminal His-tag and/or HQ-tag (such as SEQ ID NO: 6); comprises the amino acid sequence of SEQ ID NO: 3 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 3. In an embodiment, the polypeptide comprises or consists of the mature polypeptide of SEQ ID NO: 2 or amino acids 1 to 491 of SEQ ID NO: 2. In an embodiment, the polypeptide comprises or consists of amino acids 1 to 491 of SEQ ID NO: 3. In an embodiment, the polypeptide has been isolated.

In a continuation of the second aspect, the invention relates to variants of SEQ ID NO: 3 having mannanase activity comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In another embodiment, the number of substitutions and/or deletions and/or insertions in SEQ ID NO: 3 is not more than 10, e.g., 1, 2, 3, 4, 5, 6, 7, 8, 9 or 10. In a further embodiment, the number of substitutions, preferably conservative substitutions, in SEQ ID NO: 3 is not more than 10, e.g., 1, 2, 3, 4, 5, 6, 7, 8, 9 or 10. Examples of amino acid changes and conservative substitutions are described in the first aspect of the invention.

In one embodiment to any part of the second aspect, the polypeptide or variant has at least 60%, such as at least 70%, at least 80%, at least 90%, at least 95%, or at least 100% of the mannanase activity of SEQ ID NO: 3.

In one embodiment, the polypeptide preferably comprises or consists of the amino acid sequence of SEQ ID NO: 13; comprises the amino acid sequence of SEQ ID NO: 3 and a N-terminal and/or C-terminal His-tag and/or HQ-tag; comprises the amino acid sequence of SEQ ID NO: 13 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 13. In an embodiment, the polypeptide comprises or consists of the mature polypeptide of SEQ ID NO: 12 or amino acids 1 to 491 of SEQ ID NO: 12. In an embodiment, the polypeptide comprises or consists of amino acids 1 to 491 of SEQ ID NO: 13. In an embodiment, the polypeptide has been isolated.

In a continuation of the second aspect, the invention relates to variants of SEQ ID NO: 13 having mannanase activity comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 13 is not more than 10, e.g., 1, 2, 3, 4, 5, 6, 7, 8, 9 or 10. In another embodiment, the number of substitutions and/or deletions and/or insertions in SEQ ID NO: 13 is not more than 10, e.g., 1, 2, 3, 4, 5, 6, 7, 8, 9 or 10. In a further embodiment, the number of substitutions, preferably conservative substitutions, in SEQ ID NO: 13 is not more than 10, e.g., 1, 2, 3, 4, 5, 6, 7, 8, 9 or 10. Examples of amino acid changes and conservative substitutions are described in the first aspect of the invention.

In one embodiment to any part of the second aspect, the polypeptide or variant has at least 60%, such as at least 70%, at least 80%, at least 90%, at least 95%, or at least 100% of the mannanase activity of SEQ ID NO: 13.

Detergent Compositions Comprising Polypeptides Having Mannanase Activity

In a third aspect, the invention relates to a detergent composition comprising a surfactant and a polypeptide having mannanase activity, wherein the polypeptide has at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 4.

In one embodiment, the polypeptide preferably comprises or consists of the amino acid sequence of SEQ ID NO: 4; comprises the amino acid sequence of SEQ ID NO: 4 and a N-terminal and/or C-terminal His-tag and/or HQ-tag (such as SEQ ID NO: 8); comprises the amino acid sequence of SEQ ID NO: 4 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 4. In an embodiment, the polypeptide comprises or consists of amino acids 1 to 312 of SEQ ID NO: 4. In an embodiment, the polypeptide comprises or consists of amino acids 1 to 318 of SEQ ID NO: 8. In an embodiment, the polypeptide has been isolated.

In a continuation of the third aspect, the invention relates to a detergent composition comprising a surfactant and a variant having mannanase activity, wherein variant comprises one or more amino acid substitutions, and/or one or more amino acid deletions, and/or one or more amino acid insertions or any combination thereof of SEQ ID NO: 4 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 4 is not more than 10, e.g., 1, 2, 3, 4, 5, 6, 7, 8, 9 or 10. In another embodiment, the number of substitutions and/or deletions and/or insertions in SEQ ID NO: 4 is not more than 10, e.g., 1, 2, 3, 4, 5, 6, 7, 8, 9 or 10. In a further embodiment, the number of substitutions, preferably conservative substitutions, in SEQ ID NO: 4 is not more than 10, e.g., 1, 2, 3, 4, 5, 6, 7, 8, 9 or 10. Examples of amino acid changes and conservative substitutions are described in the first aspect of the invention.

In one embodiment to any part of the second aspect, the polypeptide or variant has at least 60%, such as at least 70%, at least 80%, at least 90%, at least 95%, or at least 100% of the mannanase activity of SEQ ID NO: 3.

In one embodiment, the polypeptide or variant of the third aspect of the invention further comprises a carbohydrate binding module. In an embodiment, the carbohydrate binding module is a family 35 CBM. In a further embodiment, the polypeptide polypeptide or variant of the first aspect of the invention comprises a catalytic domain and a CBM and has at least 87%, e.g., at least 90%, at least 91%, at least 92%, at least 93%, at least 94%, at least 95%, at least 96%, at least 97%, at least 98%, at least 99%, or 100% sequence identity to SEQ ID NO: 3. In one embodiment, the polypeptide comprises or consists of the mature polypeptide of SEQ ID NO: 2, amino acids 1 to 491 of SEQ ID NO: 2 or amino acids 1 to 491 of SEQ ID NO: 3.

In one embodiment to any part of the second aspect, the polypeptide or variant has at least 60%, such as at least 70%, at least 80%, at least 90%, at least 95%, or at least 100% of the mannanase activity of SEQ ID NO: 13.

In one embodiment, the polypeptide or variant of the third aspect of the invention further comprises a carbohydrate binding module. In an embodiment, the carbohydrate binding module is a family 35 CBM. In a further embodiment, the polypeptide polypeptide or variant of the first aspect of the invention comprises a catalytic domain and a CBM and has at least 87%, e.g., at least 90%, at least 91%, at least 92%, at least 93%, at least 94%, at least 95%, at least 96%, at least 97%, at least 98%, at least 99%, or 100% sequence identity to SEQ ID NO: 13. In one embodiment, the polypeptide comprises or consists of the mature polypeptide of SEQ ID NO: 12, amino acids 1 to 491 of SEQ ID NO: 12 or amino acids 1 to 491 of SEQ ID NO: 13.

In a fourth aspect, the invention relates to a detergent composition comprising a surfactant and a polypeptide having mannanase activity, wherein the polypeptide has at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 3 or SEQ ID NO: 13.

In one embodiment, the polypeptide preferably comprises or consists of the amino acid sequence of SEQ ID NO: 3 or SEQ ID NO: 13; comprises the amino acid sequence of SEQ ID NO: 3 or SEQ ID NO: 13 and a N-terminal and/or C-terminal His-tag and/or HQ-tag (such as SEQ ID NO: 6); comprises the amino acid sequence of SEQ ID NO: 3 or SEQ ID NO: 13 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 3 or SEQ ID NO: 13. In an embodiment, the polypeptide comprises or consists of the mature polypeptide of SEQ ID NO: 2 or amino acids 1 to 491 of SEQ ID NO: 2 or the mature polypeptide of SEQ ID NO: 12 or amino acids 1 to 491 of SEQ ID NO: 12. In an embodiment, the polypeptide comprises or consists of amino acids 1 to 491 of SEQ ID NO: 3 comprises or consists of amino acids 1 to 491 of SEQ ID NO: 13. In an embodiment, the polypeptide has been isolated.

In a continuation of the fourth aspect, the invention relates to a detergent composition comprising a surfactant and a variant having mannanase activity, wherein variant comprises one or more amino acid substitutions, and/or one or more amino acid deletions, and/or one or more amino acid insertions or any combination thereof of SEQ ID NO: 3 or SEQ ID NO: 13 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 3 or SEQ ID NO: 13 is not more than 10, e.g., 1, 2, 3, 4, 5, 6, 7, 8, 9 or 10. In another embodiment, the number of substitutions and/or deletions and/or insertions in SEQ ID NO: 3 or SEQ ID NO: 13 is not more than 10, e.g., 1, 2, 3, 4, 5, 6, 7, 8, 9 or 10. In a further embodiment, the number of substitutions, preferably conservative substitutions, in SEQ ID NO: 3 or SEQ ID NO: 3 is not more than 10, e.g., 1, 2, 3, 4, 5, 6, 7, 8, 9 or 10. Examples of amino acid changes and conservative substitutions are described in the first aspect of the invention.

Examples of surfactants and preferred amounts and surfactants are discussed below in the surfactants section.

In an embodiment to any part of the third or fourth aspects, the detergent composition may further comprise one or more components selected from the group consisting of hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants and solubilizers.

In an embodiment to any part of the third or fourth aspects, the detergent composition may further comprise one or more additional enzyme selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases and transglutaminases.

Granules Comprising Polypeptides Having Mannanase Activity

In a fifth aspect, the invention relates to a granule comprising a core particle and one or more coatings, wherein the granule comprises a polypeptide having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 4.

In one embodiment, the polypeptide preferably comprises or consists of the amino acid sequence of SEQ ID NO: 4; comprises the amino acid sequence of SEQ ID NO: 4 and a N-terminal and/or C-terminal His-tag and/or HQ-tag (such as SEQ ID NO: 8); comprises the amino acid sequence of SEQ ID NO: 4 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 4. In an embodiment, the polypeptide comprises or consists of amino acids 1 to 312 of SEQ ID NO: 4. In an embodiment, the polypeptide comprises or consists of amino acids 1 to 318 of SEQ ID NO: 8. In an embodiment, the polypeptide has been isolated.

In a continuation of the fifth aspect, the invention relates to a granule comprising a core particle and one or more coatings, wherein the granule comprises a variant of SEQ ID NO: 4 having mannanase activity and one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 4 is not more than 10, e.g., 1, 2, 3, 4, 5, 6, 7, 8, 9 or 10. In another embodiment, the number of substitutions and/or deletions and/or insertions in SEQ ID NO: 4 is not more than 10, e.g., 1, 2, 3, 4, 5, 6, 7, 8, 9 or 10. In a further embodiment, the number of substitutions, preferably conservative substitutions, in SEQ ID NO: 4 is not more than 10, e.g., 1, 2, 3, 4, 5, 6, 7, 8, 9 or 10. Examples of amino acid changes and conservative substitutions are described in the first aspect of the invention.

In one embodiment to any part of the second aspect, the polypeptide or variant has at least 60%, such as at least 70%, at least 80%, at least 90%, at least 95%, or at least 100% of the mannanase activity of SEQ ID NO: 3 or SEQ ID NO: 13.

In one embodiment, the polypeptide or variant of the fifth aspect of the invention further comprises a carbohydrate binding module. In an embodiment, the carbohydrate binding module is a family 35 CBM. In a further embodiment, the polypeptide polypeptide or variant of the first aspect of the invention comprises a catalytic domain and a CBM and has at least 87%, e.g., at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13. In one embodiment, the polypeptide comprises or consists of the mature polypeptide of SEQ ID NO: 2, amino acids 1 to 491 of SEQ ID NO: 2 or amino acids 1 to 491 of SEQ ID NO: 3. In one embodiment, the polypeptide comprises or consists of the mature polypeptide of SEQ ID NO: 12, amino acids 1 to 491 of SEQ ID NO: 12 or amino acids 1 to 491 of SEQ ID NO: 13.

In a sixth aspect, the invention relates to a granule comprising a core particle and one or more coatings, wherein the granule comprises a polypeptide having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 3 or SEQ ID NO: 13.

In one embodiment, the polypeptide preferably comprises or consists of the amino acid sequence of SEQ ID NO: 3 or SEQ ID NO: 13; comprises the amino acid sequence of SEQ ID NO: 3 or SEQ ID NO: 13 and a N-terminal and/or C-terminal His-tag and/or HQ-tag (such as SEQ ID NO: 6); comprises the amino acid sequence of SEQ ID NO: 3 or SEQ ID NO: 13 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 3 or SEQ ID NO: 13. In an embodiment, the polypeptide comprises or consists of the mature polypeptide of SEQ ID NO: 2 or amino acids 1 to 491 of SEQ ID NO: 2. In an embodiment, the polypeptide comprises or consists of amino acids 1 to 491 of SEQ ID NO: 3. In an embodiment, the polypeptide comprises or consists of the mature polypeptide of SEQ ID NO: 12 or amino acids 1 to 491 of SEQ ID NO: 12. In an embodiment, the polypeptide comprises or consists of amino acids 1 to 491 of SEQ ID NO: 13. In an embodiment, the polypeptide has been isolated.

In a continuation of the sixth aspect, the invention relates to a granule comprising a core particle and one or more coatings, wherein the granule comprises a variant of SEQ ID NO: 3 or SEQ ID NO: 13 having mannanase activity and one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 3 or SEQ ID NO: 13 is not more than 10, e.g., 1, 2, 3, 4, 5, 6, 7, 8, 9 or 10. In another embodiment, the number of substitutions and/or deletions and/or insertions in SEQ ID NO: 3 or SEQ ID NO: 13 is not more than 10, e.g., 1, 2, 3, 4, 5, 6, 7, 8, 9 or 10. In a further embodiment, the number of substitutions, preferably conservative substitutions, in SEQ ID NO: 3 or SEQ ID NO: 13 is not more than 10, e.g., 1, 2, 3, 4, 5, 6, 7, 8, 9 or 10.

Examples of amino acid changes and conservative substitutions are described in the first aspect of the invention.

The granule of any of aspects five and six may further comprise one or more formulating agents, as discussed below in the formulation section. Preferred formulating agents are glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

In an embodiment to any part of the fifth or sixth aspects, the granule may further comprise one or more additional enzyme selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases and transglutaminases.

Liquid Formulations Comprising Polypeptides Having Mannanase Activity

In a seventh aspect, the invention relates to a liquid composition comprising a polyol and a polypeptide having mannanase activity, wherein the polypeptide has at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 4.

In one embodiment, the polypeptide preferably comprises or consists of the amino acid sequence of SEQ ID NO: 4; comprises the amino acid sequence of SEQ ID NO: 4 and a N-terminal and/or C-terminal His-tag and/or HQ-tag (such as SEQ ID NO: 8); comprises the amino acid sequence of SEQ ID NO: 4 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 4. In an embodiment, the polypeptide comprises or consists of amino acids 1 to 312 of SEQ ID NO: 4. In an embodiment, the polypeptide comprises or consists of amino acids 1 to 318 of SEQ ID NO: 8. In an embodiment, the polypeptide has been isolated.

In a continuation of the seventh aspect, the invention relates to a liquid composition comprising a polyol and a variant having mannanase activity, wherein variant comprises one or more amino acid substitutions, and/or one or more amino acid deletions, and/or one or more amino acid insertions or any combination thereof of SEQ ID NO: 4 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 4 is not more than 10, e.g., 1, 2, 3, 4, 5, 6, 7, 8, 9 or 10. In another embodiment, the number of substitutions and/or deletions and/or insertions in SEQ ID NO: 4 is not more than 10, e.g., 1, 2, 3, 4, 5, 6, 7, 8, 9 or 10. In a further embodiment, the number of substitutions, preferably conservative substitutions, in SEQ ID NO: 4 is not more than 10, e.g., 1, 2, 3, 4, 5, 6, 7, 8, 9 or 10. Examples of amino acid changes and conservative substitutions are described in the first aspect of the invention.

In one embodiment to any part of the second aspect, the polypeptide or variant has at least 60%, such as at least 70%, at least 80%, at least 90%, at least 95%, or at least 100% of the mannanase activity of SEQ ID NO: 3 or SEQ ID NO: 3.

In one embodiment, the polypeptide or variant of the seventh aspect of the invention further comprises a carbohydrate binding module. In an embodiment, the carbohydrate binding module is a family 35 CBM. In a further embodiment, the polypeptide polypeptide or variant of the first aspect of the invention comprises a catalytic domain and a CBM and has at least 87%, e.g., at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13. In one embodiment, the polypeptide comprises or consists of the mature polypeptide of SEQ ID NO: 2, amino acids 1 to 491 of SEQ ID NO: 2 or amino acids 1 to 491 of SEQ ID NO: 3. In one embodiment, the polypeptide comprises or consists of the mature polypeptide of SEQ ID NO: 12, amino acids 1 to 491 of SEQ ID NO: 12 or amino acids 1 to 491 of SEQ ID NO: 13.

In an eighth aspect, the invention relates to a liquid composition comprising a polyol and a polypeptide having mannanase activity, wherein the polypeptide has at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 3 or SEQ ID NO: 13.

In one embodiment, the polypeptide preferably comprises or consists of the amino acid sequence of SEQ ID NO: 3 or SEQ ID NO: 13; comprises the amino acid sequence of SEQ ID NO: 3 or SEQ ID NO: 13 and a N-terminal and/or C-terminal His-tag and/or HQ-tag (such as SEQ ID NO: 6); comprises the amino acid sequence of SEQ ID NO: 3 or SEQ ID NO: 13 and a N-terminal and/or C-terminal extension of between 1 and 10 amino acids; or is a fragment thereof having mannanase activity and having at least 90% such as at least 91%, at least 92%, at least 93%, at least 94%, at least 95%, at least 96%, at least 97%, at least 98% or at least 99% of the length of SEQ ID NO: 3 or SEQ ID NO: 13. In an embodiment, the polypeptide comprises or consists of the mature polypeptide of SEQ ID NO: 2 or amino acids 1 to 491 of SEQ ID NO: 2. In an embodiment, the polypeptide comprises or consists of amino acids 1 to 491 of SEQ ID NO: 3. In an embodiment, the polypeptide comprises or consists of the mature polypeptide of SEQ ID NO: 12 or amino acids 1 to 491 of SEQ ID NO: 12. In an embodiment, the polypeptide comprises or consists of amino acids 1 to 491 of SEQ ID NO: 13. In an embodiment, the polypeptide has been isolated.

In a continuation of the eighth aspect, the invention relates to a liquid composition comprising a polyol and a variant having mannanase activity, wherein the variant comprises one or more amino acid substitutions, and/or one or more amino acid deletions, and/or one or more amino acid insertions or any combination thereof of SEQ ID NO: 3 or SEQ ID NO: 13 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 position. In an embodiment, the number of positions comprising one or more amino acid substitutions, and/or one or more amino acid deletions, and/or one or more amino acid insertions or any combination thereof in SEQ ID NO: 3 or SEQ ID NO: 13 is not more than 10, e.g., 1, 2, 3, 4, 5, 6, 7, 8, 9 or 10. In another embodiment, the number of substitutions and/or deletions and/or insertions in SEQ ID NO: 3 is not more than 10, e.g., 1, 2, 3, 4, 5, 6, 7, 8, 9 or 10. In a further embodiment, the number of substitutions, preferably conservative substitutions, in SEQ ID NO: 3 or SEQ ID NO: 13 is not more than 10, e.g., 1, 2, 3, 4, 5, 6, 7, 8, 9 or 10. Examples of amino acid changes and conservative substitutions are described in the first aspect of the invention.

In one embodiment to any part of the seventh or eighth aspect, the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment to any part of the seventh or eighth aspect, the liquid formulation comprises 5%-80% polyol (i.e. total amount of polyol), preferably 15%-75% polyol, more preferably 25%-70% polyol, more preferably 35%-65% polyol or most preferably 40%-60% polyol. In one embodiment to any part of the seventh or eighth aspect, the liquid formulation comprises 5%-80% polyol, preferably 15%-75% polyol, more preferably 25%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600. In one embodiment to any part of the seventh or eighth aspect, the liquid formulation comprises 5%-80% polyol, preferably 15%-75% polyol, more preferably 25%-70% polyol, more preferably 35%-65% polyol or most preferably 40%-60% polyol wherein the polyol is selected from the group consisting of glycerol, sorbitol and propylene glycol (MPG).

In one embodiment to any part of the seventh or eighth aspect, the formulation further comprises 0.001% to 2.0% w/w preservative. In one embodiment, the preservative is selected from the group consisting of phenoxy ethanol, 1,2-benzisothiazolin-3(2H)-one, sodium sorbate, potassium sorbate, sodium benzoate, potassium benzoate, methylisothiazolinone, chloro methylisothiazolinone, methyl parabene, ethyl parabene, propyl parabene, butyl parabene, quarterary ammonium salts (such as BAC/ADBAC; alkylbenzyl quarternary ammonium chloride, dioctyldimethylammonium chloride, didecyldimethylammonium chloride, cetrimonium chloride), essential oils and organic acids or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.001% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of phenoxy ethanol, 1,2-benzisothiazolin-3(2H)-one, sodium sorbate, potassium sorbate, sodium benzoate and potassium benzoate or any combination thereof.

In one embodiment to any part of the seventh or eighth aspect, the mannanase is dosed between 0.0001% to 10% w/w of liquid formulation, such as 0.001% to 0.1% w/w polypeptide, 0.01% to 1.0% w/w polypeptide or 0.1% to 10% w/w polypeptide.

In one embodiment to any part of the seventh or eighth aspect, the liquid formulation comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the seventh or eighth aspect, the liquid formulation may further comprise one or more additional enzyme selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases and transglutaminases.

Sources of Polypeptides Having Mannanase Activity

A polypeptide having mannanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a polypeptide having mannanase activity from within a phylum such as Firmicutes.

In one aspect, the polypeptide is a mannanase from a fungus of the class Bacilli, such as from the order Bacillales, from the family Paenibacillaceae, from the genus *Paenibacillus* or from the species *Paenibacillus illinoisensis* or *Paenibacillus* sp.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus* or a related organism from Bacillales, and thus, for example, may be an allelic or species variant of the polypeptide encoding region of the polynucleotide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coil* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase Ill, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5′-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium*

*bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention (e.g., in vitro or ex vivo methods of production), comprising (a) cultivating a cell, which in its wild-type form produces the polypeptide, under conditions conducive for production of the polypeptide; and optionally, (b) recovering the polypeptide. In one aspect, the cell is an *Paenibacillus* cell. In another aspect, the cell is an *Paenibacillus illinoisensis* or a *Paenibacillus* sp. cell.

The present invention also relates to methods of producing a polypeptide of the present invention (e.g., in vitro or ex vivo methods of production), comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Cleaning Compositions and/or Detergent Compositions

The present invention also relates to compositions comprising a mannanase of the invention, such as cleaning compositions and/or detergent compositions.

In one embodiment, the present invention relates to cleaning compositions and/or detergent compositions comprising a mannanase of the invention and a suitable surfactant. In one embodiment, the detergent composition may be adapted for specific uses such as laundry, in particular household laundry, dish washing or hard surface cleaning.

Thus in one embodiment, the polypeptide of aspect one or two, detergent composition of aspect three or four, granule of aspect five or six or liquid formulation of aspect seven or eight may be used for laundering, washing or cleaning a textile and/or a hard surface (such as dish wash). In an embodiment, the polypeptide has an enzyme detergency benefit (i.e. the enzyme of the invention improves the cleaning result compared to the same composition without the enzyme present).

The detergent compositions of the invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent compositions of the invention may find use in hard surface cleaning, automatic dishwashing applications, as well as cosmetic applications such as dentures, teeth, hair and skin.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

Unless otherwise noted, all component or composition levels provided herein are made in reference to the active level of that component or composition, and are exclusive of impurities, for example, residual solvents or by-products, which may be present in commercially available sources.

The mannanase of the invention is normally incorporated in the detergent composition (pods/caps, liquid detergent or powder detergent) at a level of from 0.001% to 10% of enzyme protein by weight of the composition, such as 0.001% to 0.1%, 0.01% to 1.0% or 0.1% to 10% of enzyme protein by weight of the composition.

The mannanase of the invention is normally incorporated in the washing composition in such amounts that their concentration in the wash water is at a level of from 0.0001 to 1 ppm enzyme protein, such as 0.0001 to 0.01 ppm, such as 0.001 to 0.1 ppm or such as 0.01 to 1 ppm enzyme protein in wash water.

In some preferred embodiments, the detergent compositions provided herein are typically formulated such that, during use in aqueous cleaning operations, the wash water has a pH of from about 5.0 to about 11.5, or in alternative embodiments, even from about 6.0 to about 10.5, such as from about 5 to about 11, from about 5 to about 10, from about 5 to about 9, from about 5 to about 8, from about 5 to about 7, from about 6 to about 11, from about 6 to about 10, from about 6 to about 9, from about 6 to about 8, from about 6 to about 7, from about 7 to about 11, from about 7 to about 10, from about 7 to about 9, or from about 7 to about 8. In some preferred embodiments, granular or liquid laundry products are formulated such that the wash water has a pH from about 5.5 to about 8. Techniques for controlling pH at recommended usage levels include the use of buffers, alkalis, acids, etc., and are well known to those skilled in the art.

Enzyme components weights are based on total protein. All percentages and ratios are calculated by weight unless otherwise indicated. All percentages and ratios are calculated based on the total composition unless otherwise indicated. In the exemplified detergent composition, the enzymes levels are expressed by pure enzyme by weight of the total composition and unless otherwise specified, the detergent ingredients are expressed by weight of the total composition.

The enzymes of the present invention also find use in detergent additive products. A detergent additive product comprising a mannanase of the invention is ideally suited for inclusion in a wash process when, e.g., temperature is low, such as at temperatures about 40° C. or below, the pH is between 6 and 8 and the washing time short, e.g., below 30 min.

The detergent additive product may be a mannanase of the invention and preferably an additional enzyme. In one embodiment, the additive is packaged in dosage form for addition to a cleaning process. The single dosage may comprise a pill, tablet, gelcap or other single dosage unit including powders and/or liquids. In some embodiments, filler and/or carrier material(s) are included, suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol.

In one particularly preferred embodiment the mannanase according to the invention is employed in a granular composition or liquid, the mannanase may be in form of an encapsulated particle. In one embodiment, the encapsulating material is selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof.

The compositions according to the invention typically comprise one or more detergent ingredients. The term detergent compositions include articles and cleaning and treatment compositions. The term cleaning composition includes, unless otherwise indicated, tablet, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use. The composition can also be in unit dose packages, including those known in the art and those that are water soluble, water insoluble and/or water permeable.

In embodiments in which cleaning and/or detergent components may not be compatible with the mannanase of the present invention, suitable methods may be used for keeping the cleaning and/or detergent components and the mannanase separated (i.e., not in contact with each other) until combination of the two components is appropriate. Such separation methods include any suitable method known in the art (e.g., gelcaps, encapsulation, tablets, and physical separation e.g., by use of a water dissolvable pouch having one or more compartments).

In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). The enzymes of the detergent compositions of the invention may also be stabilized using conventional stabilizing agents such as polyol, e.g., propylene glycol or glycerol, a sugar or sugar alcohol, lactic acid, and the composition may be formulated as described in, e.g., WO 92/19709 and WO 92/19708. The enzymes of the invention may also be stabilized by adding reversible enzyme inhibitors, e.g., of the protein type (as described in EP 544 777) or the boronic acid type. Other enzyme stabilizers are well known in the art, such as peptide aldehydes and protein hydrolysate, e.g. the mannanases according to the invention may be stabilized using peptide aldehydes or ketones such as described in WO2005/105826 and WO2009/118375.

Protected enzymes for inclusion in a detergent composition of the invention may be prepared, as mentioned above, according to the method disclosed in EP 238 216.

The composition may be augmented with one or more agents for preventing or removing the formation of the biofilm. These agents may include, but are not limited to, dispersants, surfactants, detergents, other enzymes, antimicrobials, and biocides.

The compositions of the invention may be applied in dosing elements to be used in an auto-dosing device. The dosing elements comprising the composition of the present invention can be placed into a delivery cartridge as that described in WO 2007/052004 and WO 2007/0833141. The dosing elements can have an elongated shape and set into an array forming a delivery cartridge which is the refill for an auto-dosing dispensing device as described in case WO 2007/051989. The delivery cartridge is to be placed in an auto-dosing delivery device, such as that described in WO 2008/053191.

Suitable disclosure of auto-dosing devices can be found in WO 2007/083139, WO 2007/051989, WO 2007/083141, WO 2007/083142 and EP2361964, Formulation of the Mannanase in Granules Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The mannanase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the www.ip.com disclosure IPCOM000200739D.

Another example of formulation of enzymes by the use of co-granulates is disclosed in WO 2013/188331, which relates to a detergent composition comprising (a) a multi-enzyme co-granule; (b) less than 10% w/w zeolite (anhydrous basis); and (c) less than 10% w/w phosphate salt (anhydrous basis), wherein said enzyme co-granule comprises from 10 to 98% w/w moisture sink component and the composition additionally comprises from 20 to 80% w/w detergent moisture sink component.

An embodiment of the invention relates to an enzyme granule/particle comprising the mannanase of the invention. The granule is composed of a core, and optionally one or more coatings (outer layers) surrounding the core.

Typically the granule/particle size, measured as equivalent spherical diameter (volume based average particle size), of the granule is 20-2000 μm, particularly 50-1500 μm, 100-1500 μm or 250-1200 μm.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include binders, such as synthetic polymer, wax, fat, or carbohydrate.

The core may comprise a salt of a multivalent cation, a reducing agent, an antioxidant, a peroxide decomposing catalyst and/or an acidic buffer component, typically as a homogenous blend.

The core may consist of an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); *Powdered detergents*; Surfactant Science Series; 1998; vol. 71; page 140-142; Marcel Dekker).

b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606 c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme (see also Michael S. Showell (editor); *Powdered detergents*; Surfactant Science Series; 1998; vol. 71; page 140-142; Marcel Dekker).

e) Prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique f) Mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons).

h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them and form a granule.

i) The cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In a particular embodiment the thickness of the coating is below 100 µm. In a more particular embodiment the thickness of the coating is below 60 µm. In an even more particular embodiment the total thickness of the coating is below 40 µm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 µm, such as less than 10 µm or less than 5 µm.

The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{20°\ C.}$=92%), $NH_4Cl$ ($CH_{20°\ C.}$=79.5%), $(NH_4)_2HPO_4$. ($CH_{20°\ C.}$=93.0%), $NH_4H_2PO_4$. ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$. ($CH_{20°\ C.}$=96.5%), $KNO_3$ ($CH_{20°\ C.}$=93.5%), $Na_2SO_4$ ($CH_{20°\ C.}$=90%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$, ($CH_{20°\ C.}$=90%) and sodium citrate ($CH_{20°\ C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

Thus, in a further aspect, the present invention provides a granule, which comprises:

(a) a core comprising a mannanase according to the invention, and (b) optionally a coating consisting of one or more layer(s) surrounding the core.

Other Enzymes

In one embodiment, a mannanase of the invention is combined with one or more enzymes, such as at least two enzymes, more preferred at least three, four or five enzymes. Preferably, the enzymes have different substrate specificity, e.g., proteolytic activity, amylolytic activity, lipolytic activity, hemicellulytic activity or pectolytic activity.

The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of animal, vegetable or microbial origin. Particularly suitable cellulases include those of bacterial or fungal origin. Chemically modified or protein engineered variants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 1999/001544.

Commercially available cellulases include Celluzyme™, and Carezyme™ (Novozymes NS), Clazinase™, and Puradax HA™ (Genencor International Inc.), and KAC-500 (B)™ (Kao Corporation).

Proteases: Suitable proteases include those of bacterial, fungal, plant, viral or animal origin e.g. microbial or vegetable origin. Microbial origin is preferred. Chemically modified or protein engineered variants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellulomonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases: Suitable lipases include those of animal, vegetable or microbial origin. Particularly suitable lipases include those of bacterial or fungal origin. Chemically modified or protein engineered variants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™, and Lipex™ (Novozymes A/S).

Amylases: Suitable amylases which can be used together with mannanase of the invention may be an alpha-amylase or a glucoamylase and may be of bacterial or fungal origin. Chemically modified or protein engineered variants are included. Amylases include, for example, alpha-amylases obtained from *Bacillus*, e.g., a special strain of *Bacillus licheniformis*, described in more detail in GB 1,296,839. Suitable amylases include amylases having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476. Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+ G475K;

S125A+N128C+K178L+T182G+Y305R+G475K; or

S125A+N128C+T131I+T165I+K178L+T182G+Y305R+ G475K wherein the variants are C-terminally truncated and optionally further comprises a substitution at position 243 and/or a deletion at position 180 and/or position 181. Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO2011/098531, WO2013/001078 and WO2013/001087. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases: Suitable peroxidases/oxidases include those of plant, bacterial or fungal origin. Chemically modified or protein engineered variants are included. Examples of useful peroxidases include peroxidases from *Coprinus*, e.g., from *C. cinereus*, and variants thereof as those described in WO 93/24618, WO 95/10602, and WO 98/15257.

Lechinases/Beta-glucanases: Suitable Lechinases include those of bacterial or fungal origin. They may be chemically modified or protein engineered. Examples of useful beta-glucanases include those described in WO 2015/144824 (Novozymes A/S) and WO 99/06516 (Henkel KGAA).

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates as described above, liquids, in particular stabilized liquids, or slurries.

Surfactants

Typically, the detergent composition comprises (by weight of the composition) one or more surfactants in the range of 0% to 50%, preferably from 2% to 40%, more preferably from 5% to 35%, more preferably from 7% to 30%, most preferably from 10% to 25%, even most preferably from 15% to 20%. In a preferred embodiment the detergent is a liquid or powder detergent comprising less than 40%, preferably less than 30%, more preferably less than 25%, even more preferably less than 20% by weight of surfactant. The composition may comprise from 1% to 15%, preferably from 2% to 12%, 3% to 10%, most preferably from 4% to 8%, even most preferably from 4% to 6% of one or more surfactants. Preferred surfactants are anionic surfactants, non-ionic surfactants, cationic surfactants, zwitterionic surfactants, amphoteric surfactants, and mixtures thereof. Preferably, the major part of the surfactant is anionic. Suitable anionic surfactants are well known in the art and may comprise fatty acid carboxylates (soap), branched-chain, linear-chain and random chain alkyl sulfates or fatty alcohol sulfates or primary alcohol sulfates or alkyl benzenesulfonates such as LAS and LAB or phenyl-alknesulfonates or alkenyl sulfonates or alkenyl benzenesulfonates or alkyl ethoxysulfates or fatty alcohol ether sulfates or alpha-olefin sulfonate or dodecenyl/tetradecnylsuccinic acid. The anionic surfactants may be alkoxylated. The detergent composition may also comprise from 1 wt % to 10 wt % of non-ionic surfactant, preferably from 2 wt % to 8 wt %, more preferably from 3 wt % to 7 wt %, even more preferably less than 5 wt % of non-ionic surfactant. Suitable non-ionic surfactants are well known in the art and may comprise alcohol ethoxylates, and/or alkyl ethoxylates, and/or alkylphenol ethoxylates, and/or glucamides such as fatty acid N-glucosyl N-methyl amides, and/or alkyl polyglucosides and/or mono- or diethanolamides or fatty acid amides. The detergent composition may also comprise from 0 wt % to 10 wt % of cationic surfactant, preferably from 0.1 wt % to 8 wt %, more preferably from 0.5 wt % to 7 wt %, even more preferably less than 5 wt % of cationic surfactant. Suitable cationic surfactants are well known in the art and may comprise alkyl quaternary ammonium compounds, and/or alkyl pyridinium compounds and/or alkyl quaternary phosphonium compounds and/or alkyl ternary sulphonium compounds. The composition preferably comprises surfactant in an amount to provide from 100 ppm to 5,000 ppm surfactant in the wash liquor during the laundering process. The composition upon contact with water typically forms a wash liquor comprising from 0.5 g/l to 10 g/l detergent composition. Many suitable surface active compounds are available and fully described in the literature, for example, in "Surface-Active Agents and Detergents", Volumes I and 11, by Schwartz, Perry and Berch.

Builders

The main role of builder is to sequester divalent metal ions (such as calcium and magnesium ions) from the wash solution that would otherwise interact negatively with the surfactant system. Builders are also effective at removing metal ions and inorganic soils from the fabric surface, leading to improved removal of particulate and beverage stains. Builders are also a source of alkalinity and buffer the pH of the wash water to a level of 9.5 to 11. The buffering capacity is also termed reserve alkalinity, and should preferably be greater than 4.

The detergent compositions of the present invention may comprise one or more detergent builders or builder systems. Many suitable builder systems are described in the literature, for example in Powdered Detergents, Surfactant science series volume 71, Marcel Dekker, Inc. Builder may comprise from 0% to 60%, preferably from 5% to 45%, more preferably from 10% to 40%, most preferably from 15% to 35%, even more preferably from 20% to 30% builder by weight of the subject composition. The composition may comprise from 0% to 15%, preferably from 1% to 12%, 2% to 10%, most preferably from 3% to 8%, even most preferably from 4% to 6% of builder by weight of the subject composition.

Builders include, but are not limited to, the alkali metal, ammonium and alkanolammonium salts of polyphosphates (e.g., tripolyphosphate STPP), alkali metal silicates, alkaline earth and alkali metal carbonates, aluminosilicate builders (e.g., zeolite) and polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Ethanole amines (MEA, DEA, and TEA) may also contribute to the buffering capacity in liquid detergents.

Bleaches

The detergent compositions of the present invention may comprise one or more bleaching agents. In particular powdered detergents may comprise one or more bleaching agents. Suitable bleaching agents include other photobleaches, pre-formed peracids, sources of hydrogen peroxide, bleach activators, hydrogen peroxide, bleach catalysts and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) other photobleaches for example Vitamin K3;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include inorganic salts such as alkali metal silicate, carbonate or borate salts or mixtures thereof, or organic materials such as water-soluble or dispersible polymers, waxes, oils or fatty soaps. Useful bleaching compositions are described in U.S. Pat. Nos. 5,576,282, and 6,306,812;

(4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof; and (5) bleach catalysts that are capable of accepting an oxygen atom from peroxyacid and transferring the oxygen atom to an oxidizable substrate are described in WO 2008/007319. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof. The bleach catalyst will typically be comprised in the detergent composition at a level of from 0.0005% to 0.2%, from 0.001% to 0.1%, or even from 0.005% to 0.05% by weight.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Adjunct Materials

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate.

Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Fabric hueing agents—The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1 876 226. The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series, volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523. Furthermore random graft co-polymers are suitable soil release polymers Suitable graft co-polymers are described in more detail in WO 2007/138054, WO 2006/108856 and WO 2006/113314. Other soil release polymers are substituted polysaccharide structures especially substituted cellulosic structures such as modified cellulose deriviatives such as those described in EP 1 867 808 or WO 2003/040279. Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

In one aspect the detergent is a compact fluid laundry detergent composition comprising: a) at least about 10%, preferably from 20 to 80% by weight of the composition, of surfactant selected from anionic surfactants, non ionic surfactants, soap and mixtures thereof; b) from about 1% to about 30%, preferably from 5 to 30%, by weight of the composition, of water; c) from about 1% to about 15%, preferably from 3 to 10% by weight of the composition, of non-aminofunctional solvent; and d) from about 5% to about 20%, by weight of the composition, of a performance additive selected from chelants, soil release polymers, enzymes and mixtures thereof; wherein the compact fluid laundry detergent composition comprises at least one of: (i) the surfactant has a weight ratio of the anionic surfactant to the nonionic surfactant from about 1.5:1 to about 5:1, the surfactant comprises from about 15% to about 40%, by weight of the composition, of anionic surfactant and comprises from about 5% to about 40%, by weight of the composition, of the soap; (ii) from about 0.1% to about 10%, by weight of the composition, of a suds boosting agent selected from suds boosting polymers, cationic surfactants, zwitterionic surfactants, amine oxide surfactants, amphoteric surfactants, and mixtures thereof; and (ii) both (i) and (ii). All the ingredients are described in WO 2007/130562. Further polymers useful in detergent formulations are described in WO 2007/149806.

In another aspect the detergent is a compact granular (powdered) detergent comprising a) at least about 10%, preferably from 15 to 60% by weight of the composition, of surfactant selected from anionic surfactants, non-ionic surfactants, soap and mixtures thereof; b) from about 10 to 80% by weight of the composition, of a builder, preferably from 20% to 60% where the builder may be a mixture of builders selected from i) phosphate builder, preferably less than 20%, more preferably less than 10% even more preferably less than 5% of the total builder is a phosphate builder; ii) a zeolite builder, preferably less than 20%, more preferably less than 10% even more preferably less than 5% of the total builder is a zeolite builder; iii) citrate, preferably 0 to 5% of the total builder is a citrate builder; iv) polycarboxylate, preferably 0 to 5% of the total builder is a polycarboxylate builder v) carbonate, preferably 0 to 30% of the total builder is a carbonate builder and vi) sodium silicates, preferably 0 to 20% of the total builder is a sodium silicate builder; c)

from about 0% to 25% by weight of the composition, of fillers such as sulphate salts, preferably from 1% to 15%, more preferably from 2% to 10%, more preferably from 3% to 5% by weight of the composition, of fillers; and d) from about 0.1% to 20% by weight of the composition, of enzymes, preferably from 1% to 15%, more preferably from 2% to 10% by weight of the composition, of enzymes.

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In a preferred aspect of the present invention the mannanase of the invention may be combined with at least two enzymes. These additional enzymes are described in details in the section "other enzymes", more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a mannanase of the invention with another stain removing enzyme, e.g., a mannanase of the invention and a protease, a mannanase of the invention and a serine protease, a mannanase of the invention and an amylase, a mannanase of the invention and a cellulase, mannanase of the invention and a lipase, a mannanase of the invention and a cutinase, a mannanase of the invention and a pectinase or a mannanase of the invention and an anti-redeposition enzyme. More preferably, the mannanase of the invention is combined with at least two other stain removing enzymes, e.g., a mannanase of the invention, a lipase and an amylase; or a mannanase of the invention, a protease and an amylase; or a mannanase of the invention, a protease and a lipase; or a mannanase of the invention, a protease and a pectinase; or a mannanase of the invention, a protease and a cellulase; or a mannanase of the invention, a protease and a hemicellulase; or a mannanase of the invention, a protease and a cutinase; or a mannanase of the invention, an amylase and a pectinase; or a mannanase of the invention, an amylase and a cutinase; or a mannanase of the invention, an amylase and a cellulase; or a mannanase of the invention, an amylase and a hemicellulase; or a mannanase of the invention, a lipase and a pectinase; or a mannanase of the invention, a lipase and a cutinase; or a mannanase of the invention, a lipase and a cellulase; or a mannanase of the invention, a lipase and a hemicellulase. Even more preferably, a mannanase of the invention may be combined with at least three other stain removing enzymes, e.g., a mannanase of the invention, a protease, a lipase and an amylase; or a mannanase of the invention, a protease, an amylase and a pectinase; or a mannanase of the invention, a protease, an amylase and a cutinase; or a mannanase of the invention, a protease, an amylase and a cellulase; or a mannanase of the invention, a protease, an amylase and a hemicellulase; or a mannanase of the invention, an amylase, a lipase and a pectinase; or a mannanase of the invention, an amylase, a lipase and a cutinase; or a mannanase of the invention, an amylase, a lipase and a cellulase; or a mannanase of the invention, an amylase, a lipase and a hemicellulase; or a mannanase of the invention, a protease, a lipase and a pectinase; or a mannanase of the invention, a protease, a lipase and a cutinase; or a mannanase of the invention, a protease, a lipase and a cellulase; or a mannanase of the invention, a protease, a lipase and a hemicellulase. A mannanase according to the present invention may be combined with any of the enzymes selected from the non-exhaustive list comprising: carbohydrases, such as an amylase, a hemicellulase, a pectinase, a cellulase, a xanthanase or a pullulanase, a peptidase, a protease or a lipase.

In a preferred embodiment, a mannanase of the invention is combined with a serine protease, e.g., an S8 family protease such as Savinase®.

In another embodiment of the present invention, a mannanase of the invention may be combined with one or more metalloproteases, such as an M4 metalloprotease, including Neutrase® or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one mannanase of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

Typical detergent compositions include various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions from the liquid.

In a particular embodiment, the invention concerns the use of a composition comprising a mannanase of the invention, wherein said enzyme composition further comprises at least one or more of the following a surfactant, a builder, a chelator or chelating agent, bleach system or bleach component in laundry or dish wash.

In a preferred embodiment of the invention the amount of a surfactant, a builder, a chelator or chelating agent, bleach system and/or bleach component are reduced compared to amount of surfactant, builder, chelator or chelating agent, bleach system and/or bleach component used without the added mannanase of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of mannanase of the invention, such as a conventional amount of such component. In one aspect, the mannanase of the invention is used in detergent compositions wherein said composition is free of at least one component which is a surfactant, a builder, a chelator or chelating agent, bleach system or bleach component and/or polymer.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 8. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising a mannanase of the invention.

A preferred embodiment concerns a method of cleaning, said method comprising the steps of: contacting an object with a cleaning composition comprising a mannanase of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a mannanase of the invention under conditions suitable for cleaning said object.

Low Temperature Uses

One embodiment of the invention concerns a method of doing laundry, dish wash or industrial cleaning comprising contacting a surface to be cleaned with a mannanase of the invention, and wherein said laundry, dish wash, industrial or institutional cleaning is performed at a temperature of about 40° C. or below. One embodiment of the invention relates to the use of a mannanase in laundry, dish wash or a cleaning process wherein the temperature in laundry, dish wash, industrial cleaning is about 40° C. or below In another embodiment, the invention concerns the use of a mannanase according to the invention in a protein removing process, wherein the temperature in the protein removing process is about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In particular preferred embodiments the wash temperature is about 20° C., about 30° C., or about 40° C.

Animal Feed and Animal Feed Additives

The present invention also relates to animal feed and animal feed additives comprising the mannanase of the invention.

In one aspect, the animal feed or animal feed additive comprises the polypeptide of aspect one or two and one or more components selected from the list consisting of vitamins, minerals and amino acids.

In one aspect, the animal feed or animal feed additive comprises the granule of aspect five or six and one or more components selected from the list consisting of vitamins, minerals and amino acids.

In one aspect, the animal feed or animal feed additive comprises the liquid formulation of aspect seven or eight and one or more components selected from the list consisting of vitamins, minerals and amino acids.

In an embodiment, the animal feed or animal feed additive further comprises one or more additional enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In an embodiment, the animal feed or animal feed additive comprises one or more microbes selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

Uses

The mannanases of the invention may be used in applications where mannan needs to be degraded. Examples of where mannanases could be used are in the production of bioethanol from softwood and palm kernel press cake, for the improvement of animal feed and in the hydrolysis of coffee. Furthermore, guar gum is used in many food products and in the oil and gas industry, so the mannanases of the invention could be used in detergents to remove mannan containing stains, for hydraulic fracturing to create subterranean fractures that extend from the borehole into rock formation in order to increase the rate at which fluids can be produced by the formation or for cleaning borehole filtercake. The mannan may thus be used in fracturing of a subterranean formation perpetrated by a well bore or the mannan may be used as a component in borehole filtercake.

In one aspect, the polypeptide of aspect one or two, detergent composition of aspect three or four, granule of aspect five or six or liquid formulation of aspect seven or eight may be used for degrading mannan, such as linear mannan, galactomannan, glucomannan and galactoglucomannan. In one aspect, the polypeptide of aspect one or two, detergent composition of aspect three or four, granule of aspect five or six or liquid formulation of aspect seven or eight may be used in a process for degrading mannan, such as linear mannan, galactomannan, glucomannan and galactoglucomannan.

In one aspect, the polypeptide of aspect one or two, detergent composition of aspect three or four, granule of aspect five or six or liquid formulation of aspect seven or eight may be used for controlling the viscosity of drilling fluids. In one aspect, the polypeptide of aspect one or two, detergent composition of aspect three or four, granule of aspect five or six or liquid formulation of aspect seven or eight may be used in fracturing of a subterranean formation perpetrated by a well bore.

The mannanases of the invention may be used for preventing, reducing or removing malodor from an item. Thus in one embodiment, the polypeptide of aspect one or two, detergent composition of aspect three or four, granule of aspect five or six or liquid formulation of aspect seven or eight may be used for preventing, reducing or removing malodor from an item.

Use of Mannanases of the Invention in Preventing, Reducing or Removing a Biofilm Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore, the biofilm adhere soil due to the sticky nature of the biofilm. The commercial laundry detergent compositions available on the marked do not remove such adhered microorganisms or biofilm.

The present invention concerns the use of the polypeptide of aspect one or two, detergent composition of aspect three or four, granule of aspect five or six or liquid formulation of aspect seven or eight for preventing, reducing or removing a biofilm from an item, wherein the polypeptide is obtained from a fungal source and wherein the item is a textile. In one embodiment, the polypeptide of aspect one or two, detergent composition of aspect three or four, granule of aspect five or six or liquid formulation of aspect seven or eight is used for preventing, reducing or removing the stickiness of an item.

Use of Mannanases of the Invention in Food Processing and Animal Feed

Several anti-nutritional factors can limit the use of specific plant material in the preparation of animal feed and food for humans. For example, plant material containing oligomannans such as mannan, galactomannan, glucomannan and galactoglucomannan can reduce the digestibility and absorption of nutritional compounds such as minerals, vitamins, sugars and fats by the animals. The negative effects are in particular due to the high viscosity of the mannan-containing polymers and to the ability of the mannan-containing polymers to adsorb nutritional compounds. These effects are reduced using mannan-containing polymers degrading enzymes, namely endo-beta-mannanase enzymes such as the mannanases described herein, which permit a higher proportion of mannan-containing polymers containing cheap plant material to be included in the feed resulting in a reduction of feed costs. Additionally, through the activity of the mannanases of the invention, mannan-containing polymers are broken down to simpler sugars, which can be more readily assimilated to provide additional energy. Accordingly, the invention further relates to using the mannanases of the invention for processing and/or manufacturing of food or animal feed.

Accordingly, the present invention relates to an animal feed composition and/or animal feed additive composition and/or pet food comprising a mannanase of the invention.

The present invention further relates to a method for preparing such animal feed composition and/or animal feed additive composition and/or pet food comprising mixing the mannanase of the invention with one or more animal feed ingredients and/or animal feed additive ingredients and/or pet food ingredients.

Furthermore, the present invention relates to the use of the mannanase of the invention in the preparation of an animal feed composition and/or animal feed additive composition and/or pet food.

Use of Mannanases of the Invention for Degrading a Cellulosic Material and/or Producing a Fermentation Product The mannan may be used for degrading a cellulosic material, for producing a fermentation product and for fermenting a cellulosic material e.g., in a process for producing a fermentation product, comprising: (a) saccharifying a cellulosic material with an enzyme composition, wherein the enzyme composition comprises the polypeptide of aspect one or two, granule of aspect five or six or liquid formulation of aspect seven or eight; (b) fermenting the saccharified cellulosic material with one or more fermenting microorganisms to produce the fermentation product; and (c) recovering the fermentation product from the fermentation. The cellulosic material may be pretreated before saccharification. In one embodiment, the enzyme composition comprises one or more enzymes selected from the group consisting of cellulase, AA9 polypeptide, hemicellulase, esterase, expansin, ligninolytic enzyme, oxidoreductase, pectinase, protease, and swollenin.

In another embodiment, the invention relates to a process of fermenting a cellulosic material, comprising: fermenting the cellulosic material with one or more fermenting microorganisms, wherein the cellulosic material is saccharified with an enzyme composition comprising the polypeptide of aspect one or two, granule of aspect five or six or liquid formulation of aspect seven or eight. The cellulosic material may be pretreated before saccharification. In one embodiment, the enzyme composition comprises one or more enzymes selected from the group consisting of cellulase, AA9 polypeptide, hemicellulase, esterase, expansin, ligninolytic enzyme, oxidoreductase, pectinase, protease, and swollenin.

Use of Mannanases of the Invention for Fermented Beverages

In one aspect, the invention relates to a method of preparing a fermented beverage, such as beer or wine, comprising mixing the polypeptide of aspect one or two, granule of aspect five or six or liquid formulation of aspect seven or eight with malt and/or adjunct.

Another aspect concerns a method of providing a fermented beverage comprising the step of contacting a mash and/or a wort with the polypeptide of aspect one or two, the granule of aspect five or six or the liquid formulation of aspect seven or eight.

In the context of the present invention, the term "fermented beverage" is meant to comprise any beverage such as wine or beer produced by a method comprising a fermentation process, such as a microbial, bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like may be used as a source of starch.

As used herein, the term "mash" refers to an aqueous slurry of any starch and/or sugar containing plant material such as grist, e. g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

Use of Mannanases of the Invention for Treating Coffee Extracts

The mannanase of the invention may also be used for hydrolyzing galactomannans present in liquid coffee extracts. In certain preferred embodiments, the mannanase of the invention is used to inhibit gel formation during freeze drying of liquid coffee extracts. The decreased viscosity of the extract reduces the energy consumption during drying. In certain other preferred embodiments, the mannanase of the invention is applied in an immobilized form in order to reduce enzyme consumption and avoid contamination of the coffee extract. This use is further disclosed in EP 676 145.

In general terms the coffee extract is incubated in the presence of an isolated mannanase of the invention or fragment or variant thereof under conditions suitable for hydrolyzing galactomannans present in liquid coffee extract.

Thus in one embodiment, then invention relates to a process for producing a coffee extract, comprising the steps:
(a) providing roast and ground coffee beans;
(b) adding to said coffee beans water and the polypeptide of aspect one or two, granule of aspect five or six or liquid formulation of aspect seven or eight;
(c) incubating to make an aqueous coffee extract; and
(d) separating the coffee extract from the extracted coffee beans.

Use of Mannanase of the Invention in Bakery Food Products

In another aspect, the invention relates to a method of preparing baked products comprising adding the polypeptide of aspect one or two, granule of aspect five or six or liquid formulation of aspect seven or eight to a dough, followed by baking the dough.

Examples of baked products are well known to those skilled in the art and include breads, rolls, puff pastries, sweet fermented doughs, buns, cakes, crackers, cookies, biscuits, waffles, wafers, tortillas, breakfast cereals, extruded products, and the like.

The mannanase of the invention may be added to dough as part of a bread improver composition. Bread improvers are compositions containing a variety of ingredients, which improve dough properties and the quality of bakery products, e.g. bread and cakes. Bread improvers are often added in industrial bakery processes because of their beneficial effects e.g. the dough stability and the bread texture and volume. Bread improvers usually contain fats and oils as well as additives like emulsifiers, enzymes, antioxidants, oxidants, stabilizers and reducing agents. In addition to the mannanase of the invention, other enzymes which may also be present in the bread improver including amylases, hemicellulases, amylolytic complexes, lipases, proteases, xylanases, pectinases, pullulanases, non-starch polysaccharide degrading enzymes and redox enzymes like glucose oxidase, lipoxygenase or ascorbic acid oxidase.

In one aspect, the mannanase of the invention may be added to dough as part of a bread improver composition which also comprises a glucomannan and/or galactomannan source such as konjac gum, guar gum, locust bean gum (*Ceratonia siliqua*), copra meal, ivory nut mannan (*Phyteleohas macrocarpa*), seaweed mannan extract, coconut meal, and the cell wall of brewers yeast (may be dried, or used in the form of brewers yeast extract).

A further aspect of the invention relates to the use of the mannanase of the invention in dough to improve dough tolerance, flexibility and stickiness. Preferably the dough to which the mannanase of the invention may be added is not a pure wheat flour dough, but comprises bran or oat, rice, millet, maize, or legume flour in addition to or instead of pure wheat flour.

A yet further aspect of the invention relates to the use of any of the mannanase of the invention in dough to improve the crumb structure and retard staling in the final baked product, such as bread.

Use of Mannanase of the Invention for Use in Dairy Food Products

In one aspect of the current invention, the mannanase of the invention may be added to milk or any other dairy product to which has also been added a glucomannan and/or galactomannan. Typical glucomannan and/or galactomannan sources are listed above in the bakery aspects, and include guar or konjac gum. The combination of the mannanase of the invention with a glucomannan and/or galactomannan releases mannanase hydrolysates (mannooligosaccharides) which act as soluble prebiotics by promoting the selective growth and proliferation of probiotic bacteria (especially Bifidobacteria and *Lactobacillus* lactic acid bacteria) commonly associated with good health when found at favourable population densities in the large intestine or colon.

In one aspect, the invention relates to a method of preparing milk or dairy products comprising adding to the milk or dairy product (a) glucomannan, galactomannan and/or galactoglucomannan and (b) the polypeptide of aspect one or two, granule of aspect five or six or liquid formulation of aspect seven or eight.

In one aspect of the invention the mannanase of the invention is used in combination with any glucomannan or galactomannan prior to or following addition to a dairy based foodstuff to produce a dairy based foodstuff comprising prebiotic mannan hydrolysates. In a further aspect of the invention the thus produced mannooligosacharide-containing dairy product is capable of increasing the population of beneficial human intestinal microflora, and in a yet further aspect of the current invention the dairy based foodstuff may comprise the mannanase of the invention together with any source of glucomannan and/or galactomannan and/or galactoglucomannan, and a dose sufficient for inoculation of at least one strain of bacteria (such as Bifidobacteria or *Lactobacillus*) known to be of benefit in the human large intestine. Preferably said dairy-based foodstuff is a yoghurt or milk drink.

Use of Mannanase of the Invention for Paper Pulp Bleaching

The mannanase of the invention may further be used in the enzyme aided bleaching of paper pulps such as chemical pulps, semi-chemical pulps, kraft pulps, mechanical pulps or pulps prepared by the sulfite method. Thus, the invention relates to a method of bleaching paper pulps comprising incubating the paper pulp with the polypeptide of aspect one or two, detergent composition of aspect three or four, granule of aspect five or six or liquid formulation of aspect seven or eight.

In some embodiments, the pulps are chlorine free pulps bleached with oxygen, ozone, peroxide or peroxyacids. In some embodiments, the mannanase of the invention is used in enzyme aided bleaching of pulps produced by modified or continuous pulping methods that exhibit low lignin contents. In some other embodiments, the mannanase of the invention is applied alone or preferably in combination with xylanase and/or endoglucanase and/or alpha-galactosidase and/or cellobiohydrolase enzymes.

The invention is further summarized in the below paragraphs:

1. A polypeptide having mannanase activity, selected from the group consisting of:
   (a) a polypeptide having at least 91%, e.g., at least 92%, at least 93%, at least 94%, at least 95%, at least 96%, at least 97%, at least 98%, at least 99%, or 100% sequence identity to SEQ ID NO: 4;
   (b) a variant of SEQ ID NO: 4, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions;
   (c) a polypeptide comprising the polypeptide of (a) or (b) and a N-terminal and/or C-terminal His-tag and/or HQ-tag;
   (d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and
   (e) a fragment of the polypeptide of (a) or (b) having mannanase activity and having at least 90% of the length of the mature polypeptide.

2. The polypeptide of item 1, wherein the polypeptide further comprises a carbohydrate binding module (CBM).

3. The polypeptide of item 2, wherein the carbohydrate binding module is a family 35 CBM.

4. The polypeptide of any of items 2 to 3, wherein the polypeptide has at least 87%, e.g., at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13.

5. The polypeptide of item 1, comprising or consisting of amino acids 1 to 312 of SEQ ID NO: 4, the mature polypeptide of SEQ ID NO: 2 or amino acids 1 to 491 of SEQ ID NO: 3, the mature polypeptide of SEQ ID NO: 12 or amino acids 1 to 491 of SEQ ID NO: 13.

6. A polypeptide having mannanase activity, selected from the group consisting of:
   (a) a polypeptide having at least 87%, e.g., at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13;
(b) a polypeptide encoded by a polynucleotide having at least 87%, e.g., at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 11;
(c) a variant of SEQ ID NO: 3 or SEQ ID NO: 13, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(d) a polypeptide comprising the polypeptide of (a), (b) or (c) and a N-terminal and/or C-terminal His-tag and/or HQ-tag;
(e) a polypeptide comprising the polypeptide of (a), (b) or (c) and a N-terminal and/or C-terminal extension of up to 10 amino acids, e.g. 1, 2, 3, 4, 5, 6, 7, 8, 9 or 10 amino acids; and
(f) a fragment of the polypeptide of (a), (b) or (c) having mannanase activity and having at least 90% of the length of the mature polypeptide.

7. The polypeptide of item 6, comprising or consisting of the mature polypeptide of SEQ ID NO: 2 or amino acids 1 to 491 of SEQ ID NO: 3, or the mature polypeptide of SEQ ID NO: 12 or amino acids 1 to 491 of SEQ ID NO: 13.

8. A composition comprising the polypeptide of any of items 1 to 7.

9. The composition comprising the polypeptide of any of items 1 to 7 and one or more components selected from the group consisting of surfactants, hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants and solubilizers.

10. The composition of any of items 8 to 9 further comprising one or more additional enzymes.

11. The composition of item 19, wherein the additional enzyme is selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases and transglutaminases, or any combinations thereof.

12. A detergent composition comprising a surfactant and a polypeptide having mannanase activity, wherein the polypeptide is selected from the group consisting of:
(a) a polypeptide having at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 4;
(b) a variant of SEQ ID NO: 4, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a polypeptide comprising the polypeptide of (a) or (b) and a N-terminal and/or C-terminal His-tag and/or HQ-tag;
(d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide.

13. The detergent composition of item 12, wherein the polypeptide further comprises a carbohydrate binding module (CBM).

14. The detergent composition of item 13, wherein the carbohydrate binding module is a family 35 CBM.

15. The detergent composition of any of items 13 to 14, wherein the polypeptide has at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13.

16. The detergent composition of item 12, comprising or consisting of amino acids 1 to 312 of SEQ ID NO: 4, the mature polypeptide of SEQ ID NO: 2 or amino acids 1 to 491 of SEQ ID NO: 3, the mature polypeptide of SEQ ID NO: 12 or amino acids 1 to 491 of SEQ ID NO: 13.

17. A detergent composition comprising a surfactant and a polypeptide having mannanase activity, wherein the polypeptide is selected from the group consisting of:
(a) a polypeptide having at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13;
(b) a polypeptide encoded by a polynucleotide having at least 81%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 11;
(c) a variant of SEQ ID NO: 3 or SEQ ID NO: 13, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(d) a polypeptide comprising the polypeptide of (a), (b) or (c) and a N-terminal and/or C-terminal His-tag and/or HQ-tag;
(e) a polypeptide comprising the polypeptide of (a), (b) or (c) and a N-terminal and/or C-terminal extension of up to 10 amino acids, e.g. 1, 2, 3, 4, 5, 6, 7, 8, 9 or 10 amino acids; and (f) a fragment of the polypeptide of (a), (b) or (c) having mannanase activity and having at least 90% of the length of the mature polypeptide.

18. The detergent composition of item 17, comprising or consisting of the mature polypeptide of SEQ ID NO: 2 or amino acids 1 to 491 of SEQ ID NO: 3, the mature polypeptide of SEQ ID NO: 12 or amino acids 1 to 491 of SEQ ID NO: 13.

19. The detergent composition of any of items 12 to 18 further comprising one or more components selected from the group consisting of hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants and solubilizers.

20. The detergent composition of any of items 18 to 19 further comprising one or more additional enzymes.

21. The detergent composition of item 20, wherein the additional enzyme is selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases and transglutaminases, or any combinations thereof.

22. A granule comprising a core particle and one or more coatings, wherein the granule comprises a polypeptide having mannanase activity selected from the group consisting of:
(a) a polypeptide having at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 4;
(b) a variant of SEQ ID NO: 4, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a polypeptide comprising the polypeptide of (a) or (b) and a N-terminal and/or C-terminal His-tag and/or HQ-tag;
(d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having mannanase activity and having at least 90% of the length of the mature polypeptide.

23. The granule of item 22, wherein the polypeptide further comprises a carbohydrate binding module (CBM).

24. The granule of item 23, wherein the carbohydrate binding module is a family 35 CBM.

25. The granule of any of items 23 to 24, wherein the polypeptide has at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13.

26. The granule of item 22, comprising or consisting of amino acids 1 to 312 of SEQ ID NO: 4, the mature polypeptide of SEQ ID NO: 2 or amino acids 1 to 491 of SEQ ID NO: 3, the mature polypeptide of SEQ ID NO: 12 or amino acids 1 to 491 of SEQ ID NO: 13.

27. A granule comprising a core particle and one or more coatings, wherein the granule comprises a polypeptide having mannanase activity selected from the group consisting of:
(a) a polypeptide having at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13;
(b) a polypeptide encoded by a polynucleotide having at least 81%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 11;
(c) a variant of SEQ ID NO: 3 or SEQ ID NO: 13, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(d) a polypeptide comprising the polypeptide of (a), (b) or (c) and a N-terminal and/or C-terminal His-tag and/or HQ-tag;
(e) a polypeptide comprising the polypeptide of (a), (b) or (c) and a N-terminal and/or C-terminal extension of up to 10 amino acids, e.g. 1, 2, 3, 4, 5, 6, 7, 8, 9 or 10 amino acids; and
(f) a fragment of the polypeptide of (a), (b) or (c) having mannanase activity and having at least 90% of the length of the mature polypeptide.

28. The granule of item 27, comprising or consisting of the mature polypeptide of SEQ ID NO: 2 or amino acids 1 to 491 of SEQ ID NO: 3, the mature polypeptide of SEQ ID NO: 12 or amino acids 1 to 491 of SEQ ID NO: 13.

29. The granule of any of items 22 to 28, wherein the coating comprises a salt and/or wax and/or flour.

30. The granule of any of items 22 to 29 further comprising one or more additional enzymes.

31. The granule of item 30, wherein the additional enzyme is selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases and transglutaminases, or any combinations thereof.

32. A liquid composition comprising a polyol and a polypeptide having mannanase activity, wherein the polypeptide is selected from the group consisting of:
   (a) a polypeptide having at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 4;
   (b) a variant of SEQ ID NO: 4, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (c) a polypeptide comprising the polypeptide of (a) or (b) and a N-terminal and/or C-terminal His-tag and/or HQ-tag;
   (d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and
   (e) a fragment of the polypeptide of (a) or (b) having mannanase activity and having at least 90% of the length of the mature polypeptide.
33. The liquid composition of item 32, wherein the polypeptide further comprises a carbohydrate binding module (CBM).
34. The liquid composition of item 33, wherein the carbohydrate binding module is a family 35 CBM.
35. The liquid composition of any of items 33 to 34, wherein the polypeptide has at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13.
36. The liquid composition of item 32, comprising or consisting of amino acids 1 to 312 of SEQ ID NO: 4, the mature polypeptide of SEQ ID NO: 2 or amino acids 1 to 491 of SEQ ID NO: 3, the mature polypeptide of SEQ ID NO: 12 or amino acids 1 to 491 of SEQ ID NO: 13.
37. A liquid composition comprising a polyol and a polypeptide having mannanase activity, wherein the polypeptide is selected from the group consisting of:
   (a) a polypeptide having at least 81%, e.g., at least 85%, at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 13;
   (b) a polypeptide encoded by a polynucleotide having at least 81%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 11;
   (c) a variant of SEQ ID NO: 3 or SEQ ID NO: 13, wherein the variant has mannanase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (d) a polypeptide comprising the polypeptide of (a), (b) or (c) and a N-terminal and/or C-terminal His-tag and/or HQ-tag;
   (e) a polypeptide comprising the polypeptide of (a), (b) or (c) and a N-terminal and/or C-terminal extension of up to 10 amino acids, e.g. 1, 2, 3, 4, 5, 6, 7, 8, 9 or 10 amino acids; and
   (f) a fragment of the polypeptide of (a), (b) or (c) having mannanase activity and having at least 90% of the length of the mature polypeptide.
38. The liquid composition of item 37, comprising or consisting of the mature polypeptide of SEQ ID NO: 2 or amino acids 1 to 491 of SEQ ID NO: 3, the mature polypeptide of SEQ ID NO: 12 or amino acids 1 to 491 of SEQ ID NO: 13.
39. The liquid formulation of any of item 32 to 38, wherein the polypeptide is dosed between 0.0001% to 10% w/w of liquid formulation.
40. The liquid formulation of any of items 32 to 39, wherein the polyol is dosed between 5% to 80% w/w of liquid formulation.
41. The liquid formulation of any of items 32 to 40, wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600 or any combination thereof.
42. The liquid formulation of any of items 32 to 41, wherein the formulation further comprises 0.001% to 2.0% w/w preservative.
43. The liquid formulation of item 42, wherein the preservative is selected from the group consisting of phenoxy ethanol, 1,2-benzisothiazolin-3(2H)-one, sodium sorbate, potassium sorbate, sodium benzoate, potassium benzoate, methylisothiazolinone, chloro methylisothiazolinone, methyl parabene, ethyl parabene, propyl parabene, butyl parabene, quarterary ammonium salts (such as BAC/ADBAC; alkylbenzyl quarternary ammonium chloride, dioctyldimethylammonium chloride, didecyldimethylammonium chloride, cetrimonium chloride), essential oils and organic acids or any combination thereof.
44. The liquid composition of any of items 32 to 43 further comprising one or more additional enzymes.
45. The liquid composition of item 44, wherein the additional enzyme is selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases and transglutaminases, or any combinations thereof.
46. An animal feed or animal feed additive comprising the polypeptide of any of items 1 to 7, the composition of any of items 8 to 11, the granule of any of items 22 to 31 or the liquid composition of any of items 32 to 45 and one or more components selected from the list consisting of:
   one or more vitamins;
   one or more minerals; and
   one or more amino acids.

47. The animal feed or animal feed additive of item 46, wherein the animal feed or animal feed additive further comprises one or more additional enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

48. The animal feed or animal feed additive of any of items 46 to 47, wherein the animal feed or animal feed additive comprises one or more microbes selected from the group consisting of Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium sp., Carnobacterium sp., Clostridium butyricum, Clostridium sp., Enterococcus faecium, Enterococcus sp., Lactobacillus sp., Lactobacillus acidophilus, Lactobacillus farciminus, Lactobacillus rhamnosus, Lactobacillus reuteri, Lactobacillus salivarius, Lactococcus lactis, Lactococcus sp., Leuconostoc sp., Megasphaera elsdenii, Megasphaera sp., Pediococsus acidilactici, Pediococcus sp., Propionibacterium thoenii, Propionibacterium sp. and Streptococcus sp. or any combination thereof.

49. Use of the polypeptide of any of items 1 to 7, the composition of any of items 8 to 11, the detergent composition of any of items 12 to 21, the granule of any of items 22 to 31 or the liquid formulation of any of items 32 to 45 for degrading mannan, such as linear mannan, galactomannan, glucomannan and galactoglucomannan.

50. Use of the polypeptide of any of items 1 to 7, the composition of any of items 8 to 11, the detergent composition of any of items 12 to 21, the granule of any of items 22 to 31 or the liquid formulation of any of items 32 to 45 for controlling the viscosity of drilling fluids.

51. Use of the polypeptide of any of items 1 to 7, the composition of any of items 8 to 11, the detergent composition of any of items 12 to 21, the granule of any of items 22 to 31 or the liquid formulation of any of items 32 to 45 for laundering, washing or cleaning a textile and/or a hard surface (such as dish wash).

52. The use of any of items 49 to 51, wherein the polypeptide has an enzyme detergency benefit.

53. A process for preparing a food or feed composition and/or food or feed additive, comprising mixing the polypeptide of any of items 1 to 7, the composition of any of items 8 to 11, the granule of any of items 22 to 31 or the liquid formulation of any of items 32 to 45 with one or more food or feed and/or food or feed additive ingredients.

54. The use of the polypeptide of any of items 1 to 7, the composition of any of items 8 to 11, the granule of any of items 22 to 31 or the liquid formulation of any of items 32 to 45 in the preparation of a food or feed composition and/or food or feed additive and/or food or feed stuff.

55. A process for degrading mannan, such as linear mannan, galactomannan, glucomannan and galactoglucomannan, comprising applying a composition comprising any of items 1 to 7, the composition of any of items 8 to 11, the detergent composition of any of items 12 to 21, the granule of any of items 22 to 31 or the liquid formulation of any of items 32 to 45 to the mannan.

56. The process of item 55, wherein the mannan is on the surface of a textile or hard surface, such as dish wash.

57. The process of item 55, wherein the mannan is used in fracturing of a subterranean formation perpetrated by a well bore.

58. The process of item 55, wherein the mannan is a component in borehole filtercake.

59. A process for producing a coffee extract, comprising the steps:
(a) providing roast and ground coffee beans;
(b) adding to said coffee beans water and a polypeptide of any of items 1 to 7, the composition of any of items 8 to 11, the granule of any of items 22 to 31 or the liquid formulation of any of items 32 to 45;
(c) incubating to make an aqueous coffee extract; and
(d) separating the coffee extract from the extracted coffee beans.

60. A process for degrading a cellulosic material, comprising: treating the cellulosic material with an enzyme composition in the presence of the polypeptide having mannanase activity of any of items 1 to 7.

61. A process for producing a fermentation product, comprising:
(a) saccharifying a cellulosic material with an enzyme composition, wherein the enzyme composition comprises the polypeptide of any of items 1 to 7, the composition of any of items 8 to 11, the granule of any of items 22 to 31 or the liquid formulation of any of items 32 to 45;
(b) fermenting the saccharified cellulosic material with one or more fermenting microorganisms to produce the fermentation product; and
(c) recovering the fermentation product from the fermentation.

62. The process of any of items 60 or 61, wherein the cellulosic material is pretreated.

63. The process of any of items 60 to 62, wherein the enzyme composition comprises one or more enzymes selected from the group consisting of cellulase, AA9 polypeptide, hemicellulase, esterase, expansin, lignolytic enzyme, oxidoreductase, pectinase, protease, and swollenin.

64. A process of fermenting a cellulosic material, comprising: fermenting the cellulosic material with one or more fermenting microorganisms, wherein the cellulosic material is saccharified with an enzyme composition, wherein the enzyme composition comprises the polypeptide of any of items 1 to 7, the composition of any of items 8 to 11, the granule of any of items 22 to 31 or the liquid formulation of any of items 32 to 45.

65. The process of item 64, wherein the cellulosic material is pretreated before saccharification.

66. The process of any of items 64 to 65, wherein the enzyme composition comprises one or more enzymes selected from the group consisting of cellulase, AA9 polypeptide, hemicellulase, esterase, expansin, lignolytic enzyme, oxidoreductase, pectinase, protease, and swollenin.

67. A polynucleotide encoding the polypeptide of any of items 1 to 7.

68. A nucleic acid construct or expression vector comprising the polynucleotide of item 67 operably linked to one or more control sequences that direct the production of the polypeptide in an expression host.

69. A recombinant host cell comprising the polynucleotide of item 67 operably linked to one or more control sequences that direct the production of the polypeptide.
70. A process of producing the polypeptide of any of items 1 to 7, comprising:
    (a) cultivating a cell, which in its wild-type form produces the polypeptide, under conditions conductive for production of the polypeptide; and
    (b) recovering the polypeptide.
71. A process of producing the polypeptide of any of items 1 to 7, comprising:
    (a) cultivating the host cell of item 46 under conditions conducive for production of the polypeptide; and
    (b) recovering the polypeptide.
72. A transgenic plant, plant part or plant cell transformed with a polynucleotide encoding the polypeptide of any of items 1 to 7.
73. A whole broth formulation or cell culture composition comprising a polypeptide of any of items 1 to 7.
74. Use of the polypeptide of any of items 1 to 7, the composition of any of items 8 to 11, the detergent composition of any of items 12 to 21, the granule of any of items 22 to 31 or the liquid formulation of any of items 32 to 45 for preventing, reducing or removing a biofilm from an item.
75. Use of the polypeptide of any of items 1 to 7, the composition of any of items 8 to 11, the detergent composition of any of items 12 to 21, the granule of any of items 22 to 31 or the liquid formulation of any of items 32 to 45 for preventing, reducing or removing malodor from an item.
76. A method of preparing a fermented beverage comprising mixing the polypeptide of any of items 1 to 7, the composition of any of items 8 to 11, the granule of any of items 22 to 31 or the liquid formulation of any of items 32 to 45 with malt and/or adjunct.
77. A method of preparing a fermented beverage comprising contacting a mash and/or a wort with the polypeptide of any of items 1 to 7, the composition of any of items 8 to 11, the granule of any of items 22 to 31 or the liquid formulation of any of items 32 to 45.
78. The process of any of items 76 to 77, wherein the fermented beverage is a wine or a beer.
79. A method of preparing baked products comprising mixing the polypeptide of any of items 1 to 7, the composition of any of items 8 to 11, the granule of any of items 22 to 31 or the liquid formulation of any of items 32 to 45 to a dough, followed by baking the dough.
80. A method to improve dough tolerance, flexibility and/or stickiness of a dough comprising mixing the polypeptide of any of items 1 to 7, the composition of any of items 8 to 11, the granule of any of items 22 to 31 or the liquid formulation of any of items 32 to 45 to the dough.
81. A method to improve the crumb structure and retard staling in the final baked product comprising mixing the polypeptide of any of items 1 to 7, the composition of any of items 8 to 11, the granule of any of items 22 to 31 or the liquid formulation of any of items 32 to 45 to the dough, followed by baking the dough.
82. A method of preparing milk or dairy products comprising adding to the milk or dairy product
    (a) glucomannan, galactomannan and/or galactoglucomannan; and
    (b) the polypeptide of any of items 1 to 7, the composition of any of items 8 to 11, the granule of any of items 22 to 31 or the liquid formulation of any of items 32 to 45.
83. A method of bleaching paper pulps comprising incubating the paper pulp with the polypeptide of any of items 1 to 7, the composition of any of items 8 to 11, the detergent composition of any of items 12 to 21, the granule of any of items 22 to 31 or the liquid formulation of any of items 32 to 45 to the dough.

The present invention is further described by the following examples that should not be construed as limiting the scope of the invention.

EXAMPLES

Strains

The DNA encoding the GH26 mannanase genes was isolated from *Paenibacillus illinoisensis* isolated from soil samples collected in Virginia, United States in 2014 and from *Paenibacillus* sp. isolated from a sand sample collected in The United States in 1991

Chromosomal DNA from the strains were subjected to full genome sequencing using Illumina technology. The genome sequences were analyzed for protein sequences that had glycosyl hydrolase family 26 domains (according to the CAZY definition) and the GH26 mannanase genes were identified in the two genomes.

Materials

Chemicals used as buffers and substrates were commercial products of at least reagent grade.

Example 1: Reducing End Assay

For estimating the mannose yield after substrate hydrolysis, a reducing end assay developed by Lever (1972), Anal. Biochem. 47: 273-279, was used. The assay is based on 4-hydroxybenzoic acid hydrazide, which under alkaline conditions reacts with the reducing ends of saccharides. The product is a strong yellow anion, which absorbs at 410 nm.

Method

4-Hydroxybenzhydrazide (PAHBAH) (Sigma,H9882) was diluted in PAHBAH buffer to a concentration of 15 mg/ml. PAHBAH buffer contained: 50 g/L K-Na-tartrate (Merck, 1.08087) and 20 g/L sodium hydroxide(Sigma, S8045). This PAHBAH mix was made just before usage.

70 µl PAHBAH mix and MiliQ water were mixed in a 96 well PCR plate (Thermo Scientific). Samples from hydrolysis experiment were added. Samples and MiliQ always reached the total volume of 150 µl, but the dilution of the sample differed. The plate was sealed with Adhesive PCR Sealing Foil Sheets (Thermo Scientific). Plates were incubated at 95° C. for 10 min, cooled down and kept at 10° C. for 1 min in PTC-200 Thermal Cycler (MJ Research). 100 µl sample was transferred to a 96 well microtiter plate, flat bottomed (Nunc™) and color development measured at 405 nm on a SpectraMax 190 Absorbance Microplate Reader (Molecular Devices). Results were compared to mannose standards, that had undergone the same treatment and dilution as the samples to which they were compared.

Example 2: Cloning and Expression of GH26 beta-1,4-mannanases from *Paenibacillus Illinoisensis* and from *Paenibacillus_Sp*

The gene encoding the GH26 mannanase from *Paenibacillus illinoisensis* (SEQ ID NO: 1) was expressed in 2 versions. First as the full-length gene including the GH26 domain and a CBM35 domain and secondly as a truncated version only containing the GH26 domain. The gene encoding the GH26 mannanase from *Paenibacillus* sp. was expressed as the full length gene including the GH26 domain and the CBM35 domain. The three constructs expressed the enzymes as secreted enzymes. In the two full-length constructs the genes native secretion signal was replaced with a *Bacillus clausii* secretion signal (with the following amino acid sequence: MKKPLGKIVASTAL-LISVAFSSSIASA, SEQ ID NO: 9) and a HHHHHH (SEQ ID NO: 17)-tag was added directly on the C-terminal of the *Paenibacillus illinoisensis* mannanase, while a HPHPHPHP (SEQ ID NO: 16)-tag was added directly on the C-terminal of the *Paenibacillus* sp. mannanase. In the truncated construct of the *Paenibacillus illinoisensis* mannanase thegene native secretion signal was replaced with a *Bacillus licheniformis* secretion signal (with the following amino acid sequence: MKQQKRLYARLLTLLFALIFLLPHSAAAA, SEQ ID NO: 10) and a 6×His tag was added directly on the C-terminal of the protein. The 2 genes from *Paenibacillus illinoisensis* (SEQ ID NO: 1) and *Paenibacillus* sp. (SEQ ID NO: 11) were amplified from genomic DNA of the 2 strains with specific primers. The constructs were made as a linear integration constructs, where the amplified genes were fused by PCR between two *Bacillus subtilis* homologous chromosomal regions along with a strong promoter and a chloramphenicol resistance marker. The fusion was made by SOE PCR (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68). The SOE PCR method is also described in patent application WO 2003095658.

The genes were expressed under the control of a triple promoter system (as described in WO 1999/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The linear PCR constructs where transformed into *Bacillus subtilis*. Transformants were selected on LB plates supplemented with 6 µg of chloramphenicol per ml. A recombinant *Bacillus subtilis* clone from each construct containing the integrated expression construct was cultivated in 3L flasks containing 500 ml yeast extract-based medium at 30° C. for 3 days with shaking at 250 rpm. Each of the culture broths were centrifuged at 20,000×g for 20 minutes and the supernatants were carefully decanted from the pelleted material. Each supernatant was filtered using a filtration unit equipped with a 0.2 µm filter (Nalgene) to remove any cellular debris. The enzymes were purified from the filtered supernatant as described in Example 3.

Example 3: Purification of GH26 Mannanases

The 3 constructs of the GH26 mannanases were purified in the following way: The pH of the supernatant was adjusted to pH 8 with 3 M Tris, left for 1 hour, and then filtered using a filtration unit equipped with a 0.2 µm filter (Nalgene). The filtered supernatant was applied to a 5 ml HisTrap™ Excel column (GE Healthcare Life Sciences) pre-equilibrated with 5 column volumes (CV) of 50 mM Tris/HCl pH 8. Unbound protein was eluted by washing the column with 8 CV of 50 mM Tris/HCl pH 8. The mannanase was eluted with 50 mM HEPES pH 7-10 mM imidazole and elution was monitored by absorbance at 280 nm. The eluted mannanase was desalted on a HiPrep™ 26/10 desalting column (GE Healthcare Life Sciences) pre-equilibrated with 3 CV of 50 mM HEPES pH 7-100 mM NaCl. The mannanase was eluted from the column using the same buffer at a flow rate of 10 ml/minute. Relevant fractions were selected and pooled based on the chromatogram and SDS-PAGE analysis using 4-12% Bis-Tris gels (Invitrogen) and 2-(N-morpholino)ethanesulfonic acid (MES) SDS-PAGE running buffer (Invitrogen). The gel was stained with InstantBlue (Novexin) and destained using miliQ water. The concentration of the purified enzyme was determined by absorbance at 280 nm.

Characteristics for the GH26 Mannanase (Amino Acids SEQ ID NO: 6)

The molecular weight determined by intact molecular weight analysis was 56551.2 Da.

The mature sequence (from Intact MS data):

(amino acids 1-497 of SEQ ID NO: 6)
AITVPGFVVEPHTSSDQNQAIIATFKDASIEGYGIKKRDEATAKAEDD

LYDGTGYISYFFEEDEKATVQKGSATFQVKAPENGLYELSLGYYIPEG

NGDKATSIQVNGSGAGELTLSAPKPGTVRAEKKMTKVLLNSGNNSIQI

LRGWGYYGIEYIKLERVEPRITTQKTMMDPLSNSKASPQAKALMKFMT

NQYGKKIISGQQTLEDAAWIYQQTGKYPALVSSDLMDYSPSRVENGST

SNEVEKMMEWYKRGGIVSLSWHWNAPKGIGSNEPGHEWWRGFNTEFTT

FDVEYALNHPESEDYKLLIRDIDAIATQLKRLQEHHIPVLWRPLHEAE

GGWFWWGAKGPEPAKKLYRLMYERLTEKHGLNNLIWVWNSVKEEWYPG

DDVVDMVSVDIYNPPGDYSPNIAKYDELLFLSKHKKLVALAENGPIPD

PDLLQTYGAHWSYFNTWTGDVLRDGKTNTKEHLKKVYNHDNVITLDEL

PKGLYDSPRWKHHHHHH

The calculated molecular weight from this mature sequence is 56551.0 Da

Example 4: Preparation of Fenugreek Gum

Fenugreek gum was extracted according to a modified procedure (Brummer, Y. et al. *Food Hydrocolloids* 2003, 17, 229-236).

124 g Ground fenugreek seeds, purchased in the local supermarket, but also available online, were extracted with 70° C. warm heptane (880 mL) for 60 min. to remove non-polar lipids. After suction filtration the residue was extracted at 60° C. with 96% ethanol (760 mL) for 150 min. to remove polar lipids. After suction filtration the residue was suspended in 1,200 g 60:40 (w/w: 720:480 g) ethanol: water mixture and stirred for 60 min. at ambient temperature to remove sugars and salts. After suction filtration, the residue was left to dry overnight at ambient temperature.

Fenugreek galactomannan was extracted from 50.0 g of the defatted Fenugreeks seeds in 1,700 g ion-exchanged water at 5-10° C. for 120 min. The resulting slurry was centrifuged (14,000 g for 20 min). The supernatant was precipitated in 96% ethanol to a final concentration of 50% (w/w). The resulting coagulum was pressed in suspended in 96% ethanol to facilitate water removal. Hereafter the resulting fibers were dried over night at ambient temperature. The overall yield was 18%.

Example 5: Substrate Specificity of GH26 Mannanases

Fenugreek gum and guar gum are galactomannans. Fenugreek gum is the most substituted galactomannan and was prepared as described in example 4. Guar gum is less substituted and was purchased from Megazyme, USA.

2.5 mg/mL solutions of galactomannans were prepared in a phosphate buffer, pH 7.5 and incubated for 30 min at 30° C. with 0.25 mg/L mannanase or without enzyme (blank). Mannaway is a commercially available mannanase available from Novozymes A/S (Bagsværd, Denmark). The reducing ends were then measured as described in example 1.

The difference in optical density at 405 nm (ΔOD) was calculated by subtracting the blank sample (no added enzyme, i.e. pure galactomannan solution incubated for 30 min at 30° C.) and the data is presented in table 1 below.

TABLE 1

Reducing ends released from different substrates

| Substrate | Mannaway | GH26 mannanase from Paenibacillus illinoisensis |
|---|---|---|
| Fenugreek gum | −0.01 | 0.30 |
| Guar gum | 0.17 | 0.55 |

The GH26 mannanase from Paenibacillus illinoisensis (SEQ ID NO: 6) was superior at hydrolyzing fenugreek and guar gum compared to the commercial product Mannaway.

Example 6: Wash Performance of the GH26 Mannanase Using AMSA

The wash performance in laundry washing is assessed using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance.

Colour measurements are made with a professional flat-bed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}$$

The experiments were conducted as described in the Automatic Mechanical Stress Assay (AMSA) for laundry method using a 1 cycle wash procedure and the experimental conditions specified in Table 2.

TABLE 2

Conditions for AMSA Washing Trial

| Test Solution | Model B detergent 1 g/L |
| | Model T detergent 1.6 g/L |
| Test solution volume | 160 µL |
| pH | Model B, pH unadjusted (measured to be 7.8). |
| | Model T, pH unadjusted (measured to be 9.7) |
| Wash time | 20 minutes |
| Temperature | 20° C. or 40° C. |
| Water hardness | 15° dH |
| $Ca^{2+}:Mg^{2+}:CO_3^{2-}$ ratio | 4:1:7.5 |

The composition of Model T detergent is given in table 3 and Model B detergent is given in table 4.

TABLE 3

Model T detergent composition

| Ingredient (abbreviation) | Explanation | Weight % |
|---|---|---|
| LAS | alkylbenzene-sulfonic acid, sodium salt | 11.72 |
| AS | sodium alkyl sulfafe, sodium salt | 1.97 |
| Soap | | 2.15 |
| AEO | alcohol ethoxylate | 3.33 |
| Sodium carbonate | | 14.97 |
| Sodium (di)silicate | | 3.12 |
| Zeolite 4A + PCA | zeolite 4A + copoly(acrylic acid/maleic acid), sodium salt | 20.38 |
| HEDP | 1-hydroxyethane-1,1-diylbis(phosphonic acid), tetrasodium salt; tetrasodium etidronate | 0.15 |
| Sodium citrate | | 2.00 |
| CPP | copolymer polyether/polyester | 0.51 |
| Sodium sulfate | | 38.70 |
| Silicone | | 1.00 |

TABLE 4

Model B detergent composition

| Ingredient (abbreviation) | Explanation | Weight % |
|---|---|---|
| LAS | (C10-C13)alkylbenzene-sulfonic acid | 7.20 |
| SLES | sodium lauryl ether sulfate | 10.58 |
| Soy soap | | 2.75 |
| Coco soap | | 2.75 |
| AEO | alcohol ethoxylate | 6.60 |
| NaOH | Sodium hydroxide | 1.05 |
| Ethanol | | 2.70 |
| Isopropanol | | 0.30 |
| MPG | monopropylene glycol | 6.00 |
| Glycerol | | 1.71 |
| TEA | triethanolamine | 3.33 |
| Sodium formate | | 1.00 |
| Sodium citrate | | 2.00 |
| DTMPA | diethylenetriaminepentakis(methylene)-pentakis (phosphonic acid), heptasodium salt | 0.48 |
| PCA | polycarboxylic acid type polymer, sodium salt | 0.46 |
| Phenoxyethanol | | 0.50 |
| Ion exchanged water | | 50.59 |

Water hardness was adjusted by addition of $CaCl_2$, $MgCl_2$, and $NaHCO_3$ to the test system. After washing the textiles were flushed in tap water and air-dried. Two types of swatch were used; these are commercial test materials, C-S-43, Guar gum with carbon black on cotton and C-S-73, Locust bean gum with carbon black on cotton, available from Center for Testmaterials BV, Stoomloggerweg 11, 3133 KT Vlaardingen, the Netherlands.

Results are presented in tables 5 to 8 for two doses of each enzyme at two different temperatures and two different detergent compositions. Each number is the delta intensity (ΔInt) calculated by subtracting either the detergent blank. Each measurement is the average of minimum 2 separate wells in the AMSA set up

TABLE 5

AMSA wash results in model detergent B on Guar gum swatch C-S-43 at 20° C.

| Enzyme | Delta intensity (ΔInt) | |
|---|---|---|
| (mg enzyme protein/L) | Mannaway | SEQ ID NO: 6 |
| 0.05 | 8 | 15 |
| 0.25 | 9 | 17 |

TABLE 6

AMSA wash results in model detergent B on Guar gum swatch C-S-43 at 40° C.

| Enzyme | Delta intensity (ΔInt) | |
|---|---|---|
| (mg enzyme protein/L) | Mannaway | SEQ ID NO: 6 |
| 0.05 | 11 | 16 |
| 0.25 | 15 | 19 |

TABLE 7

AMSA wash results in model detergent T on Guar gum swatch C-S-43 at 20° C.

| Enzyme | Delta intensity (ΔInt) | |
|---|---|---|
| (mg enzyme protein/L) | Mannaway | SEQ ID NO: 6 |
| 0.05 | 5 | 15 |
| 0.25 | 11 | 18 |

TABLE 8

AMSA wash results in model detergent T on Guar gum swatch C-S-43 at 40° C.

| Enzyme | Delta intensity (ΔInt) | |
|---|---|---|
| (mg enzyme protein/L) | Mannaway | SEQ ID NO: 6 |
| 0.05 | 6 | 11 |
| 0.25 | 12 | 17 |

The full length GH26 mannanase from *Paenibacillus illinoisensis* (SEQ ID NO: 6) was superior at removing the guar gum at both 20° C. and 40° C., performing up to twice as well as the commercial enzyme Mannaway in model detergent B as well as model detergent T.

Example 7: Wash Performance of the GH26 Mannanase Using Terg-O-Tometer Washing Trial The terg-o-tometer is an industry standard. 1 L of wash solution is incubated in a water bath temperature controlled environment. The solution was mixed for 5 min before adding 1 L to each of the beakers. The temperature in the beakers was measured to be 20.0° C. The washed and rinsed swatches were left to dry overnight in a drying cabinet, and measured as indicated in table 9 below.

TABLE 9

Conditions for Terg-O-tometer Washing Trial

| Test Solution | Model B detergent 1 g/L |
|---|---|
| Test solution volume | 1 L |
| pH | Model B unadjusted |
| Wash time | 30 minutes |
| Temperature | 20° C. |
| Water hardness | 15° dH |
| $Ca^{2+}:Mg^{2+}:CO_3^{2-}$ ratio | 4:1:7.5 |
| Mechanical action | 120 rpm |
| Enzyme dose | 0.05 mg/L |

Here, the stains used were a combination of food and technical stains provided by Center for Testmaterials BV, Stoomloggerweg 11, 3133 KT Vlaardingen, the Netherlands (see table 10).

TABLE 10

Stains used for the Terg-o-tometer washing trials

| Material | Source |
|---|---|
| KC-H033 Chocolate Ice Cream with Guar Gum | CFT |
| C-S-43 Guar Gum | CFT |
| C-S-73 Locust Bean Gum | CFT |

Wash performance is expressed as a delta remission value (ΔRem). After washing and rinsing the swatches were spread out flat and allowed to air dry at room temperature overnight. Light reflectance evaluations of the swatches were done using a Macbeth Color Eye 7000 reflectance spectrophotometer with large aperture. The measurements were made without UV in the incident light and remission at 460 nm was extracted. The dry swatches were measured with ColorEye 2. Measurement with small aperture through 3 layers (3 of the same type of swatch from the same beaker), 2 measurements on each swatch on the front side marked with beaker and swatch number. Remission values for individual swatches were calculated by subtracting the remission value of the control swatch from the remission value of the washed swatch. Calculating the enzyme effect was done by taking the measurements from washed swatches with enzymes and subtract with the measurements from washed without enzyme for each stain. The total enzyme performance was calculated as the average of individual $\Delta Rem_{enzyme}$ and is shown in table 11 below.

TABLE 11

Terg-o-tometer Wash results

| Stain | Mannaway | SEQ ID NO: 6 |
|---|---|---|
| KC-H033 Vienetta | 9 | 8 |
| C-S-43 Guar Gum | 4 | 8 |
| C-S-73 Locust Bean Gum | 9 | 8 |

The full length GH26 mannanase from *Paenibacillus illinoisensis* (SEQ ID NO: 6) performed as well as the commercial enzyme Mannaway for the Vienetta and locust bean gum stain and was superior at removing the guar gum stain, performing twice as well as Mannaway.

Example 8: Wash Performance of the GH26 Mannanases Using AMSA

The experiments were conducted as described in example 6 and the experimental conditions specified in table 12.

TABLE 12

Conditions for AMSA Washing Trial

| | |
|---|---|
| Test Solution | Model O detergent 2 g/L |
| Test solution volume | 160 μL |
| pH | Model O, pH unadjusted |
| Enzyme concentration | 0.25 mg/L |
| Wash time | 20 minutes |
| Temperature | 20° C. |
| Water hardness | 15° dH |
| $Ca^{2+}:Mg^{2+}:CO_3^{2-}$ ratio | 4:1:7.5 |

The composition of Model O detergent is given in table 13. Results are presented in table 14.

TABLE 13

Model O detergent composition

| Ingredient (abbreviation) | Explanation | Weight % |
|---|---|---|
| LAS | sodium (C10-C13)alkylbenzene-sulfonic acid | 4.00 |
| SLES | sodium lauryl ether sulfate | 8.00 |
| Soy soap | | 1.00 |
| AEO | alcohol ethoxylate | 4.00 |
| TEA | triethanolamine | 0.40 |
| Sodium citrate | trisodiunn citrate dihydrate | 2.00 |
| Calcium chloride | calcium chloride dihydrate | 0.02 |
| Ion exchanged water | | 80.58 |

TABLE 14

AMSA wash results in model O detergent on Guar gum swatch C-S-43
Delta intensity (ΔInt)

| Mannaway | SEQ ID NO: 15 |
|---|---|
| 10 | 20 |

The full length GH26 mannanase from *Paenibacillus* sp. (SEQ ID NO: 15) was superior at removing guar gum, performing up to twice as well as the commercial enzyme Mannaway.

Example 9: Wash Performance of GH26 Mannanases Using Terg-O-Tometer Washing Trial The experiments were conducted as described in example 7 and the experimental conditions specified in table 15.

TABLE 15

Conditions for Terg-O-tometer Washing Trial

| | |
|---|---|
| Test Solution | Model A detergent 3.3 g/L |
| Test solution volume | 1 L |
| pH | Model A unadjusted |
| Wash time | 30 minutes |
| Temperature | 20° C. |
| Water hardness | 15° dH |
| $Ca^{2+}:Mg^{2+}:CO_3^{2-}$ ratio | 4:1:7.5 |
| Mechanical action | 120 rpm |
| Enzyme dose | 0.6 mg/L |

The composition of Model A detergent is given in table 16. Results are presented in table 17.

TABLE 16

Model A detergent composition

| Ingredient (abbreviation) | Explanation | Wt % |
|---|---|---|
| LAS | (C10-C13)alkylbenzene-sulfonic acid | 12.00 |
| SLES | sodium lauryl ether sulfate | 17.63 |
| Soy soap | | 2.75 |
| Coco soap | | 2.75 |
| AEO | alcohol ethoxylate | 11.00 |
| NaOH | Sodium hydroxide | 1.75 |
| Ethanol | | 2.70 |
| Isopropanol | | 0.30 |
| MPG | monopropylene glycol | 6.00 |
| Glycerol | | 1.71 |
| TEA | triethanolamine | 3.33 |
| Sodium formate | | 1.00 |
| Sodium citrate | | 2.00 |
| DTMPA | diethylenetriaminepentakis(methylene)-pentakis (phosphonic acid), heptasodiunn salt | 0.48 |
| PCA | polycarboxylic acid type polymer, sodium salt | 0.46 |
| Phenoxyethanol | | 0.50 |
| Ion exchanged water | | 33.64 |

TABLE 17

Terg-o-tometer Wash results in model A detergent on Guar gum swatch C-S-43
Delta remission (ΔRem$_{enzyme}$)

| Mannaway | SEQ ID NO: 6 | SEQ ID NO: 8 |
|---|---|---|
| 11.5 | 14.7 | 14.1 |

Both the full length (SEQ ID NO: 6) as well as the truncated (SEQ ID NO: 8) GH26 mannanase from *Paenibacillus illinoisensis* are superior at removing guar gum relative to the commercial enzyme Mannaway.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

SEQUENCE LISTING

<160> NUMBER OF SEQ ID NOS: 17

<210> SEQ ID NO 1
<211> LENGTH: 1602

```
<212> TYPE: DNA
<213> ORGANISM: Paenibacillus illinoisensis
<220> FEATURE:
<221> NAME/KEY: CDS
<222> LOCATION: (1)..(1599)
<220> FEATURE:
<221> NAME/KEY: sig_peptide
<222> LOCATION: (1)..(126)
<220> FEATURE:
<221> NAME/KEY: mat_peptide
<222> LOCATION: (127)..(1599)

<400> SEQUENCE: 1
```

| | | | | | | | | | | | | | | | | |
|---|---|---|---|---|---|---|---|---|---|---|---|---|---|---|---|---|
| atg | aag | gaa | aaa | tca | ggt | tca | cct | att | aga | tat | tca | aca | tca | aag | aaa | 48 |
| Met | Lys | Glu | Lys | Ser | Gly | Ser | Pro | Ile | Arg | Tyr | Ser | Thr | Ser | Lys | Lys | |
| | -40 | | | | -35 | | | | | -30 | | | | | | |
| acg | tat | ttt | aag | ttt | gga | tcg | gcc | att | ttc | gtt | ctg | tat | atc | ctc | atg | 96 |
| Thr | Tyr | Phe | Lys | Phe | Gly | Ser | Ala | Ile | Phe | Val | Leu | Tyr | Ile | Leu | Met | |
| | -25 | | | | -20 | | | | | -15 | | | | | | |
| ttg | agt | ttt | act | cac | tcc | agg | gtg | gaa | gca | gct | att | acg | gta | ccg | gga | 144 |
| Leu | Ser | Phe | Thr | His | Ser | Arg | Val | Glu | Ala | Ala | Ile | Thr | Val | Pro | Gly | |
| -10 | | | | | -5 | | | | | -1 | 1 | | | | 5 | |
| ttt | gtt | gtt | gaa | ccc | cat | act | tct | tct | gat | caa | aac | cag | gcc | ata | ata | 192 |
| Phe | Val | Val | Glu | Pro | His | Thr | Ser | Ser | Asp | Gln | Asn | Gln | Ala | Ile | Ile | |
| | | | 10 | | | | | 15 | | | | | 20 | | | |
| gcc | aca | ttc | aaa | gat | gct | tcc | atc | gaa | ggg | tac | ggg | atc | aag | aaa | cgc | 240 |
| Ala | Thr | Phe | Lys | Asp | Ala | Ser | Ile | Glu | Gly | Tyr | Gly | Ile | Lys | Lys | Arg | |
| | | 25 | | | | | 30 | | | | | 35 | | | | |
| gat | gag | gca | aca | gcc | aaa | gcg | gag | gac | gat | cta | tat | gat | ggt | aca | ggt | 288 |
| Asp | Glu | Ala | Thr | Ala | Lys | Ala | Glu | Asp | Asp | Leu | Tyr | Asp | Gly | Thr | Gly | |
| | 40 | | | | | 45 | | | | | 50 | | | | | |
| tat | atc | tct | tat | ttt | ttt | gaa | gag | gat | gaa | aag | gcc | aca | gtt | cag | aag | 336 |
| Tyr | Ile | Ser | Tyr | Phe | Phe | Glu | Glu | Asp | Glu | Lys | Ala | Thr | Val | Gln | Lys | |
| 55 | | | | | 60 | | | | | 65 | | | | | 70 | |
| gga | agc | gct | aca | ttc | cag | gtt | aaa | gca | ccg | gaa | aat | ggg | ctt | tat | gag | 384 |
| Gly | Ser | Ala | Thr | Phe | Gln | Val | Lys | Ala | Pro | Glu | Asn | Gly | Leu | Tyr | Glu | |
| | | | | 75 | | | | | 80 | | | | | 85 | | |
| tta | agt | ttg | gga | tac | tac | atc | cca | gaa | gga | aat | ggg | gat | aaa | gcg | act | 432 |
| Leu | Ser | Leu | Gly | Tyr | Tyr | Ile | Pro | Glu | Gly | Asn | Gly | Asp | Lys | Ala | Thr | |
| | | | 90 | | | | | 95 | | | | | 100 | | | |
| tcc | atc | caa | gta | aat | ggt | tcg | gga | gcc | ggg | gag | ctg | acg | ctc | agt | gcg | 480 |
| Ser | Ile | Gln | Val | Asn | Gly | Ser | Gly | Ala | Gly | Glu | Leu | Thr | Leu | Ser | Ala | |
| | | 105 | | | | | 110 | | | | | 115 | | | | |
| cca | aag | cca | ggg | acg | gtt | cga | gca | gaa | aaa | aag | atg | aca | aag | gtg | ctt | 528 |
| Pro | Lys | Pro | Gly | Thr | Val | Arg | Ala | Glu | Lys | Lys | Met | Thr | Lys | Val | Leu | |
| | 120 | | | | | 125 | | | | | 130 | | | | | |
| ctg | aac | agc | ggt | aac | aac | tcc | att | caa | ata | tta | agg | ggg | tgg | ggg | tac | 576 |
| Leu | Asn | Ser | Gly | Asn | Asn | Ser | Ile | Gln | Ile | Leu | Arg | Gly | Trp | Gly | Tyr | |
| 135 | | | | | 140 | | | | | 145 | | | | | 150 | |
| tat | ggc | att | gag | tat | atc | aag | ctt | gaa | cgt | gta | gaa | ccc | cgc | ata | acc | 624 |
| Tyr | Gly | Ile | Glu | Tyr | Ile | Lys | Leu | Glu | Arg | Val | Glu | Pro | Arg | Ile | Thr | |
| | | | | 155 | | | | | 160 | | | | | 165 | | |
| acg | caa | aaa | aca | atg | atg | gat | ccc | tta | agt | aac | tcc | aaa | gca | tct | ccg | 672 |
| Thr | Gln | Lys | Thr | Met | Met | Asp | Pro | Leu | Ser | Asn | Ser | Lys | Ala | Ser | Pro | |
| | | 170 | | | | | 175 | | | | | 180 | | | | |
| caa | gcc | aaa | gca | tta | atg | aaa | ttt | atg | acc | aac | cag | tat | gga | aaa | aag | 720 |
| Gln | Ala | Lys | Ala | Leu | Met | Lys | Phe | Met | Thr | Asn | Gln | Tyr | Gly | Lys | Lys | |
| | 185 | | | | | 190 | | | | | 195 | | | | | |
| att | ata | tca | ggc | cag | caa | acc | cta | gag | gac | gca | gcg | tgg | atc | tat | cag | 768 |
| Ile | Ile | Ser | Gly | Gln | Gln | Thr | Leu | Glu | Asp | Ala | Ala | Trp | Ile | Tyr | Gln | |
| 200 | | | | | 205 | | | | | 210 | | | | | | |
| cag | act | gga | aag | tac | cct | gca | ctg | gtt | tcc | agt | gat | ttg | atg | gat | tat | 816 |

| | | | | | | | | | | | | | | | |
|---|---|---|---|---|---|---|---|---|---|---|---|---|---|---|---|
|Gln|Thr|Gly|Lys|Tyr|Pro|Ala|Leu|Val|Ser|Ser|Asp|Leu|Met|Asp|Tyr|
|215| | | |220| | | |225| | | |230| | | |

```
tct cca tcc cgt gtg gaa aac gga agc acc tcg aat gag gta gaa aag    864
Ser Pro Ser Arg Val Glu Asn Gly Ser Thr Ser Asn Glu Val Glu Lys
            235                 240                 245 atg atg gag tgg tac aag cgt gga ggc att gtc tcc tta agc tgg cac    912
Met Met Glu Trp Tyr Lys Arg Gly Gly Ile Val Ser Leu Ser Trp His
        250                 255                 260 tgg aat gcg ccg aaa ggg atc ggc agc aat gaa cca ggc cat gag tgg    960
Trp Asn Ala Pro Lys Gly Ile Gly Ser Asn Glu Pro Gly His Glu Trp
            265                 270                 275 tgg cgg ggg ttc aat aca gag ttc aca acc ttc gat gta gaa tat gct   1008
Trp Arg Gly Phe Asn Thr Glu Phe Thr Thr Phe Asp Val Glu Tyr Ala
        280                 285                 290 ctg aat cat ccg gaa tcg gaa gat tac aag ctt cta att cgg gat att   1056
Leu Asn His Pro Glu Ser Glu Asp Tyr Lys Leu Leu Ile Arg Asp Ile
295                 300                 305                 310 gat gcg atc gct act caa ttg aag cgg ctg cag gag cac cat att ccc   1104
Asp Ala Ile Ala Thr Gln Leu Lys Arg Leu Gln Glu His His Ile Pro
                315                 320                 325 gta ctt tgg aga cca ctg cat gaa gcg gag ggt ggc tgg ttt tgg tgg   1152
Val Leu Trp Arg Pro Leu His Glu Ala Glu Gly Gly Trp Phe Trp Trp
            330                 335                 340 gga gcc aaa ggt cct gaa cct gcg aaa aaa ttg tat cga tta atg tac   1200
Gly Ala Lys Gly Pro Glu Pro Ala Lys Lys Leu Tyr Arg Leu Met Tyr
        345                 350                 355 gaa cga ttg acg gag aag cat ggg tta aac aat ctc att tgg gtt tgg   1248
Glu Arg Leu Thr Glu Lys His Gly Leu Asn Asn Leu Ile Trp Val Trp
360                 365                 370 aac tct gtt aag gag gag tgg tac ccg gga gat gat gtg gtg gat atg   1296
Asn Ser Val Lys Glu Glu Trp Tyr Pro Gly Asp Asp Val Val Asp Met
375                 380                 385                 390 gta agt gtc gac att tat aat cca ccc ggt gat tac agc ccg aac att   1344
Val Ser Val Asp Ile Tyr Asn Pro Pro Gly Asp Tyr Ser Pro Asn Ile
                395                 400                 405 gcc aag tac gac gag ctc ttg ttt ctg agc aag cat aag aaa ctt gtg   1392
Ala Lys Tyr Asp Glu Leu Leu Phe Leu Ser Lys His Lys Lys Leu Val
            410                 415                 420 gca ctc gcc gaa aat ggg ccg att ccc gat cct gat ctg ctg cag aca   1440
Ala Leu Ala Glu Asn Gly Pro Ile Pro Asp Pro Asp Leu Leu Gln Thr
        425                 430                 435 tac ggt gca cat tgg agc tat ttt aat acc tgg act ggc gat gtt ctg   1488
Tyr Gly Ala His Trp Ser Tyr Phe Asn Thr Trp Thr Gly Asp Val Leu
440                 445                 450 cgt gat gga aaa acg aat aca aag gaa cat ttg aaa aaa gtc tac aat   1536
Arg Asp Gly Lys Thr Asn Thr Lys Glu His Leu Lys Lys Val Tyr Asn
455                 460                 465                 470 cat gac aac gtg atc aca ctg gat gaa ctt ccc aag gga ttg tac gac   1584
His Asp Asn Val Ile Thr Leu Asp Glu Leu Pro Lys Gly Leu Tyr Asp
                475                 480                 485 agt cct aga tgg aaa tag                                           1602
Ser Pro Arg Trp Lys
            490
```

<210> SEQ ID NO 2
<211> LENGTH: 533
<212> TYPE: PRT
<213> ORGANISM: Paenibacillus illinoisensis

<400> SEQUENCE: 2

```
Met Lys Glu Lys Ser Gly Ser Pro Ile Arg Tyr Ser Thr Ser Lys Lys
        -40                 -35                 -30

Thr Tyr Phe Lys Phe Gly Ser Ala Ile Phe Val Leu Tyr Ile Leu Met
        -25                 -20                 -15

Leu Ser Phe Thr His Ser Arg Val Glu Ala Ile Thr Val Pro Gly
-10                  -5                 -1   1                 5

Phe Val Val Glu Pro His Thr Ser Ser Asp Gln Asn Gln Ala Ile Ile
                10                  15                  20

Ala Thr Phe Lys Asp Ala Ser Ile Glu Gly Tyr Gly Ile Lys Lys Arg
             25                  30                  35

Asp Glu Ala Thr Ala Lys Ala Glu Asp Leu Tyr Asp Gly Thr Gly
 40                  45                  50

Tyr Ile Ser Tyr Phe Phe Glu Glu Asp Glu Lys Ala Thr Val Gln Lys
 55                  60                  65                  70

Gly Ser Ala Thr Phe Gln Val Lys Ala Pro Glu Asn Gly Leu Tyr Glu
             75                  80                  85

Leu Ser Leu Gly Tyr Tyr Ile Pro Glu Gly Asn Gly Asp Lys Ala Thr
             90                  95                 100

Ser Ile Gln Val Asn Gly Ser Gly Ala Gly Glu Leu Thr Leu Ser Ala
            105                 110                 115

Pro Lys Pro Gly Thr Val Arg Ala Glu Lys Lys Met Thr Lys Val Leu
            120                 125                 130

Leu Asn Ser Gly Asn Asn Ser Ile Gln Ile Leu Arg Gly Trp Gly Tyr
135                 140                 145                 150

Tyr Gly Ile Glu Tyr Ile Lys Leu Glu Arg Val Glu Pro Arg Ile Thr
                155                 160                 165

Thr Gln Lys Thr Met Met Asp Pro Leu Ser Asn Ser Lys Ala Ser Pro
            170                 175                 180

Gln Ala Lys Ala Leu Met Lys Phe Met Thr Asn Gln Tyr Gly Lys Lys
            185                 190                 195

Ile Ile Ser Gly Gln Gln Thr Leu Glu Asp Ala Ala Trp Ile Tyr Gln
200                 205                 210

Gln Thr Gly Lys Tyr Pro Ala Leu Val Ser Ser Asp Leu Met Asp Tyr
215                 220                 225                 230

Ser Pro Ser Arg Val Glu Asn Gly Ser Thr Ser Asn Glu Val Glu Lys
            235                 240                 245

Met Met Glu Trp Tyr Lys Arg Gly Gly Ile Val Ser Leu Ser Trp His
            250                 255                 260

Trp Asn Ala Pro Lys Gly Ile Gly Ser Asn Glu Pro Gly His Glu Trp
            265                 270                 275

Trp Arg Gly Phe Asn Thr Glu Phe Thr Thr Phe Asp Val Glu Tyr Ala
            280                 285                 290

Leu Asn His Pro Glu Ser Glu Asp Tyr Lys Leu Leu Ile Arg Asp Ile
295                 300                 305                 310

Asp Ala Ile Ala Thr Gln Leu Lys Arg Leu Gln Glu His His Ile Pro
            315                 320                 325

Val Leu Trp Arg Pro Leu His Glu Ala Glu Gly Gly Trp Phe Trp Trp
            330                 335                 340

Gly Ala Lys Gly Pro Glu Pro Ala Lys Lys Leu Tyr Arg Leu Met Tyr
            345                 350                 355

Glu Arg Leu Thr Glu Lys His Gly Leu Asn Asn Leu Ile Trp Val Trp
360                 365                 370

Asn Ser Val Lys Glu Glu Trp Tyr Pro Gly Asp Asp Val Val Asp Met
```

```
375             380             385             390
Val Ser Val Asp Ile Tyr Asn Pro Pro Gly Asp Tyr Ser Pro Asn Ile
                395                 400             405

Ala Lys Tyr Asp Glu Leu Leu Phe Leu Ser Lys His Lys Lys Leu Val
                410             415             420

Ala Leu Ala Glu Asn Gly Pro Ile Pro Asp Pro Asp Leu Leu Gln Thr
                425             430             435

Tyr Gly Ala His Trp Ser Tyr Phe Asn Thr Trp Thr Gly Asp Val Leu
                440             445             450

Arg Asp Gly Lys Thr Asn Thr Lys Glu His Leu Lys Lys Val Tyr Asn
455             460             465             470

His Asp Asn Val Ile Thr Leu Asp Glu Leu Pro Lys Gly Leu Tyr Asp
                475             480             485

Ser Pro Arg Trp Lys
                490

<210> SEQ ID NO 3
<211> LENGTH: 491
<212> TYPE: PRT
<213> ORGANISM: Paenibacillus illinoisensis
<220> FEATURE:
<221> NAME/KEY: mat_peptide
<222> LOCATION: (1)..(491)

<400> SEQUENCE: 3

Ala Ile Thr Val Pro Gly Phe Val Val Glu Pro His Thr Ser Ser Asp
1               5                   10              15

Gln Asn Gln Ala Ile Ile Ala Thr Phe Lys Asp Ala Ser Ile Glu Gly
                20                  25                  30

Tyr Gly Ile Lys Lys Arg Asp Glu Ala Thr Ala Lys Ala Glu Asp Asp
                35                  40                  45

Leu Tyr Asp Gly Thr Gly Tyr Ile Ser Tyr Phe Phe Glu Glu Asp Glu
    50                  55                  60

Lys Ala Thr Val Gln Lys Gly Ser Ala Thr Phe Gln Val Lys Ala Pro
65              70                  75                  80

Glu Asn Gly Leu Tyr Glu Leu Ser Leu Gly Tyr Tyr Ile Pro Glu Gly
                85                  90                  95

Asn Gly Asp Lys Ala Thr Ser Ile Gln Val Asn Gly Ser Gly Ala Gly
                100                 105             110

Glu Leu Thr Leu Ser Ala Pro Lys Pro Gly Thr Val Arg Ala Glu Lys
                115             120                 125

Lys Met Thr Lys Val Leu Leu Asn Ser Gly Asn Asn Ser Ile Gln Ile
                130             135                 140

Leu Arg Gly Trp Gly Tyr Tyr Gly Ile Glu Tyr Ile Lys Leu Glu Arg
145                 150             155                 160

Val Glu Pro Arg Ile Thr Thr Gln Lys Thr Met Met Asp Pro Leu Ser
                165             170                 175

Asn Ser Lys Ala Ser Pro Gln Ala Lys Ala Leu Met Lys Phe Met Thr
                180             185                 190

Asn Gln Tyr Gly Lys Lys Ile Ile Ser Gly Gln Gln Thr Leu Glu Asp
                195             200                 205

Ala Ala Trp Ile Tyr Gln Gln Thr Gly Lys Tyr Pro Ala Leu Val Ser
                210             215                 220

Ser Asp Leu Met Asp Tyr Ser Pro Ser Arg Val Glu Asn Gly Ser Thr
225                 230             235                 240
```

Ser Asn Glu Val Glu Lys Met Met Glu Trp Tyr Lys Arg Gly Gly Ile
            245                 250                 255

Val Ser Leu Ser Trp His Trp Asn Ala Pro Lys Gly Ile Gly Ser Asn
        260                 265                 270

Glu Pro Gly His Glu Trp Trp Arg Gly Phe Asn Thr Glu Phe Thr Thr
    275                 280                 285

Phe Asp Val Glu Tyr Ala Leu Asn His Pro Glu Ser Glu Asp Tyr Lys
290                 295                 300

Leu Leu Ile Arg Asp Ile Asp Ala Ile Ala Thr Gln Leu Lys Arg Leu
305                 310                 315                 320

Gln Glu His His Ile Pro Val Leu Trp Arg Pro Leu His Glu Ala Glu
                325                 330                 335

Gly Gly Trp Phe Trp Trp Gly Ala Lys Gly Pro Glu Pro Ala Lys Lys
            340                 345                 350

Leu Tyr Arg Leu Met Tyr Glu Arg Leu Thr Glu Lys His Gly Leu Asn
        355                 360                 365

Asn Leu Ile Trp Val Trp Asn Ser Val Lys Glu Trp Tyr Pro Gly
    370                 375                 380

Asp Asp Val Val Asp Met Val Ser Val Asp Ile Tyr Asn Pro Pro Gly
385                 390                 395                 400

Asp Tyr Ser Pro Asn Ile Ala Lys Tyr Asp Glu Leu Leu Phe Leu Ser
                405                 410                 415

Lys His Lys Lys Leu Val Ala Leu Ala Glu Asn Gly Pro Ile Pro Asp
            420                 425                 430

Pro Asp Leu Leu Gln Thr Tyr Gly Ala His Trp Ser Tyr Phe Asn Thr
        435                 440                 445

Trp Thr Gly Asp Val Leu Arg Asp Gly Lys Thr Asn Thr Lys Glu His
    450                 455                 460

Leu Lys Lys Val Tyr Asn His Asp Asn Val Ile Thr Leu Asp Glu Leu
465                 470                 475                 480

Pro Lys Gly Leu Tyr Asp Ser Pro Arg Trp Lys
                485                 490

<210> SEQ ID NO 4
<211> LENGTH: 312
<212> TYPE: PRT
<213> ORGANISM: Paenibacillus illinoisensis
<220> FEATURE:
<221> NAME/KEY: mat_paptide
<222> LOCATION: (1)..(312)

<400> SEQUENCE: 4

Ala Ser Pro Gln Ala Lys Ala Leu Met Lys Phe Met Thr Asn Gln Tyr
1               5                   10                  15

Gly Lys Lys Ile Ile Ser Gly Gln Gln Thr Leu Glu Asp Ala Ala Trp
            20                  25                  30

Ile Tyr Gln Gln Thr Gly Lys Tyr Pro Ala Leu Val Ser Ser Asp Leu
        35                  40                  45

Met Asp Tyr Ser Pro Ser Arg Val Glu Asn Gly Ser Thr Ser Asn Glu
    50                  55                  60

Val Glu Lys Met Met Glu Trp Tyr Lys Arg Gly Gly Ile Val Ser Leu
65                  70                  75                  80

Ser Trp His Trp Asn Ala Pro Lys Gly Ile Gly Ser Asn Glu Pro Gly
                85                  90                  95

His Glu Trp Trp Arg Gly Phe Asn Thr Glu Phe Thr Thr Phe Asp Val
            100                 105                 110

```
Glu Tyr Ala Leu Asn His Pro Glu Ser Glu Asp Tyr Lys Leu Leu Ile
            115                 120                 125

Arg Asp Ile Asp Ala Ile Ala Thr Gln Leu Lys Arg Leu Gln Glu His
    130                 135                 140

His Ile Pro Val Leu Trp Arg Pro Leu His Glu Ala Glu Gly Gly Trp
145                 150                 155                 160

Phe Trp Trp Gly Ala Lys Gly Pro Glu Pro Ala Lys Lys Leu Tyr Arg
                165                 170                 175

Leu Met Tyr Glu Arg Leu Thr Glu Lys His Gly Leu Asn Asn Leu Ile
            180                 185                 190

Trp Val Trp Asn Ser Val Lys Glu Trp Tyr Pro Gly Asp Asp Val
        195                 200                 205

Val Asp Met Val Ser Val Asp Ile Tyr Asn Pro Pro Gly Asp Tyr Ser
    210                 215                 220

Pro Asn Ile Ala Lys Tyr Asp Glu Leu Leu Phe Leu Ser Lys His Lys
225                 230                 235                 240

Lys Leu Val Ala Leu Ala Glu Asn Gly Pro Ile Pro Asp Pro Asp Leu
                245                 250                 255

Leu Gln Thr Tyr Gly Ala His Trp Ser Tyr Phe Asn Thr Trp Thr Gly
            260                 265                 270

Asp Val Leu Arg Asp Gly Lys Thr Asn Thr Lys Glu His Leu Lys Lys
    275                 280                 285

Val Tyr Asn His Asp Asn Val Ile Thr Leu Asp Glu Leu Pro Lys Gly
290                 295                 300

Leu Tyr Asp Ser Pro Arg Trp Lys
305                 310
```

```
<210> SEQ ID NO 5
<211> LENGTH: 1575
<212> TYPE: DNA
<213> ORGANISM: Artificial Sequence
<220> FEATURE:
<223> OTHER INFORMATION: Construct DNA sequence of the GH26 mannanase
      comprising a CBM35 wherein the native secretion signal was
      replaced with a Bacillus clausii secretion signal and a 6xHis tag
      was added directly on the C-terminal of the protein
<220> FEATURE:
<221> NAME/KEY: CDS
<222> LOCATION: (1)..(1572)
<220> FEATURE:
<221> NAME/KEY: sig_peptide
<222> LOCATION: (1)..(81)
<220> FEATURE:
<221> NAME/KEY: mat_peptide
<222> LOCATION: (82)..(1572)

<400> SEQUENCE: 5
```

```
atg aag aaa ccg ttg ggg aaa att gtc gca agc acc gca cta ctc att      48
Met Lys Lys Pro Leu Gly Lys Ile Val Ala Ser Thr Ala Leu Leu Ile
    -25                 -20                 -15 tct gtt gct ttt agt tca tcg ata gca tca gca gct att acg gta ccg      96
Ser Val Ala Phe Ser Ser Ser Ile Ala Ser Ala Ala Ile Thr Val Pro
        -10                 -5              -1  1               5 gga ttt gtt gtt gaa ccc cat act tct tct gat caa aac cag gcc ata     144
Gly Phe Val Val Glu Pro His Thr Ser Ser Asp Gln Asn Gln Ala Ile
                10                  15                  20 ata gcc aca ttc aaa gat gct tcc atc gaa ggg tac ggg atc aag aaa     192
Ile Ala Thr Phe Lys Asp Ala Ser Ile Glu Gly Tyr Gly Ile Lys Lys
            25                  30                  35 cgc gat gag gca aca gcc aaa gcg gag gac gat cta tat gat ggt aca     240
```

```
        Arg Asp Glu Ala Thr Ala Lys Ala Glu Asp Asp Leu Tyr Asp Gly Thr
                    40                  45                  50 ggt tat atc tct tat ttt ttt gaa gag gat gaa aag gcc aca gtt cag      288
Gly Tyr Ile Ser Tyr Phe Phe Glu Glu Asp Glu Lys Ala Thr Val Gln
        55                  60                  65 aag gga agc gct aca ttc cag gtt aaa gca ccg gaa aat ggg ctt tat      336
Lys Gly Ser Ala Thr Phe Gln Val Lys Ala Pro Glu Asn Gly Leu Tyr
70                  75                  80                  85 gag tta agt ttg gga tac tac atc cca gaa gga aat ggg gat aaa gcg      384
Glu Leu Ser Leu Gly Tyr Tyr Ile Pro Glu Gly Asn Gly Asp Lys Ala
                    90                  95                 100 act tcc atc caa gta aat ggt tcg gga gcc ggg gag ctg acg ctc agt      432
Thr Ser Ile Gln Val Asn Gly Ser Gly Ala Gly Glu Leu Thr Leu Ser
                   105                 110                 115 gcg cca aag cca ggg acg gtt cga gca gaa aaa aag atg aca aag gtg      480
Ala Pro Lys Pro Gly Thr Val Arg Ala Glu Lys Lys Met Thr Lys Val
                   120                 125                 130 ctt ctg aac agc ggt aac aac tcc att caa ata tta agg ggg tgg ggg      528
Leu Leu Asn Ser Gly Asn Asn Ser Ile Gln Ile Leu Arg Gly Trp Gly
135                 140                 145 tac tat ggc att gag tat atc aag ctt gaa cgt gta gaa ccc cgc ata      576
Tyr Tyr Gly Ile Glu Tyr Ile Lys Leu Glu Arg Val Glu Pro Arg Ile
150                 155                 160                 165 acc acg caa aaa aca atg atg gat ccc tta agt aac tcc aaa gca tct      624
Thr Thr Gln Lys Thr Met Met Asp Pro Leu Ser Asn Ser Lys Ala Ser
                   170                 175                 180 ccg caa gcc aaa gca tta atg aaa ttt atg acc aac cag tat gga aaa      672
Pro Gln Ala Lys Ala Leu Met Lys Phe Met Thr Asn Gln Tyr Gly Lys
                   185                 190                 195 aaa att ata tca ggc cag caa acc cta gag gac gca gcg tgg atc tat      720
Lys Ile Ile Ser Gly Gln Gln Thr Leu Glu Asp Ala Ala Trp Ile Tyr
                   200                 205                 210 cag cag act gga aag tac cct gca ctg gtt tcc agt gat ttg atg gat      768
Gln Gln Thr Gly Lys Tyr Pro Ala Leu Val Ser Ser Asp Leu Met Asp
            215                 220                 225 tat tct cca tcc cgt gtg gaa aac gga agc acc tcg aat gag gta gaa      816
Tyr Ser Pro Ser Arg Val Glu Asn Gly Ser Thr Ser Asn Glu Val Glu
230                 235                 240                 245 aag atg atg gag tgg tac aag cgt gga ggc att gtc tcc tta agc tgg      864
Lys Met Met Glu Trp Tyr Lys Arg Gly Gly Ile Val Ser Leu Ser Trp
                   250                 255                 260 cac tgg aat gcg ccg aaa ggg atc ggc agc aat gaa cca ggc cat gag      912
His Trp Asn Ala Pro Lys Gly Ile Gly Ser Asn Glu Pro Gly His Glu
                   265                 270                 275 tgg tgg cgg ggg ttc aat aca gag ttc aca acc ttc gat gta gaa tat      960
Trp Trp Arg Gly Phe Asn Thr Glu Phe Thr Thr Phe Asp Val Glu Tyr
            280                 285                 290 gct ctg aat cat ccg gaa tcg gaa gat tac aag ctt cta att cgg gat     1008
Ala Leu Asn His Pro Glu Ser Glu Asp Tyr Lys Leu Leu Ile Arg Asp
        295                 300                 305 att gat gcg atc gct act caa ttg aag cgg ctg cag gag cac cat att     1056
Ile Asp Ala Ile Ala Thr Gln Leu Lys Arg Leu Gln Glu His His Ile
310                 315                 320                 325 ccc gta ctt tgg aga cca ctg cat gaa gcg gag ggt ggc tgg ttt tgg     1104
Pro Val Leu Trp Arg Pro Leu His Glu Ala Glu Gly Gly Trp Phe Trp
                   330                 335                 340 tgg gga gcc aaa ggt cct gaa cct gcg aaa aaa ttg tat cga tta atg     1152
Trp Gly Ala Lys Gly Pro Glu Pro Ala Lys Lys Leu Tyr Arg Leu Met
                   345                 350                 355
```

```
tac gaa cga ttg acg gag aag cat ggg tta aac aat ctc att tgg gtt    1200
Tyr Glu Arg Leu Thr Glu Lys His Gly Leu Asn Asn Leu Ile Trp Val
        360                 365                 370 tgg aac tct gtt aag gag gag tgg tac ccg gga gat gat gtg gtg gat    1248
Trp Asn Ser Val Lys Glu Glu Trp Tyr Pro Gly Asp Asp Val Val Asp
375                 380                 385 atg gta agt gtc gac att tat aat cca ccc ggt gat tac agc ccg aac    1296
Met Val Ser Val Asp Ile Tyr Asn Pro Pro Gly Asp Tyr Ser Pro Asn
390                 395                 400                 405 att gcc aag tac gac gag ctc ttt ctg agc aag cat aag aaa ctt        1344
Ile Ala Lys Tyr Asp Glu Leu Phe Leu Ser Lys His Lys Lys Leu
            410                 415                 420 gtg gca ctc gcc gaa aat ggg ccg att ccc gat cct gat ctg ctg cag    1392
Val Ala Leu Ala Glu Asn Gly Pro Ile Pro Asp Pro Asp Leu Leu Gln
                425                 430                 435 aca tac ggt gca cat tgg agc tat ttt aat acc tgg act ggc gat gtt    1440
Thr Tyr Gly Ala His Trp Ser Tyr Phe Asn Thr Trp Thr Gly Asp Val
        440                 445                 450 ctg cgt gat gga aaa acg aat aca aag gaa cat ttg aaa aaa gtc tac    1488
Leu Arg Asp Gly Lys Thr Asn Thr Lys Glu His Leu Lys Lys Val Tyr
455                 460                 465 aat cat gac aac gtg atc aca ctg gat gaa ctt ccc aag gga ttg tac    1536
Asn His Asp Asn Val Ile Thr Leu Asp Glu Leu Pro Lys Gly Leu Tyr
470                 475                 480                 485 gac agt cct aga tgg aaa cat cat cac cat cac cac taa                1575
Asp Ser Pro Arg Trp Lys His His His His His His
                490                 495

<210> SEQ ID NO 6
<211> LENGTH: 524
<212> TYPE: PRT
<213> ORGANISM: Artificial Sequence
<220> FEATURE:
<223> OTHER INFORMATION: Synthetic Construct

<400> SEQUENCE: 6

Met Lys Lys Pro Leu Gly Lys Ile Val Ala Ser Thr Ala Leu Leu Ile
            -25                 -20                 -15

Ser Val Ala Phe Ser Ser Ile Ala Ser Ala Ala Ile Thr Val Pro
    -10                  -5              -1   1                   5

Gly Phe Val Val Glu Pro His Thr Ser Ser Asp Gln Asn Gln Ala Ile
                10                  15                  20

Ile Ala Thr Phe Lys Asp Ala Ser Ile Glu Gly Tyr Gly Ile Lys Lys
            25                  30                  35

Arg Asp Glu Ala Thr Ala Lys Ala Glu Asp Asp Leu Tyr Asp Gly Thr
        40                  45                  50

Gly Tyr Ile Ser Tyr Phe Phe Glu Glu Asp Glu Lys Ala Thr Val Gln
    55                  60                  65

Lys Gly Ser Ala Thr Phe Gln Val Lys Ala Pro Glu Asn Gly Leu Tyr
70                  75                  80                  85

Glu Leu Ser Leu Gly Tyr Tyr Ile Pro Glu Gly Asn Gly Asp Lys Ala
                90                  95                  100

Thr Ser Ile Gln Val Asn Gly Ser Gly Ala Gly Glu Leu Thr Leu Ser
            105                 110                 115

Ala Pro Lys Pro Gly Thr Val Arg Ala Glu Lys Lys Met Thr Lys Val
        120                 125                 130

Leu Leu Asn Ser Gly Asn Asn Ser Ile Gln Ile Leu Arg Gly Trp Gly
    135                 140                 145
```

Tyr Tyr Gly Ile Glu Tyr Ile Lys Leu Glu Arg Val Glu Pro Arg Ile
150                 155                 160                 165

Thr Thr Gln Lys Thr Met Met Asp Pro Leu Ser Asn Ser Lys Ala Ser
            170                 175                 180

Pro Gln Ala Lys Ala Leu Met Lys Phe Met Thr Asn Gln Tyr Gly Lys
                185                 190                 195

Lys Ile Ile Ser Gly Gln Gln Thr Leu Glu Asp Ala Ala Trp Ile Tyr
            200                 205                 210

Gln Gln Thr Gly Lys Tyr Pro Ala Leu Val Ser Ser Asp Leu Met Asp
        215                 220                 225

Tyr Ser Pro Ser Arg Val Glu Asn Gly Ser Thr Ser Asn Glu Val Glu
230                 235                 240                 245

Lys Met Met Glu Trp Tyr Lys Arg Gly Ile Val Ser Leu Ser Trp
                250                 255                 260

His Trp Asn Ala Pro Lys Gly Ile Gly Ser Asn Glu Pro Gly His Glu
                265                 270                 275

Trp Trp Arg Gly Phe Asn Thr Glu Phe Thr Thr Phe Asp Val Glu Tyr
            280                 285                 290

Ala Leu Asn His Pro Glu Ser Glu Asp Tyr Lys Leu Leu Ile Arg Asp
        295                 300                 305

Ile Asp Ala Ile Ala Thr Gln Leu Lys Arg Leu Gln Glu His His Ile
310                 315                 320                 325

Pro Val Leu Trp Arg Pro Leu His Glu Ala Glu Gly Gly Trp Phe Trp
                330                 335                 340

Trp Gly Ala Lys Gly Pro Glu Pro Ala Lys Lys Leu Tyr Arg Leu Met
            345                 350                 355

Tyr Glu Arg Leu Thr Glu Lys His Gly Leu Asn Asn Leu Ile Trp Val
        360                 365                 370

Trp Asn Ser Val Lys Glu Glu Trp Tyr Pro Gly Asp Val Val Asp
375                 380                 385

Met Val Ser Val Asp Ile Tyr Asn Pro Pro Gly Asp Tyr Ser Pro Asn
390                 395                 400                 405

Ile Ala Lys Tyr Asp Glu Leu Leu Phe Leu Ser Lys His Lys Lys Leu
                410                 415                 420

Val Ala Leu Ala Glu Asn Gly Pro Ile Pro Asp Pro Asp Leu Leu Gln
            425                 430                 435

Thr Tyr Gly Ala His Trp Ser Tyr Phe Asn Thr Trp Thr Gly Asp Val
        440                 445                 450

Leu Arg Asp Gly Lys Thr Asn Thr Lys Glu His Leu Lys Lys Val Tyr
    455                 460                 465

Asn His Asp Asn Val Ile Thr Leu Asp Glu Leu Pro Lys Gly Leu Tyr
470                 475                 480                 485

Asp Ser Pro Arg Trp Lys His His His His His
                490                 495

<210> SEQ ID NO 7
<211> LENGTH: 1044
<212> TYPE: DNA
<213> ORGANISM: Artificial Sequence
<220> FEATURE:
<223> OTHER INFORMATION: Construct DNA sequence of the truncated GH26
      mannanase missing the CBM35 domain wherein the native secretion
      signal was replaced with a Bacillus licheniformis secretion signal
      and a 6xHis tag was added directly on the C-terminal of the
      protein..
<220> FEATURE:
<221> NAME/KEY: CDS

```
<222> LOCATION: (1)..(1041)
<220> FEATURE:
<221> NAME/KEY: sig_peptide
<222> LOCATION: (1)..(87)
<220> FEATURE:
<221> NAME/KEY: mat_peptide
<222> LOCATION: (88)..(1041)

<400> SEQUENCE: 7
```

| | | | | | | | | | | | | | | | | |
|---|---|---|---|---|---|---|---|---|---|---|---|---|---|---|---|---|
| atg | aaa | caa | caa | aaa | cgg | ctt | tac | gcc | cga | ttg | ctg | acg | ctg | tta | ttt | 48 |
| Met | Lys | Gln | Gln | Lys | Arg | Leu | Tyr | Ala | Arg | Leu | Leu | Thr | Leu | Leu | Phe | |
| | | | -25 | | | | -20 | | | | | -15 | | | | |
| gcg | ctc | atc | ttc | ttg | ctg | cct | cat | tct | gca | gca | gcg | gca | tct | ccg | | 96 |
| Ala | Leu | Ile | Phe | Leu | Leu | Pro | His | Ser | Ala | Ala | Ala | Ala | Ser | Pro | | |
| | | | -10 | | | | -5 | | | | -1 | 1 | | | | |
| caa | gcc | aaa | gca | tta | atg | aaa | ttt | atg | acc | aac | cag | tat | gga | aaa | aaa | 144 |
| Gln | Ala | Lys | Ala | Leu | Met | Lys | Phe | Met | Thr | Asn | Gln | Tyr | Gly | Lys | Lys | |
| | 5 | | | | 10 | | | | | 15 | | | | | | |
| att | ata | tca | ggc | cag | caa | acc | cta | gag | gac | gca | gcg | tgg | atc | tat | cag | 192 |
| Ile | Ile | Ser | Gly | Gln | Gln | Thr | Leu | Glu | Asp | Ala | Ala | Trp | Ile | Tyr | Gln | |
| 20 | | | | | 25 | | | | | 30 | | | | | 35 | |
| cag | act | gga | aag | tac | cct | gca | ctg | gtt | tcc | agt | gat | ttg | atg | gat | tat | 240 |
| Gln | Thr | Gly | Lys | Tyr | Pro | Ala | Leu | Val | Ser | Ser | Asp | Leu | Met | Asp | Tyr | |
| | | | | 40 | | | | | 45 | | | | | 50 | | |
| tct | cca | tcc | cgt | gtg | gaa | aac | gga | agc | acc | tcg | aat | gag | gta | gaa | aag | 288 |
| Ser | Pro | Ser | Arg | Val | Glu | Asn | Gly | Ser | Thr | Ser | Asn | Glu | Val | Glu | Lys | |
| | | | 55 | | | | | 60 | | | | | 65 | | | |
| atg | atg | gag | tgg | tac | aag | cgt | gga | ggc | att | gtc | tcc | tta | agc | tgg | cac | 336 |
| Met | Met | Glu | Trp | Tyr | Lys | Arg | Gly | Gly | Ile | Val | Ser | Leu | Ser | Trp | His | |
| | | 70 | | | | | 75 | | | | | 80 | | | | |
| tgg | aat | gcg | ccg | aaa | ggg | atc | ggc | agc | aat | gaa | cca | ggc | cat | gag | tgg | 384 |
| Trp | Asn | Ala | Pro | Lys | Gly | Ile | Gly | Ser | Asn | Glu | Pro | Gly | His | Glu | Trp | |
| | 85 | | | | | 90 | | | | | 95 | | | | | |
| tgg | cgg | ggg | ttc | aat | aca | gag | ttc | aca | acc | ttc | gat | gta | gaa | tat | gct | 432 |
| Trp | Arg | Gly | Phe | Asn | Thr | Glu | Phe | Thr | Thr | Phe | Asp | Val | Glu | Tyr | Ala | |
| 100 | | | | | 105 | | | | | 110 | | | | | 115 | |
| ctg | aat | cat | ccg | gaa | tcg | gaa | gat | tac | aag | ctt | cta | att | cgg | gat | att | 480 |
| Leu | Asn | His | Pro | Glu | Ser | Glu | Asp | Tyr | Lys | Leu | Leu | Ile | Arg | Asp | Ile | |
| | | | | 120 | | | | | 125 | | | | | 130 | | |
| gat | gcg | atc | gct | act | caa | ttg | aag | cgg | ctg | cag | gag | cac | cat | att | ccc | 528 |
| Asp | Ala | Ile | Ala | Thr | Gln | Leu | Lys | Arg | Leu | Gln | Glu | His | His | Ile | Pro | |
| | | | 135 | | | | | 140 | | | | | 145 | | | |
| gta | ctt | tgg | aga | cca | ctg | cat | gaa | gcg | gag | ggt | ggc | tgg | ttt | tgg | tgg | 576 |
| Val | Leu | Trp | Arg | Pro | Leu | His | Glu | Ala | Glu | Gly | Gly | Trp | Phe | Trp | Trp | |
| | | 150 | | | | | 155 | | | | | 160 | | | | |
| gga | gcc | aaa | ggt | cct | gaa | cct | gcg | aaa | aaa | ttg | tat | cga | tta | atg | tac | 624 |
| Gly | Ala | Lys | Gly | Pro | Glu | Pro | Ala | Lys | Lys | Leu | Tyr | Arg | Leu | Met | Tyr | |
| | 165 | | | | | 170 | | | | | 175 | | | | | |
| gaa | cga | ttg | acg | gag | aag | cat | ggg | tta | aac | aat | ctc | att | tgg | gtt | tgg | 672 |
| Glu | Arg | Leu | Thr | Glu | Lys | His | Gly | Leu | Asn | Asn | Leu | Ile | Trp | Val | Trp | |
| 180 | | | | | 185 | | | | | 190 | | | | | 195 | |
| aac | tct | gtt | aag | gag | gag | tgg | tac | ccg | gga | gat | gat | gtg | gtg | gat | atg | 720 |
| Asn | Ser | Val | Lys | Glu | Glu | Trp | Tyr | Pro | Gly | Asp | Asp | Val | Val | Asp | Met | |
| | | | | 200 | | | | | 205 | | | | | 210 | | |
| gta | agt | gtc | gac | att | tat | aat | cca | ccc | ggt | gat | tac | agc | ccg | aac | att | 768 |
| Val | Ser | Val | Asp | Ile | Tyr | Asn | Pro | Pro | Gly | Asp | Tyr | Ser | Pro | Asn | Ile | |
| | | | 215 | | | | | 220 | | | | | 225 | | | |
| gcc | aag | tac | gac | gag | ctc | ttg | ttt | ctg | agc | aag | cat | aag | aaa | ctt | gtg | 816 |
| Ala | Lys | Tyr | Asp | Glu | Leu | Leu | Phe | Leu | Ser | Lys | His | Lys | Lys | Leu | Val | |
| | | 230 | | | | | 235 | | | | | 240 | | | | |
| gca | ctc | gcc | gaa | aat | ggg | ccg | att | ccc | gat | cct | gat | ctg | ctg | cag | aca | 864 |

```
Ala Leu Ala Glu Asn Gly Pro Ile Pro Asp Pro Leu Leu Gln Thr
        245                 250                 255 tac ggt gca cat tgg agc tat ttt aat acc tgg act ggc gat gtt ctg      912
Tyr Gly Ala His Trp Ser Tyr Phe Asn Thr Trp Thr Gly Asp Val Leu
260                 265                 270                 275 cgt gat gga aaa acg aat aca aag gaa cat ttg aaa aaa gtc tac aat      960
Arg Asp Gly Lys Thr Asn Thr Lys Glu His Leu Lys Lys Val Tyr Asn
                280                 285                 290 cat gac aac gtg atc aca ctg gat gaa ctt ccc aag gga ttg tac gac     1008
His Asp Asn Val Ile Thr Leu Asp Glu Leu Pro Lys Gly Leu Tyr Asp
                295                 300                 305 agt cct aga tgg aaa cat cat cac cat cac cac taa                     1044
Ser Pro Arg Trp Lys His His His His His His
        310                 315

<210> SEQ ID NO 8
<211> LENGTH: 347
<212> TYPE: PRT
<213> ORGANISM: Artificial Sequence
<220> FEATURE:
<223> OTHER INFORMATION: Synthetic Construct

<400> SEQUENCE: 8

Met Lys Gln Gln Lys Arg Leu Tyr Ala Arg Leu Leu Thr Leu Leu Phe
            -25                 -20                 -15

Ala Leu Ile Phe Leu Leu Pro His Ser Ala Ala Ala Ala Ser Pro
        -10                  -5              -1   1

Gln Ala Lys Ala Leu Met Lys Phe Met Thr Asn Gln Tyr Gly Lys Lys
    5                   10                  15

Ile Ile Ser Gly Gln Gln Thr Leu Glu Asp Ala Ala Trp Ile Tyr Gln
20                  25                  30                  35

Gln Thr Gly Lys Tyr Pro Ala Leu Val Ser Ser Asp Leu Met Asp Tyr
                40                  45                  50

Ser Pro Ser Arg Val Glu Asn Gly Ser Thr Ser Asn Glu Val Glu Lys
            55                  60                  65

Met Met Glu Trp Tyr Lys Arg Gly Gly Ile Val Ser Leu Ser Trp His
        70                  75                  80

Trp Asn Ala Pro Lys Gly Ile Gly Ser Asn Glu Pro Gly His Glu Trp
    85                  90                  95

Trp Arg Gly Phe Asn Thr Glu Phe Thr Thr Phe Asp Val Glu Tyr Ala
100                 105                 110                 115

Leu Asn His Pro Glu Ser Glu Asp Tyr Lys Leu Leu Ile Arg Asp Ile
                120                 125                 130

Asp Ala Ile Ala Thr Gln Leu Lys Arg Leu Gln Glu His His Ile Pro
            135                 140                 145

Val Leu Trp Arg Pro Leu His Glu Ala Glu Gly Gly Trp Phe Trp Trp
        150                 155                 160

Gly Ala Lys Gly Pro Glu Pro Ala Lys Lys Leu Tyr Arg Leu Met Tyr
    165                 170                 175

Glu Arg Leu Thr Glu Lys His Gly Leu Asn Asn Leu Ile Trp Val Trp
180                 185                 190                 195

Asn Ser Val Lys Glu Glu Trp Tyr Pro Gly Asp Val Asp Met
                200                 205                 210

Val Ser Val Asp Ile Tyr Asn Pro Pro Gly Asp Tyr Ser Pro Asn Ile
            215                 220                 225

Ala Lys Tyr Asp Glu Leu Leu Phe Leu Ser Lys His Lys Lys Leu Val
        230                 235                 240
```

```
                    Ala Leu Ala Glu Asn Gly Pro Ile Pro Asp Pro Asp Leu Leu Gln Thr
                                245                 250                 255

Tyr Gly Ala His Trp Ser Tyr Phe Asn Thr Trp Thr Gly Asp Val Leu
                    260                 265                 270                 275

Arg Asp Gly Lys Thr Asn Thr Lys Glu His Leu Lys Lys Val Tyr Asn
                                    280                 285                 290

His Asp Asn Val Ile Thr Leu Asp Glu Leu Pro Lys Gly Leu Tyr Asp
                                295                 300                 305

Ser Pro Arg Trp Lys His His His His His
                                310                 315

<210> SEQ ID NO 9
<211> LENGTH: 27
<212> TYPE: PRT
<213> ORGANISM: Bacillus clausii

<400> SEQUENCE: 9

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 10
<211> LENGTH: 29
<212> TYPE: PRT
<213> ORGANISM: Bacillus licheniformis

<400> SEQUENCE: 10

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala
            20                  25

<210> SEQ ID NO 11
<211> LENGTH: 1602
<212> TYPE: DNA
<213> ORGANISM: Paenibacillus sp.
<220> FEATURE:
<221> NAME/KEY: CDS
<222> LOCATION: (1)..(1599)
<220> FEATURE:
<221> NAME/KEY: sig_peptide
<222> LOCATION: (1)..(126)
<220> FEATURE:
<221> NAME/KEY: mat_peptide
<222> LOCATION: (127)..(1599)

<400> SEQUENCE: 11 atg aag gca aaa tca gat tcg ctt att aga tgt tca aca tca aat aaa        48
Met Lys Ala Lys Ser Asp Ser Leu Ile Arg Cys Ser Thr Ser Asn Lys
        -40                 -35                 -30 acg tat ttt atg ttt ggg tcg gcc att ttc gtt ctg tat atc ctc atg        96
Thr Tyr Phe Met Phe Gly Ser Ala Ile Phe Val Leu Tyr Ile Leu Met
    -25                 -20                 -15 ttg agt ttt act cat tcc agg gtg gaa gca gct att acg gta ccg gga       144
Leu Ser Phe Thr His Ser Arg Val Glu Ala Ala Ile Thr Val Pro Gly
-10                 -5                  -1  1               5 ttt gtc gtt gaa ccc cat act tct tct gat caa aac cag gcc ata ata       192
Phe Val Val Glu Pro His Thr Ser Ser Asp Gln Asn Gln Ala Ile Ile
                10                  15                  20 gcc aca tac aat gat gct tca atc gaa ggg tac ggg att aag aaa cgt       240
Ala Thr Tyr Asn Asp Ala Ser Ile Glu Gly Tyr Gly Ile Lys Lys Arg
```

-continued

```
              25                  30                  35
gat gag aca aca gcc aaa gcg gag gac gat tta tat gat ggc aca ggg    288
Asp Glu Thr Thr Ala Lys Ala Glu Asp Asp Leu Tyr Asp Gly Thr Gly
        40                  45                  50 tat atc tct tat ttt ttt gaa gag gat gaa aag gcc aca gct cag aag    336
Tyr Ile Ser Tyr Phe Phe Glu Glu Asp Glu Lys Ala Thr Ala Gln Lys
55                  60                  65                  70 ggg agt gct aca ttc cac gtt aaa gca cct gaa aat ggg ctt tat gag    384
Gly Ser Ala Thr Phe His Val Lys Ala Pro Glu Asn Gly Leu Tyr Glu
                75                  80                  85 tta agt ttg gga tac tac atc cct gaa gga aat ggg gat aaa gcg act    432
Leu Ser Leu Gly Tyr Tyr Ile Pro Glu Gly Asn Gly Asp Lys Ala Thr
            90                  95                 100 tct atc caa gtg aat ggt tcg gga gcc ggc gag ttg atg ctc agt gcg    480
Ser Ile Gln Val Asn Gly Ser Gly Ala Gly Glu Leu Met Leu Ser Ala
        105                 110                 115 cca aag caa ggg acg gtt cga gca gaa aaa aag atg aca aag gtg ctt    528
Pro Lys Gln Gly Thr Val Arg Ala Glu Lys Lys Met Thr Lys Val Leu
120                 125                 130 ctg aac agc ggt aac aac tcc att caa ata tta agg ggg tgg ggg tac    576
Leu Asn Ser Gly Asn Asn Ser Ile Gln Ile Leu Arg Gly Trp Gly Tyr
135                 140                 145                 150 tat ggc att gaa tat atc aag ctt gaa cgt gta gaa ccc cgc ata acc    624
Tyr Gly Ile Glu Tyr Ile Lys Leu Glu Arg Val Glu Pro Arg Ile Thr
                155                 160                 165 acg caa aaa aca aag atg gat ccc tta agc aac tcc aaa gca tct ccg    672
Thr Gln Lys Thr Lys Met Asp Pro Leu Ser Asn Ser Lys Ala Ser Pro
            170                 175                 180 caa gcc aaa gca tta atg aaa ttt atg acc aac cag tat gga aaa aag    720
Gln Ala Lys Ala Leu Met Lys Phe Met Thr Asn Gln Tyr Gly Lys Lys
        185                 190                 195 att ata tca ggg cag caa acc cta gag gac gca acg tgg atc tat cag    768
Ile Ile Ser Gly Gln Gln Thr Leu Glu Asp Ala Thr Trp Ile Tyr Gln
200                 205                 210 cag aca ggt aag tac cct gca ctg gtt tcc agt gat ttg atg gat tat    816
Gln Thr Gly Lys Tyr Pro Ala Leu Val Ser Ser Asp Leu Met Asp Tyr
215                 220                 225                 230 tct cca tcc cgt gtg gaa aac gga agc acc tcg aat gag gta gaa aag    864
Ser Pro Ser Arg Val Glu Asn Gly Ser Thr Ser Asn Glu Val Glu Lys
                235                 240                 245 atg atg gag tgg tac aag cgt gga gga att gtc tcc tta agc tgg cac    912
Met Met Glu Trp Tyr Lys Arg Gly Gly Ile Val Ser Leu Ser Trp His
            250                 255                 260 tgg aat gcg ccg aaa ggg atc ggc ggc aat gaa cca ggc cac gag tgg    960
Trp Asn Ala Pro Lys Gly Ile Gly Gly Asn Glu Pro Gly His Glu Trp
        265                 270                 275 tgg cgg ggg ttt aat aca gaa ttc aca acc ttc gat gta gaa tat gcc    1008
Trp Arg Gly Phe Asn Thr Glu Phe Thr Thr Phe Asp Val Glu Tyr Ala
280                 285                 290 ttg gat cat ccg gaa tcg gaa gat tac aag ctt tta atc cgg gat att    1056
Leu Asp His Pro Glu Ser Glu Asp Tyr Lys Leu Leu Ile Arg Asp Ile
295                 300                 305                 310 gat gcg atc gct gct caa ttg aag cgg ctg cag gaa cac cat att ccc    1104
Asp Ala Ile Ala Ala Gln Leu Lys Arg Leu Gln Glu His His Ile Pro
                315                 320                 325 gta ctt tgg aga ccg ttg cat gaa gcg gag ggc ggc tgg ttt tgg tgg    1152
Val Leu Trp Arg Pro Leu His Glu Ala Glu Gly Gly Trp Phe Trp Trp
            330                 335                 340 gga gcc aaa ggt cct gag cct gcc aag aaa ttg tat aga tta atg tac    1200
```

```
Gly Ala Lys Gly Pro Glu Pro Ala Lys Lys Leu Tyr Arg Leu Met Tyr
            345                 350                 355 gaa cga ttg acg gaa aag cac aag tta aac aat ctc att tgg gtt tgg      1248
Glu Arg Leu Thr Glu Lys His Lys Leu Asn Asn Leu Ile Trp Val Trp
        360                 365                 370 aac tct gtt aag gag gag tgg tac ccg gga gat gat gtg gtg gat atg      1296
Asn Ser Val Lys Glu Glu Trp Tyr Pro Gly Asp Asp Val Val Asp Met
375                 380                 385                 390 gta agt gtc gac att tat aat cca ccc ggt gat cac agc cca agc att      1344
Val Ser Val Asp Ile Tyr Asn Pro Pro Gly Asp His Ser Pro Ser Ile
                395                 400                 405 gcc aag tac gac gag ctc ttg ttt ctg agc aag cat aag aaa ctt gtg      1392
Ala Lys Tyr Asp Glu Leu Leu Phe Leu Ser Lys His Lys Lys Leu Val
            410                 415                 420 gca ctc gcc gaa aat ggg ccg att ccc gat cct gat ctg ctg cag act      1440
Ala Leu Ala Glu Asn Gly Pro Ile Pro Asp Pro Asp Leu Leu Gln Thr
        425                 430                 435 tac ggt gca cat tgg agc tat ttc aat act tgg act ggc gat gtt ctg      1488
Tyr Gly Ala His Trp Ser Tyr Phe Asn Thr Trp Thr Gly Asp Val Leu
440                 445                 450 cgt gat gga aaa acg aat aca aag gaa cat ttg aaa aaa gtc tac aat      1536
Arg Asp Gly Lys Thr Asn Thr Lys Glu His Leu Lys Lys Val Tyr Asn
455                 460                 465                 470 cat gac aac gtg atc aca ctg gat gaa ctt ccc aag gga ttg tac ggc      1584
His Asp Asn Val Ile Thr Leu Asp Glu Leu Pro Lys Gly Leu Tyr Gly
                475                 480                 485 tgt cct aga tgg aaa taa                                              1602
Cys Pro Arg Trp Lys
            490

<210> SEQ ID NO 12
<211> LENGTH: 533
<212> TYPE: PRT
<213> ORGANISM: Paenibacillus sp.

<400> SEQUENCE: 12

Met Lys Ala Lys Ser Asp Ser Leu Ile Arg Cys Ser Thr Ser Asn Lys
        -40                 -35                 -30

Thr Tyr Phe Met Phe Gly Ser Ala Ile Phe Val Leu Tyr Ile Leu Met
    -25                 -20                 -15

Leu Ser Phe Thr His Ser Arg Val Glu Ala Ala Ile Thr Val Pro Gly
-10                  -5                 -1   1               5

Phe Val Val Glu Pro His Thr Ser Ser Asp Gln Asn Gln Ala Ile Ile
                10                  15                  20

Ala Thr Tyr Asn Asp Ala Ser Ile Glu Gly Tyr Gly Ile Lys Lys Arg
            25                  30                  35

Asp Glu Thr Thr Ala Lys Ala Glu Asp Leu Tyr Asp Gly Thr Gly
        40                  45                  50

Tyr Ile Ser Tyr Phe Glu Glu Asp Glu Lys Ala Thr Ala Gln Lys
55                  60                  65                  70

Gly Ser Ala Thr Phe His Val Lys Ala Pro Glu Asn Gly Leu Tyr Glu
                75                  80                  85

Leu Ser Leu Gly Tyr Tyr Ile Pro Glu Gly Asn Gly Asp Lys Ala Thr
            90                  95                  100

Ser Ile Gln Val Asn Gly Ser Gly Ala Gly Glu Leu Met Leu Ser Ala
        105                 110                 115

Pro Lys Gln Gly Thr Val Arg Ala Glu Lys Lys Met Thr Lys Val Leu
    120                 125                 130
```

-continued

Leu Asn Ser Gly Asn Asn Ser Ile Gln Ile Leu Arg Gly Trp Gly Tyr
135                 140                 145                 150

Tyr Gly Ile Glu Tyr Ile Lys Leu Glu Arg Val Glu Pro Arg Ile Thr
            155                 160                 165

Thr Gln Lys Thr Lys Met Asp Pro Leu Ser Asn Ser Lys Ala Ser Pro
        170                 175                 180

Gln Ala Lys Ala Leu Met Lys Phe Met Thr Asn Gln Tyr Gly Lys Lys
    185                 190                 195

Ile Ile Ser Gly Gln Gln Thr Leu Glu Asp Ala Thr Trp Ile Tyr Gln
200                 205                 210

Gln Thr Gly Lys Tyr Pro Ala Leu Val Ser Ser Asp Leu Met Asp Tyr
215                 220                 225                 230

Ser Pro Ser Arg Val Glu Asn Gly Ser Thr Ser Asn Glu Val Glu Lys
                235                 240                 245

Met Met Glu Trp Tyr Lys Arg Gly Ile Val Ser Leu Ser Trp His
            250                 255                 260

Trp Asn Ala Pro Lys Gly Ile Gly Gly Asn Glu Pro Gly His Glu Trp
            265                 270                 275

Trp Arg Gly Phe Asn Thr Glu Phe Thr Thr Phe Asp Val Glu Tyr Ala
280                 285                 290

Leu Asp His Pro Glu Ser Glu Asp Tyr Lys Leu Leu Ile Arg Asp Ile
295                 300                 305                 310

Asp Ala Ile Ala Ala Gln Leu Lys Arg Leu Gln Glu His His Ile Pro
                315                 320                 325

Val Leu Trp Arg Pro Leu His Glu Ala Glu Gly Gly Trp Phe Trp Trp
            330                 335                 340

Gly Ala Lys Gly Pro Glu Pro Ala Lys Lys Leu Tyr Arg Leu Met Tyr
            345                 350                 355

Glu Arg Leu Thr Glu Lys His Lys Leu Asn Asn Leu Ile Trp Val Trp
360                 365                 370

Asn Ser Val Lys Glu Glu Trp Tyr Pro Gly Asp Asp Val Val Asp Met
375                 380                 385                 390

Val Ser Val Asp Ile Tyr Asn Pro Pro Gly Asp His Ser Pro Ser Ile
            395                 400                 405

Ala Lys Tyr Asp Glu Leu Leu Phe Leu Ser Lys His Lys Lys Leu Val
        410                 415                 420

Ala Leu Ala Glu Asn Gly Pro Ile Pro Asp Pro Asp Leu Leu Gln Thr
    425                 430                 435

Tyr Gly Ala His Trp Ser Tyr Phe Asn Thr Trp Thr Gly Asp Val Leu
    440                 445                 450

Arg Asp Gly Lys Thr Asn Thr Lys Glu His Leu Lys Lys Val Tyr Asn
455                 460                 465                 470

His Asp Asn Val Ile Thr Leu Asp Glu Leu Pro Lys Gly Leu Tyr Gly
                475                 480                 485

Cys Pro Arg Trp Lys
            490

<210> SEQ ID NO 13
<211> LENGTH: 491
<212> TYPE: PRT
<213> ORGANISM: Paenibacillus sp.
<220> FEATURE:
<221> NAME/KEY: mat_peptide
<222> LOCATION: (1)..(491)

```
<400> SEQUENCE: 13

Ala Ile Thr Val Pro Gly Phe Val Val Glu Pro His Thr Ser Ser Asp
1               5                  10                  15

Gln Asn Gln Ala Ile Ile Ala Thr Tyr Asn Asp Ala Ser Ile Glu Gly
            20                  25                  30

Tyr Gly Ile Lys Lys Arg Asp Glu Thr Thr Ala Lys Ala Glu Asp Asp
        35                  40                  45

Leu Tyr Asp Gly Thr Gly Tyr Ile Ser Tyr Phe Phe Glu Glu Asp Glu
    50                  55                  60

Lys Ala Thr Ala Gln Lys Gly Ser Ala Thr Phe His Val Lys Ala Pro
65                  70                  75                  80

Glu Asn Gly Leu Tyr Glu Leu Ser Leu Gly Tyr Tyr Ile Pro Glu Gly
                85                  90                  95

Asn Gly Asp Lys Ala Thr Ser Ile Gln Val Asn Gly Ser Gly Ala Gly
            100                 105                 110

Glu Leu Met Leu Ser Ala Pro Lys Gln Gly Thr Val Arg Ala Glu Lys
        115                 120                 125

Lys Met Thr Lys Val Leu Leu Asn Ser Gly Asn Asn Ser Ile Gln Ile
    130                 135                 140

Leu Arg Gly Trp Gly Tyr Tyr Gly Ile Glu Tyr Ile Lys Leu Glu Arg
145                 150                 155                 160

Val Glu Pro Arg Ile Thr Thr Gln Lys Thr Lys Met Asp Pro Leu Ser
                165                 170                 175

Asn Ser Lys Ala Ser Pro Gln Ala Lys Ala Leu Met Lys Phe Met Thr
            180                 185                 190

Asn Gln Tyr Gly Lys Lys Ile Ile Ser Gly Gln Gln Thr Leu Glu Asp
        195                 200                 205

Ala Thr Trp Ile Tyr Gln Gln Thr Gly Lys Tyr Pro Ala Leu Val Ser
    210                 215                 220

Ser Asp Leu Met Asp Tyr Ser Pro Ser Arg Val Glu Asn Gly Ser Thr
225                 230                 235                 240

Ser Asn Glu Val Glu Lys Met Met Glu Trp Tyr Lys Arg Gly Ile
                245                 250                 255

Val Ser Leu Ser Trp His Trp Asn Ala Pro Lys Gly Ile Gly Gly Asn
                260                 265                 270

Glu Pro Gly His Glu Trp Trp Arg Gly Phe Asn Thr Glu Phe Thr Thr
        275                 280                 285

Phe Asp Val Glu Tyr Ala Leu Asp His Pro Glu Ser Glu Asp Tyr Lys
    290                 295                 300

Leu Leu Ile Arg Asp Ile Asp Ala Ile Ala Ala Gln Leu Lys Arg Leu
305                 310                 315                 320

Gln Glu His His Ile Pro Val Leu Trp Arg Pro Leu His Glu Ala Glu
                325                 330                 335

Gly Gly Trp Phe Trp Trp Gly Ala Lys Gly Pro Glu Pro Ala Lys Lys
            340                 345                 350

Leu Tyr Arg Leu Met Tyr Glu Arg Leu Thr Glu Lys His Lys Leu Asn
        355                 360                 365

Asn Leu Ile Trp Val Trp Asn Ser Val Lys Glu Trp Tyr Pro Gly
    370                 375                 380

Asp Asp Val Val Asp Met Val Ser Val Asp Ile Tyr Asn Pro Pro Gly
385                 390                 395                 400

Asp His Ser Pro Ser Ile Ala Lys Tyr Asp Glu Leu Leu Phe Leu Ser
                405                 410                 415
```

```
Lys His Lys Lys Leu Val Ala Leu Ala Glu Asn Gly Pro Ile Pro Asp
                420                 425                 430

Pro Asp Leu Leu Gln Thr Tyr Gly Ala His Trp Ser Tyr Phe Asn Thr
            435                 440                 445

Trp Thr Gly Asp Val Leu Arg Asp Gly Lys Thr Asn Thr Lys Glu His
450                 455                 460

Leu Lys Lys Val Tyr Asn His Asp Asn Val Ile Thr Leu Asp Glu Leu
465                 470                 475                 480

Pro Lys Gly Leu Tyr Gly Cys Pro Arg Trp Lys
                485                 490

<210> SEQ ID NO 14
<211> LENGTH: 1581
<212> TYPE: DNA
<213> ORGANISM: Artificial Sequence
<220> FEATURE:
<223> OTHER INFORMATION: Construct DNA of GH26 comprising a CBM domain
      wherein the native secretion signal was replaced with B.
      licheniformis secretion signal and HPHPHPHP tag was added directly
      on the C-terminal of the protein
<220> FEATURE:
<221> NAME/KEY: CDS
<222> LOCATION: (1)..(1578)
<220> FEATURE:
<221> NAME/KEY: sig_peptide
<222> LOCATION: (1)..(81)
<220> FEATURE:
<221> NAME/KEY: mat_peptide
<222> LOCATION: (82)..(1578)

<400> SEQUENCE: 14 atg aag aaa ccg ttg ggg aaa att gtc gca agc acc gca cta ctc att        48
Met Lys Lys Pro Leu Gly Lys Ile Val Ala Ser Thr Ala Leu Leu Ile
        -25                 -20                 -15 tct gtt gct ttt agt tca tcg ata gca tca gca gct att acg gta ccg        96
Ser Val Ala Phe Ser Ser Ser Ile Ala Ser Ala Ala Ile Thr Val Pro
        -10                 -5              -1  1               5 gga ttt gtc gtt gaa ccc cat act tct tct gat caa aac cag gcc ata       144
Gly Phe Val Val Glu Pro His Thr Ser Ser Asp Gln Asn Gln Ala Ile
                10                  15                  20 ata gcc aca tac aat gat gct tca atc gaa ggg tac ggg att aag aaa       192
Ile Ala Thr Tyr Asn Asp Ala Ser Ile Glu Gly Tyr Gly Ile Lys Lys
            25                  30                  35 cgt gat gag aca aca gcc aaa gcg gag gac gat tta tat gat ggc aca       240
Arg Asp Glu Thr Thr Ala Lys Ala Glu Asp Asp Leu Tyr Asp Gly Thr
        40                  45                  50 ggg tat atc tct tat ttt ttt gaa gag gat gaa aag gcc aca gct cag       288
Gly Tyr Ile Ser Tyr Phe Phe Glu Glu Asp Glu Lys Ala Thr Ala Gln
    55                  60                  65 aag ggg agt gct aca ttc cac gtt aaa gca cct gaa aat ggg ctt tat       336
Lys Gly Ser Ala Thr Phe His Val Lys Ala Pro Glu Asn Gly Leu Tyr
70                  75                  80                  85 gag tta agt ttg gga tac tac atc cct gaa gga aat ggg gat aaa gcg       384
Glu Leu Ser Leu Gly Tyr Tyr Ile Pro Glu Gly Asn Gly Asp Lys Ala
                90                  95                  100 act tct atc caa gtg aat ggt tcg gga gcc ggc gag ttg atg ctc agt       432
Thr Ser Ile Gln Val Asn Gly Ser Gly Ala Gly Glu Leu Met Leu Ser
            105                 110                 115 gcg cca aag caa ggg acg gtt cga gca gaa aaa aag atg aca aag gtg       480
Ala Pro Lys Gln Gly Thr Val Arg Ala Glu Lys Lys Met Thr Lys Val
        120                 125                 130 ctt ctg aac agc ggt aac aac tcc att caa ata tta agg ggg tgg ggg       528
```

```
            Leu Leu Asn Ser Gly Asn Asn Ser Ile Gln Ile Leu Arg Gly Trp Gly
                135                 140                 145 tac tat ggc att gaa tat atc aag ctt gaa cgt gta gaa ccc cgc ata             576
Tyr Tyr Gly Ile Glu Tyr Ile Lys Leu Glu Arg Val Glu Pro Arg Ile
150                 155                 160                 165 acc acg caa aaa aca aag atg gat ccc tta agc aac tcc aaa gca tct             624
Thr Thr Gln Lys Thr Lys Met Asp Pro Leu Ser Asn Ser Lys Ala Ser
                170                 175                 180 ccg caa gcc aaa gca tta atg aaa ttt atg acc aac cag tat gga aaa             672
Pro Gln Ala Lys Ala Leu Met Lys Phe Met Thr Asn Gln Tyr Gly Lys
                185                 190                 195 aag att ata tca ggg cag caa acc cta gag gac gca acg tgg atc tat             720
Lys Ile Ile Ser Gly Gln Gln Thr Leu Glu Asp Ala Thr Trp Ile Tyr
                200                 205                 210 cag cag aca ggt aag tac cct gca ctg gtt tcc agt gat ttg atg gat             768
Gln Gln Thr Gly Lys Tyr Pro Ala Leu Val Ser Ser Asp Leu Met Asp
215                 220                 225 tat tct cca tcc cgt gtg gaa aac gga agc acc tcg aat gag gta gaa             816
Tyr Ser Pro Ser Arg Val Glu Asn Gly Ser Thr Ser Asn Glu Val Glu
230                 235                 240                 245 aag atg atg gag tgg tac aag cgt gga gga att gtc tcc tta agc tgg             864
Lys Met Met Glu Trp Tyr Lys Arg Gly Gly Ile Val Ser Leu Ser Trp
                250                 255                 260 cac tgg aat gcg ccg aaa ggg atc ggc ggc aat gaa cca ggc cac gag             912
His Trp Asn Ala Pro Lys Gly Ile Gly Gly Asn Glu Pro Gly His Glu
                265                 270                 275 tgg tgg cgg ggg ttt aat aca gaa ttc aca acc ttc gat gta gaa tat             960
Trp Trp Arg Gly Phe Asn Thr Glu Phe Thr Thr Phe Asp Val Glu Tyr
                280                 285                 290 gcc ttg gat cat ccg gaa tcg gaa gat tac aag ctt tta atc cgg gat            1008
Ala Leu Asp His Pro Glu Ser Glu Asp Tyr Lys Leu Leu Ile Arg Asp
295                 300                 305 att gat gcg atc gct gct caa ttg aag cgg ctg cag gaa cac cat att            1056
Ile Asp Ala Ile Ala Ala Gln Leu Lys Arg Leu Gln Glu His His Ile
310                 315                 320                 325 ccc gta ctt tgg aga ccg ttg cat gaa gcg gag ggc ggc tgg ttt tgg            1104
Pro Val Leu Trp Arg Pro Leu His Glu Ala Glu Gly Gly Trp Phe Trp
                330                 335                 340 tgg gga gcc aaa ggt cct gag cct gcc aag aaa ttg tat aga tta atg            1152
Trp Gly Ala Lys Gly Pro Glu Pro Ala Lys Lys Leu Tyr Arg Leu Met
                345                 350                 355 tac gaa cga ttg acg gaa aag cac aag tta aac aat ctc att tgg gtt            1200
Tyr Glu Arg Leu Thr Glu Lys His Lys Leu Asn Asn Leu Ile Trp Val
                360                 365                 370 tgg aac tct gtt aag gag gag tgg tac ccg gga gat gat gtg gtg gat            1248
Trp Asn Ser Val Lys Glu Glu Trp Tyr Pro Gly Asp Asp Val Val Asp
375                 380                 385 atg gta agt gtc gac att tat aat cca ccc ggt gat cac agc cca agc            1296
Met Val Ser Val Asp Ile Tyr Asn Pro Pro Gly Asp His Ser Pro Ser
390                 395                 400                 405 att gcc aag tac gac gag ctc ttg ttt ctg agc aag cat aag aaa ctt            1344
Ile Ala Lys Tyr Asp Glu Leu Leu Phe Leu Ser Lys His Lys Lys Leu
                410                 415                 420 gtg gca ctc gcc gaa aat ggg ccg att ccc gat cct gat ctg ctg cag            1392
Val Ala Leu Ala Glu Asn Gly Pro Ile Pro Asp Pro Asp Leu Leu Gln
                425                 430                 435 act tac ggt gca cat tgg agc tat ttc aat act tgg act ggc gat gtt            1440
Thr Tyr Gly Ala His Trp Ser Tyr Phe Asn Thr Trp Thr Gly Asp Val
                440                 445                 450
```

```
ctg cgt gat gga aaa acg aat aca aag gaa cat ttg aaa aaa gtc tac      1488
Leu Arg Asp Gly Lys Thr Asn Thr Lys Glu His Leu Lys Lys Val Tyr
    455                 460                 465 aat cat gac aac gtg atc aca ctg gat gaa ctt ccc aag gga ttg tac      1536
Asn His Asp Asn Val Ile Thr Leu Asp Glu Leu Pro Lys Gly Leu Tyr
470                 475                 480                 485 ggc tgt cct aga tgg aaa cat ccg cac cct cat cca cac ccg taa          1581
Gly Cys Pro Arg Trp Lys His Pro His Pro His Pro His Pro
                490                 495
```

```
<210> SEQ ID NO 15
<211> LENGTH: 526
<212> TYPE: PRT
<213> ORGANISM: Artificial Sequence
<220> FEATURE:
<223> OTHER INFORMATION: Synthetic Construct

<400> SEQUENCE: 15

Met Lys Lys Pro Leu Gly Lys Ile Val Ala Ser Thr Ala Leu Leu Ile
        -25                 -20                 -15

Ser Val Ala Phe Ser Ser Ser Ile Ala Ser Ala Ala Ile Thr Val Pro
    -10                  -5              -1   1                 5

Gly Phe Val Val Glu Pro His Thr Ser Ser Asp Gln Asn Gln Ala Ile
                    10                  15                  20

Ile Ala Thr Tyr Asn Asp Ala Ser Ile Glu Gly Tyr Gly Ile Lys Lys
                25                  30                  35

Arg Asp Glu Thr Thr Ala Lys Ala Glu Asp Leu Tyr Asp Gly Thr
                40                  45                  50

Gly Tyr Ile Ser Tyr Phe Phe Glu Glu Asp Glu Lys Ala Thr Ala Gln
    55                  60                  65

Lys Gly Ser Ala Thr Phe His Val Lys Ala Pro Glu Asn Gly Leu Tyr
70                  75                  80                  85

Glu Leu Ser Leu Gly Tyr Tyr Ile Pro Glu Gly Asn Gly Asp Lys Ala
                90                  95                  100

Thr Ser Ile Gln Val Asn Gly Ser Gly Ala Gly Glu Leu Met Leu Ser
                105                 110                 115

Ala Pro Lys Gln Gly Thr Val Arg Ala Glu Lys Lys Met Thr Lys Val
                120                 125                 130

Leu Leu Asn Ser Gly Asn Asn Ser Ile Gln Ile Leu Arg Gly Trp Gly
    135                 140                 145

Tyr Tyr Gly Ile Glu Tyr Ile Lys Leu Glu Arg Val Glu Pro Arg Ile
150                 155                 160                 165

Thr Thr Gln Lys Thr Lys Met Asp Pro Leu Ser Asn Ser Lys Ala Ser
                170                 175                 180

Pro Gln Ala Lys Ala Leu Met Lys Phe Met Thr Asn Gln Tyr Gly Lys
                185                 190                 195

Lys Ile Ile Ser Gly Gln Gln Thr Leu Glu Asp Ala Thr Trp Ile Tyr
            200                 205                 210

Gln Gln Thr Gly Lys Tyr Pro Ala Leu Val Ser Ser Asp Leu Met Asp
        215                 220                 225

Tyr Ser Pro Ser Arg Val Glu Asn Gly Ser Thr Ser Asn Glu Val Glu
230                 235                 240                 245

Lys Met Met Glu Trp Tyr Lys Arg Gly Gly Ile Val Ser Leu Ser Trp
                250                 255                 260

His Trp Asn Ala Pro Lys Gly Ile Gly Gly Asn Glu Pro Gly His Glu
            265                 270                 275
```

```
Trp Trp Arg Gly Phe Asn Thr Glu Phe Thr Thr Phe Asp Val Glu Tyr
            280                 285                 290

Ala Leu Asp His Pro Glu Ser Glu Asp Tyr Lys Leu Leu Ile Arg Asp
        295                 300                 305

Ile Asp Ala Ile Ala Ala Gln Leu Lys Arg Leu Gln Glu His His Ile
310                 315                 320                 325

Pro Val Leu Trp Arg Pro Leu His Glu Ala Glu Gly Gly Trp Phe Trp
                330                 335                 340

Trp Gly Ala Lys Gly Pro Glu Pro Ala Lys Lys Leu Tyr Arg Leu Met
            345                 350                 355

Tyr Glu Arg Leu Thr Glu Lys His Lys Leu Asn Asn Leu Ile Trp Val
        360                 365                 370

Trp Asn Ser Val Lys Glu Glu Trp Tyr Pro Gly Asp Asp Val Val Asp
    375                 380                 385

Met Val Ser Val Asp Ile Tyr Asn Pro Pro Gly Asp His Ser Pro Ser
390                 395                 400                 405

Ile Ala Lys Tyr Asp Glu Leu Leu Phe Leu Ser Lys His Lys Lys Leu
                410                 415                 420

Val Ala Leu Ala Glu Asn Gly Pro Ile Pro Asp Pro Asp Leu Leu Gln
            425                 430                 435

Thr Tyr Gly Ala His Trp Ser Tyr Phe Asn Thr Trp Thr Gly Asp Val
        440                 445                 450

Leu Arg Asp Gly Lys Thr Asn Thr Lys Glu His Leu Lys Lys Val Tyr
    455                 460                 465

Asn His Asp Asn Val Ile Thr Leu Asp Glu Leu Pro Lys Gly Leu Tyr
470                 475                 480                 485

Gly Cys Pro Arg Trp Lys His Pro His Pro His Pro His Pro
                490                 495

<210> SEQ ID NO 16
<211> LENGTH: 8
<212> TYPE: PRT
<213> ORGANISM: Artificial Sequence
<220> FEATURE:
<223> OTHER INFORMATION: HPHPHPHP tag

<400> SEQUENCE: 16

His Pro His Pro His Pro His Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

His His His His His His
1               5
```

The invention claimed is:

1. A detergent composition comprising a surfactant and a polypeptide having mannanase activity, wherein the polypeptide is selected from the group consisting of:
   (a) a polypeptide having at least 99% sequence identity to SEQ ID NO: 4;
   (b) a polypeptide comprising the polypeptide of (a) and an N-terminal and/or C-terminal His-tag and/or HQ-tag;
   (c) a polypeptide comprising the polypeptide of (a) and an N-terminal and/or C-terminal extension of up to 10 amino acids; and
   (d) a fragment of the polypeptide of SEQ ID NO: 4, which has mannanase activity and at least 90% of the length of SEQ ID NO: 4.

2. The detergent composition of claim 1, wherein the polypeptide has at least 99% sequence identity to SEQ ID NO: 4.

3. The detergent composition of claim 1, wherein the polypeptide comprises the amino acid sequence of SEQ ID NO: 4.

4. The detergent composition of claim 1, which is in the form of a bar, a tablet, a powder, a granule, a paste or a liquid.

5. The detergent composition of claim 1, further comprising an alpha-amylase, a protease, or a combination thereof.

6. The detergent composition of claim 1, further comprising one or more components selected from the group consisting of hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants and solubilizers.

7. The detergent composition of claim 1, which is a liquid composition and further comprises a polyol.

8. A granule comprising a core particle and one or more coatings, wherein the granule comprises a polypeptide having mannanase activity selected from the group consisting of:
(a) a polypeptide having at least 99% sequence identity to SEQ ID NO: 4;
(b) a polypeptide comprising the polypeptide of (a) and an N-terminal and/or C-terminal His-tag and/or HQ-tag;
(c) a polypeptide comprising the polypeptide of (a) and an N-terminal and/or C-terminal extension of up to 10 amino acids; and
(d) a fragment of the polypeptide of SEQ ID NO: 4, which has mannanase activity and at least 90% of the length of SEQ ID NO: 4.

9. The granule of claim 8, wherein the polypeptide has at least 99% sequence identity to SEQ ID NO: 4.

10. The granule of claim 8, wherein the polypeptide comprises the amino acid sequence of SEQ ID NO: 4.

11. A process for degrading mannan, comprising treating the mannan with a polypeptide having mannanase activity selected from the group consisting of:
(a) a polypeptide having at least 99% sequence identity to SEQ ID NO: 4;
(b) a polypeptide comprising the polypeptide of (a) and an N-terminal and/or C-terminal His-tag and/or HQ-tag;
(c) a polypeptide comprising the polypeptide of (a) and an N-terminal and/or C-terminal extension of up to 10 amino acids; and
(d) a fragment of the polypeptide of SEQ ID NO: 4, which has mannanase activity and at least 90% of the length of SEQ ID NO: 4.

12. The method of claim 11, wherein the mannan is linear mannan, galactomannan, glucomannan or galactoglucomannan.

13. A recombinant host cell comprising multiple copies of a polynucleotide encoding a polypeptide having mannanase activity operably linked to one or more control sequences that direct the production of the polypeptide, wherein the polypeptide is selected from the group consisting of:
(a) a polypeptide having at least 99% sequence identity to SEQ ID NO: 4;
(b) a polypeptide comprising the polypeptide of (a) and an N-terminal and/or C-terminal His-tag and/or HQ-tag;
(c) a polypeptide comprising the polypeptide of (a) and an N-terminal and/or C-terminal extension of up to 10 amino acids; and
(d) a fragment of the polypeptide of SEQ ID NO: 4, which has mannanase activity and at least 90% of the length of SEQ ID NO: 4.

14. A process of producing a polypeptide having mannanase activity, comprising:
(a) cultivating the host cell of claim 13 under conditions conducive for production of the polypeptide; and
(b) recovering the polypeptide.

15. The detergent composition of claim 1, wherein the polypeptide having at least 99% sequence identity to SEQ ID NO: 4 comprises an alteration at 1, 2, 3, or 4 positions of SEQ ID NO: 4.

16. The detergent composition of claim 1, wherein the polypeptide further comprises a carbohydrate binding module (CBM).

17. The granule of claim 8, wherein the polypeptide having at least 99% sequence identity to SEQ ID NO: 4 an alteration at 1, 2, 3, or 4 positions of SEQ ID NO: 4.

18. The granule of claim 8, wherein the polypeptide further comprises a carbohydrate binding module (CBM).

* * * * *

UNITED STATES PATENT AND TRADEMARK OFFICE
CERTIFICATE OF CORRECTION

| | |
|---|---|
| PATENT NO. | : 11,732,221 B2 |
| APPLICATION NO. | : 16/649350 |
| DATED | : August 22, 2023 |
| INVENTOR(S) | : Hoff et al. |

It is certified that error appears in the above-identified patent and that said Letters Patent is hereby corrected as shown below:

In the Claims

Claim 17 (Column 118, Lines 38-41) should read as follows:
17. The granule of claim 8, wherein the polypeptide having at least 99% sequence identity to SEQ ID NO: 4 comprises an alteration at 1, 2, 3, or 4 positions of SEQ ID NO: 4.

Signed and Sealed this
Twenty-fourth Day of September, 2024

Katherine Kelly Vidal
*Director of the United States Patent and Trademark Office*